(12) United States Patent
Brubaker et al.

(10) Patent No.: US 12,311,118 B2
(45) Date of Patent: *May 27, 2025

(54) BODY FLUID MOVEMENT SYSTEM

(71) Applicants: William Brubaker, Palo Alto, CA (US); Paul Davis, Los Altos Hills, CA (US)

(72) Inventors: William Brubaker, Palo Alto, CA (US); Paul Davis, Los Altos Hills, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/906,270

(22) Filed: Oct. 4, 2024

(65) Prior Publication Data

US 2025/0050058 A1 Feb. 13, 2025

Related U.S. Application Data

(63) Continuation-in-part of application No. 18/208,064, filed on Jun. 9, 2023, now Pat. No. 12,121,670.

(51) Int. Cl.
*A61M 25/00* (2006.01)
*A61F 5/44* (2006.01)
(Continued)

(52) U.S. Cl.
CPC ....... *A61M 25/0017* (2013.01); *A61F 5/4405* (2013.01); *A61F 5/4408* (2013.01); *A61F 5/453* (2013.01); *A61M 25/10* (2013.01)

(58) Field of Classification Search
CPC .............. A61M 39/1011; A61M 39/10; A61M 2039/1027; A61M 2039/1066; A61M 2202/0496; A61M 39/165; A61M 2039/1033; A61M 2039/1077; A61M 39/1055; A61M 2025/024;
(Continued)

(56) References Cited

U.S. PATENT DOCUMENTS 3,661,143 A 5/1972 Henkin
4,029,099 A 6/1977 Fifield
(Continued)

FOREIGN PATENT DOCUMENTS

EP 0108736 A1 5/1984
EP 2956204 B1 12/2015
(Continued)

*Primary Examiner* — Adam Marcetich
(74) *Attorney, Agent, or Firm* — Paul Davis

(57) ABSTRACT

A body fluid movement system includes a locking mechanism without with an integrated-check-valve, a pleated segment and not being swivel snap connector. The locking mechanism is positioned in a surrounding relationship around an entirety of an exterior of the output and inlet ports, providing a compression force applied by the locking mechanism to all of the exteriors of the output and inlet ports. The locking mechanism locks the output port and inlet port along with the locking mechanism when the patient's leg moves more than a predetermined distance. The locking mechanism is configured to provide leak free flow of urine from the bladder to the drainage bag and being usable with different drainage bags and body fluid movement apparatus, and can continue to lock the outlet and inlet ports when the body fluid is drained from the drainage bag.

19 Claims, 41 Drawing Sheets

(51) Int. Cl.
*A61F 5/453* (2006.01)
*A61M 25/10* (2013.01)

(58) Field of Classification Search
CPC .. A61M 2039/1016; A61M 2039/1072; A61M 25/02; A61F 5/4405; A61F 5/4404; A61F 5/44; A61F 5/4408; A61J 1/10; A61J 1/1412; Y10S 604/905; Y10S 128/912
See application file for complete search history.

(56) References Cited

U.S. PATENT DOCUMENTS

| | | | |
|---|---|---|---|
| 4,049,034 A * | 9/1977 | Vcelka | A61J 1/1475 383/906 |
| 4,280,498 A * | 7/1981 | Jensen | A61F 5/4405 604/323 |
| 4,319,573 A | 3/1982 | Whitlock | |
| 4,340,052 A * | 7/1982 | Dennehey | A61M 39/1011 604/905 |
| 4,421,509 A | 12/1983 | Schneider et al. | |
| 4,483,688 A | 11/1984 | Akiyama | |
| 4,583,967 A | 4/1986 | Harris | |
| 4,631,056 A | 12/1986 | Dye | |
| 4,704,177 A | 11/1987 | Vaillancourt | |
| 4,801,296 A | 1/1989 | Vaillancourt | |
| 4,826,486 A | 5/1989 | Palsrok et al. | |
| 4,830,914 A | 5/1989 | Vaillancourt | |
| 4,834,706 A | 5/1989 | Beck et al. | |
| 4,854,737 A * | 8/1989 | Steer | A61F 5/4404 604/326 |
| 5,248,306 A | 9/1993 | Clark et al. | |
| 5,531,695 A | 7/1996 | Swisher | |
| 5,728,061 A | 3/1998 | Ahmed | |
| 5,803,509 A | 9/1998 | Adams | |
| 5,957,894 A | 9/1999 | Kerwin et al. | |
| 10,322,247 B1 | 6/2019 | Radcliffe, Jr. | |
| 11,241,566 B1 | 2/2022 | Lindsay | |
| 11,389,248 B1 | 7/2022 | Roh et al. | |
| 12,089,905 B1 | 9/2024 | Roh et al. | |
| 2003/0032944 A1 | 2/2003 | Cawood | |
| 2006/0271019 A1 | 11/2006 | Stoller et al. | |
| 2007/0225688 A1 | 9/2007 | Goodwin | |
| 2007/0244468 A1 | 10/2007 | Kostandaras | |
| 2008/0129042 A1 * | 6/2008 | Weigel | A61M 39/1011 285/330 |
| 2008/0171992 A1 | 7/2008 | House | |
| 2010/0228231 A1 | 9/2010 | Weigel et al. | |
| 2010/0286667 A1 | 11/2010 | Paz | |
| 2011/0087181 A1 | 4/2011 | Bidwell et al. | |
| 2012/0089129 A1 | 4/2012 | Engelhardt | |
| 2012/0172822 A1 | 7/2012 | Gilman | |
| 2012/0184944 A1 | 7/2012 | Tomes et al. | |
| 2012/0214337 A1 | 8/2012 | Schnell et al. | |
| 2012/0232547 A1 | 9/2012 | Cohen | |
| 2013/0172840 A1 | 7/2013 | Lampotang et al. | |
| 2014/0100547 A1 | 4/2014 | Lyons et al. | |
| 2014/0334974 A1 * | 11/2014 | Rasooly | A61L 2/10 250/455.11 |
| 2015/0051588 A1 | 2/2015 | Miller et al. | |
| 2015/0126975 A1 | 5/2015 | Wuthier | |
| 2015/0290449 A1 | 10/2015 | Yanik | |
| 2016/0051395 A1 * | 2/2016 | Ugarte | A61F 5/4404 604/327 |
| 2016/0146386 A1 * | 5/2016 | Blake | F16L 33/025 285/45 |
| 2016/0166822 A1 * | 6/2016 | Dodson | A61M 39/10 604/533 |
| 2016/0193073 A1 | 7/2016 | Kinsey et al. | |
| 2016/0296741 A1 * | 10/2016 | Patterson | A61M 39/1011 |
| 2017/0113000 A1 | 4/2017 | Tobescu et al. | |
| 2017/0368308 A1 | 12/2017 | Hofius et al. | |
| 2018/0169377 A1 | 6/2018 | Hickmott et al. | |
| 2018/0304045 A1 | 10/2018 | Glithero et al. | |
| 2018/0340639 A1 * | 11/2018 | Requate | F16L 33/02 |
| 2019/0105465 A1 | 4/2019 | Erbey, II et al. | |
| 2019/0217076 A1 | 7/2019 | O'Neil | A61M 39/10 |
| 2019/0282793 A1 * | 9/2019 | Stafford | A61M 39/08 |
| 2019/0314188 A1 | 10/2019 | Barrientos | |
| 2019/0321587 A1 | 10/2019 | McMenamin et al. | |
| 2019/0321593 A1 | 10/2019 | Crawford | |
| 2020/0269011 A1 | 8/2020 | Carlsson | |
| 2020/0300718 A1 | 9/2020 | Bogdanovich et al. | |
| 2020/0408350 A1 | 12/2020 | Walterspiel | |
| 2021/0022911 A1 * | 1/2021 | Scalise | A61F 5/445 |
| 2021/0100533 A1 | 4/2021 | Seres et al. | |
| 2021/0187240 A1 | 6/2021 | Waitkus et al. | |
| 2021/0299337 A1 | 9/2021 | Scott | |
| 2021/0379269 A1 | 12/2021 | Justice et al. | |
| 2022/0071516 A1 | 3/2022 | Dove | |
| 2022/0151816 A1 * | 5/2022 | Allen | A61F 5/4407 |
| 2022/0296871 A1 | 9/2022 | Hickman | |
| 2022/0362509 A1 | 11/2022 | Arevalos et al. | |

FOREIGN PATENT DOCUMENTS

| | | | |
|---|---|---|---|
| KR | 20230144241 A * | 10/2023 | |
| WO | WO-2023079300 A1 * | 5/2023 | A61F 5/44 |

* cited by examiner (CONT.)
↓

414 — THE SEARCH ENGINE UTILIZES THE USER SUPPLIED CRITERIA TO QUERY FOR RELEVANT TRAINED AI OBJECTS BY REFERRING TO 1) THE SIGNATURES OF THE STORED AI OBJECTS AS WELL AS 2) ANY INDEXED PARAMETERS FOR THE AI OBJECTS INDEXED BY THE AI DATABASE

416 — A USER INTERFACE PRESENTS A POPULATION OF KNOWN TRAINED AI OBJECTS; AND SEARCHING THE POPULATION OF KNOWN TRAINED AI OBJECTS TO RETURN A SET OF ONE OR MORE ALREADY TRAINED AI OBJECTS SIMILAR TO A PROBLEM TRYING TO BE SOLVED BY THE USER SUPPLYING THE SEARCH CRITERIA

418 — THE AI DATABASE IS CONFIGURED TO BE A SET OF ONE OR MORE DATABASES SO THAT EACH DATABASE HAS A DIFFERENT PROFILE AND INDEXING. THE SET OF DATABASES ARE CONFIGURED TO OPERATE IN A PARALLEL TO THEN SEND BACK ACCURATE, FAST, AND EFFICIENT RETURNS OF TRAINED AI OBJECTS THAT SATISFY THE SEARCH QUERY

420 — THE AI DATABASE COOPERATE WITH THE AI ENGINE TO SUPPLY ONE OR MORE AI OBJECTS. THE AI ENGINE INCLUDES AN ARCHITECT MODULE CONFIGURED TO CREATE AND OPTIMIZE LEARNING TOPOLOGIES OF NEURAL NETWORKS FOR THE AI OBJECTS; AN INSTRUCTOR MODULE CONFIGURED TO CARRYING OUT A TRAINING PLAN CODIFIED IN A PEDAGOGICAL SOFTWARE PROGRAMMING LANGUAGE; AND A LEARNER MODULE CONFIGURED TO CARRYING OUT AN ACTUAL EXECUTION OF UNDERLYING ARTIFICIAL INTELLIGENCE LEARNING ALGORITHMS DURING A TRAINING SESSION, WHERE THE ARCHITECT MODULE, WHEN RECONFIGURING OR RECOMPOSING THE AI OBJECTS, COMPOSES THE ONE OR MORE TRAINED AI DATA OBJECTS INTO A NEW AI MODEL AND THE INSTRUCTOR MODULE AND LEARNER MODULE COOPERATE WITH ONE OR MORE DATA SOURCES TO TRAIN THE NEW AI MODEL

422 — THE AI DATABASE COOPERATES WITH AN AI ENGINE TO CAUSE ANY OF REUSE, RECONFIGURE ABILITY, AND RECOMPOSITION OF THE ONE OR MORE TRAINED AI DATA OBJECTS INTO A NEW TRAINED AI MODEL

↓
(END)

FIG. 29B

BODY FLUID MOVEMENT SYSTEM

BACKGROUND

Field of the Invention

This invention relates to body fluid movement systems, and more specifically to body fluid movement systems that include a locking mechanism.

Description of the Related Art

A person may have limited or impaired mobility, making the normal urination process difficult or impossible. For example, a person may have surgery or a disability that prevents movement. In another example, a person may have limited travel conditions, such as the experience of pilots, drivers and workers in hazardous areas. Additionally, fluid collection from humans may be required for monitoring purposes or for clinical testing.

Patient bed pans and urinary catheters such as the Foley catheter can be used to address some of these circumstances. However, urinary and urinary catheters have several problems associated with them. For example, the urinary cavity is prone to discomfort, spillage and other hygiene problems. Urinary catheters can be uncomfortable and painful and can lead to urinary tract infections.

Accordingly, users and manufacturers of fluid collection devices continue to seek new and improved devices, systems, and methods for urine collection.

One type of body fluid collection system includes a fluid impermeable barrier that at least partially defines a chamber, the fluid impermeable barrier also defining an opening extending therethrough, the opening positioned adjacent to or passing through the female urethra. It is configured to have a male urethra. The fluid collection member includes a wicking material disposed at least partially within the chamber. The fluid collection member includes a conduit disposed within the chamber, and the conduit includes an inlet disposed within the fluid collection device and an outlet configured to be in fluid communication with the portable vacuum source. The fluid collection device includes one or more flanges extending outwardly from the fluid collection member, and the one or more flanges include an adhesive member thereon.

One type of fluid collection system includes a fluid storage vessel configured to contain fluid. The fluid collection system includes a fluid collection device in fluid communication with the fluid storage vessel. The fluid collection device includes a fluid collection member. The fluid collection member includes a fluid impermeable barrier at least partially defining the chamber, the fluid impermeable barrier also defining an opening extending therethrough, the opening positioned adjacent to or passing through the male urethra. It is configured to have a urethra. The fluid collection member includes a wicking material at least partially disposed within the chamber. The fluid collection member includes a conduit disposed within the chamber, and the conduit includes an inlet disposed within the fluid collection device and an outlet configured to be in fluid communication with the portable vacuum source. The fluid collection device includes at least one flange extending outwardly from the fluid collection member, and the at least one flange includes an adhesive member thereon. The fluid collection system includes a vacuum source in fluid communication with at least one of a fluid storage vessel or a fluid collection device, the vacuum source configured to draw fluid from the fluid collection device.

In one embodiment, a method of collecting fluid is disclosed. The method includes positioning an opening of the fluid collection device adjacent to or about the male urethra, the opening being defined by a fluid impermeable barrier of the fluid collection device. The method includes positioning the fluid collection device on a user. The method includes placing fluid received from the female urethra or the male urethra into a chamber of a fluid collection device, the chamber of the fluid collection device being at least partially defined by a fluid impervious barrier.

The Foley body fluid movement has been used since the 1930s in much the same form as its earlier model. The Foley body fluid movement, in its most basic form, has a proximal portion that remains outside the body, a length that traverses the urethra, and a distal end that resides in the bladder. The Foley body fluid movement is held in place by an inflatable bladder retention member at the distal end, which stabilizes the device in place and prevents unintentional withdrawal from the bladder. A typical Foley body fluid movement includes at least two lumens along its length, one lumen serving as a conduit for draining the bladder and a second lumen to inflate the bladder retention member to hold the body fluid movement in place in the bladder.

Various developments have added diagnostic capabilities to Foley body fluid movement s, including pressure and temperature measurement capabilities. For example, Singer, Patent Document 1, discloses a body fluid movement having an oxygen sensing function. Both Rhea and U.S. Pat. No. 5,057,059 and 1993, disclose pressure sensors associated with Foley body fluid movement s. U.S. Pat. No. 6,057,059 to Noda discloses a temperature sensor associated with a Foley type body fluid movement.

Urinary body fluid movement s are medical devices that are widely used for the management of urinary retention and incontinence. These body fluid movement s are inserted into the bladder through the urethra to drain urine. Urinary body fluid movement s are used in various settings, including hospitals, long-term care facilities, and home healthcare. It is estimated that 15-25% of hospitalized patients will receive a urinary body fluid movement during their stay. There are also patients who will require a long-term indwelling urinary body fluid movement to manage their bladder.

The kidneys make approximately 1.5 liters of urine daily and typical bladder capacity is 300 to 500 milliliters. When a person is unable to urinate, the problem can quickly become serious. As urine builds up in the bladder, it becomes uncomfortable, then painful. If the problem continues, the bladder can become overly full and urine can back up into a patient's kidneys, causing damage that can be permanent. When this happens, a sterile, flexible body fluid movement tubes with lumens called a urinary body fluid movement is inserted into the urethra (where urine leaves the body) and is gently pushed up until the end rests in a patient's bladder. The body fluid movement then drains the urine, through attached tubing to a gravity drainage bag.

Urinary body fluid movements are often used during surgery, as a patient cannot control its bladder while under anesthesia. For this purpose, a Foley body fluid movement is typically placed prior to surgery and keeps the bladder empty throughout. It often remains in place until the surgery is completed and a patient is awake and alert enough to begin urinating normally. A Foley body fluid movement is a sterile urinary body fluid movement that is intended to stay in place for an extended period of time.

If pathogens enter the urinary tract, they may cause an infection. Many of the pathogens that cause a body fluid movement-associated urinary tract infection are commonly found in a patient's intestines that do not usually cause an infection there. Pathogens can enter the urinary tract when the body fluid movement is being put in or while the body fluid movement remains in the bladder.

The longer a urinary body fluid movement stays in the bladder, the greater the chance of infection. Infection is the most common problem. The body fluid movement may let pathogens into a patient's body, where they can cause an infection of the bladder, urethra, urinary tract, or kidneys.

Medical data is typically rich, rapidly growing, and relatively complex in structure. Machine learning (ML) techniques can combine medical datasets from millions of patients, such as diagnostic profiles, imaging records, and wearable information, to analyze the internal structure of the ocean of medical big data, identify patterns of disease conditions, and overcome the general limitations on access to local datasets. Furthermore, the next-generation healthcare system supported by big data shifts from a centralized hospital-based mode to a parallel mode of monitoring at home, screening and detection at point-of-care testing (POCT), and monitoring during hospitalization, meanwhile, achieves doctor-patient interaction and data transferring via the cloud to ease healthcare resource crowding and facilitate personalized healthcare).

Ultimately, systematic health status assessment from comprehensive individual information is used for clinical applications to achieve improved data processing capabilities and resource optimization in healthcare. In this perspective, we present the latest advances in AI in clinical diagnosis from three perspectives on off-body detection, near-body monitoring, disease prediction and CDSS The challenges and opportunities of AI in personalized medicine in the future are deeply considered and discussed.

There is also a need for improved body drainage systems.

SUMMARY

An object of the present invention is to provide a body fluid movement system with a body fluid apparatus coupled to a drainage bag, with the two remaining coupled when the drainage bag moves.

Another object of the present invention is to provide a body fluid movement system with a locking/tight/secure mechanism that couples a body fluid apparatus attach/detach to a drainage bag.

A further object of the present invention is to provide a body fluid movement system, with a body fluid apparatus coupled to a drainage bag, with the two remaining coupled irrespective of body movement.

These and other objects of the present invention are achieved in, a body fluid movement system that includes a body fluid movement tube with a lumen, a proximal end, a distal end and a balloon coupled to the proximal end. A balloon is configured to be positioned in an interior of a bladder. The proximal end is configured to provide flow of a flow of a body fluid from the bladder, through the body fluid movement lumen, and delivers the body fluid to a drainage bag. The drainage bag has an inlet port for receiving urine and an outlet port for draining urine from the drainage bag. The body fluid movement tube includes the proximal end and the proximal end, with a plurality of urine draining holes that receive urine from the bladder and allow it to be transported to and though the urinary body fluid movement tube. The inlet port of the drainage bag and the outlet port of the body fluid movement apparatus tube are locked together by a lock device without a pleated segment or a corrugated segment and is not part of the drainage bag or the body fluid movement apparatus, and positioned in a surrounding relationship at an exterior of the outlet and inlet ports, providing a non-tensile compression force that is applied by the locking mechanism to the outlet and inlet ports at an exterior of the drainage bag.

BRIEF DESCRIPTION OF THE DRAWINGS

FIGS. 29A and 29B a flow diagram of an embodiment of an AI database cooperating with a search engine and AI engine.

DETAILED DESCRIPTION

Figure 1:
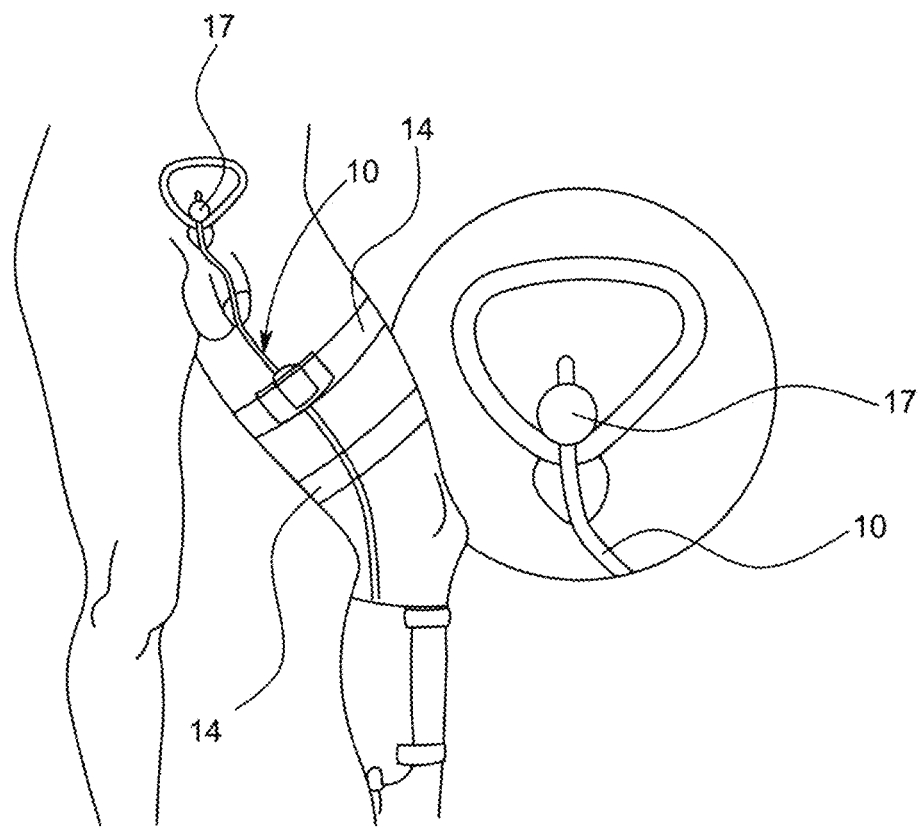
FIGS. 1-4 illustrate one embodiment of a flexible body fluid movement system.
Figure 2:
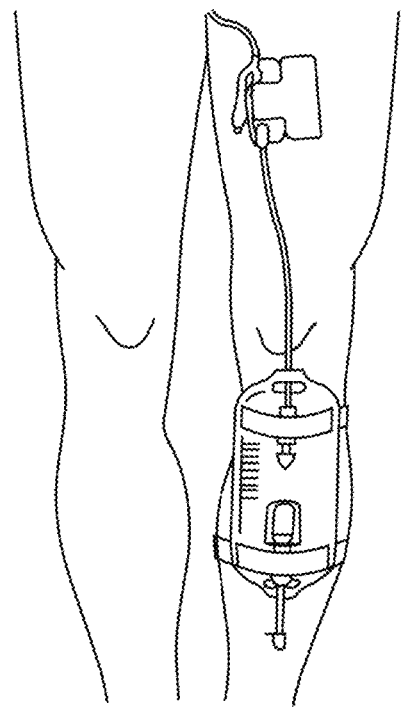
Figure 3:
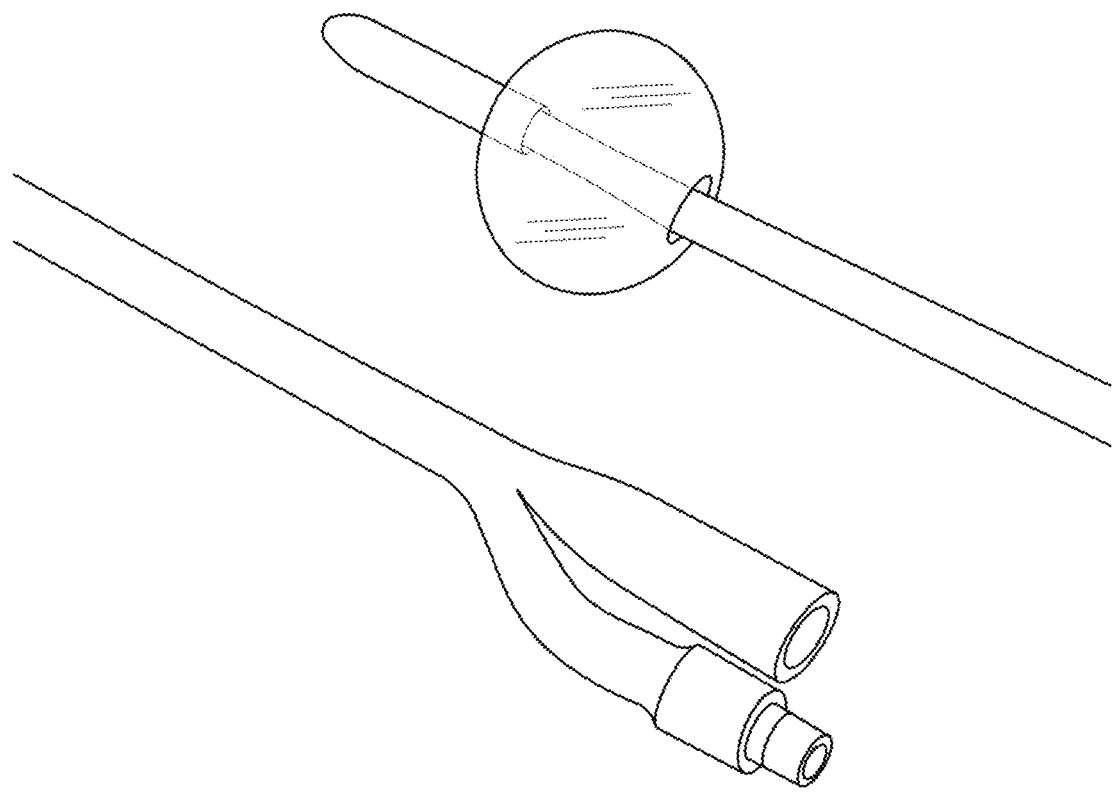
Figure 4:
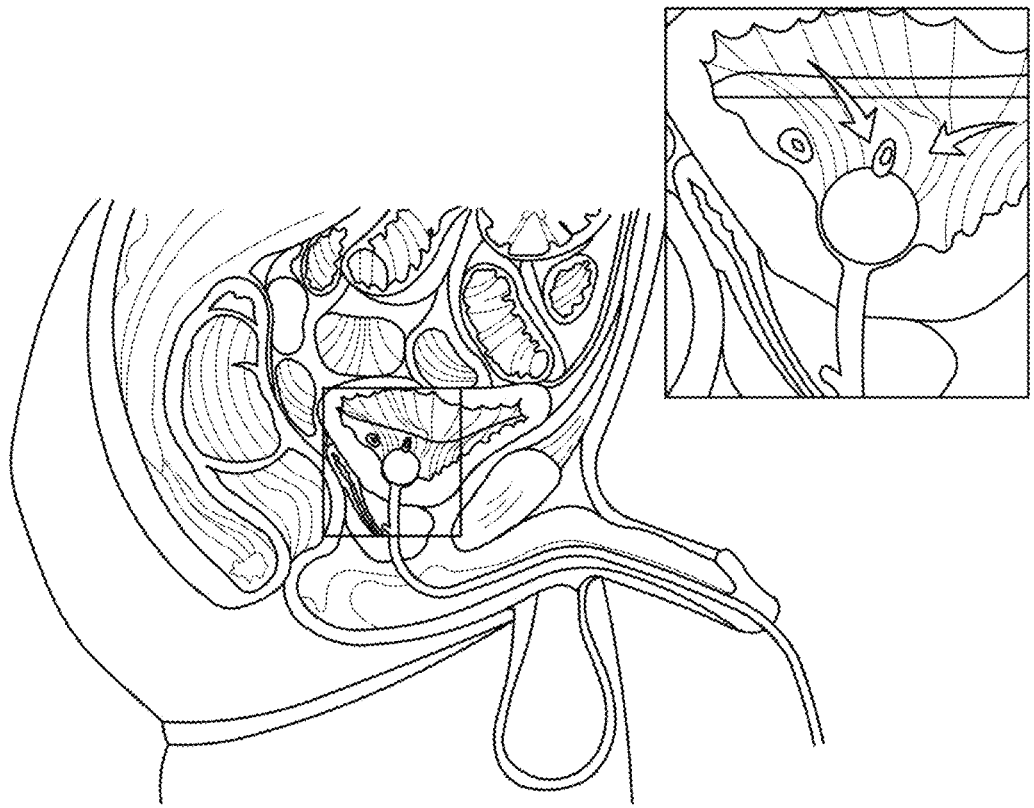
Figure 5:
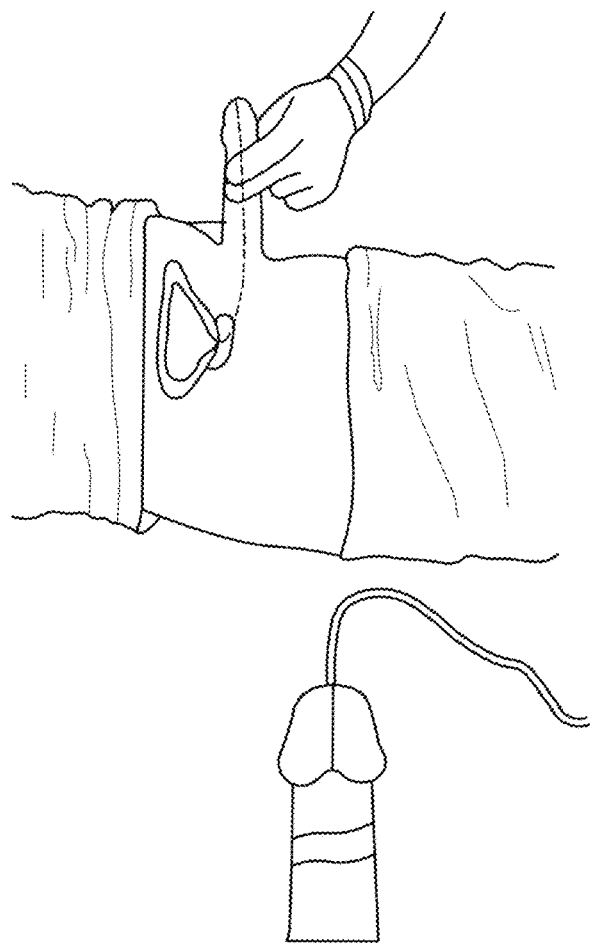
FIG. 5 illustrates one embodiment of a flexible body fluid movement system.

As illustrated in FIGS. 1-4 and 5, in one embodiment, a flexible body fluid drainage system 10 is provided that includes one or more a hollow, partially or fully flexible body fluid drainage apparatus tubes, generally 12, that can be a single tube, multiple tubes 12(a)-(c), with lumens that collect urine from the bladder and leads to a drainage bag 14. As a non-limiting example, drainage bag 14 can be expandable, flexible, be a urinary leg bag 14 with top and bottom leg attachments 15 that can be flexible, adjustable, and the like. In one embodiment, drainage bag 14 reduces fluid back pressure by avoiding the formation of dependent loops, and can include low aspect ratio collection receptacles that rest on a flat surface to improve fluid flows and/or minimize back-pressures exerted by collected fluids. Flexible body fluid drainage system 10 is kept in place by a bladder retention member (balloon) 17 that is deployed in the bladder in order to provide a retention of body fluid drainage system 10 in the bladder. In one embodiment a plurality of urinary leg bags can be utilized in place of adhesive pads attached to the skin.

In one embodiment, a urinary catheter 10 is provided with a catheter 10 with a urinary catheter tube with one or more lumens 12(a)-12(c), a proximal end 13, a distal end and a balloon 17 coupled to proximal end 13. Balloon 17 is configured to be positioned in an interior of a bladder. Proximal end 13 is configured to provide flow of urine from the bladder through the catheter lumen 12. Balloon 17 is configured to be deployed and anchor the distal end in an interior of the bladder, Drainage bag 14 is configured to receive urine from the bladder through the catheter lumen 12, Drainage bag 14 has an inlet port 22 for receiving urine from catheter lumen 12 and an outlet port 24 for draining urine from drainage bag 14. In one embodiment, drainage bag 14 is configured to drain urine while moving in a direction away from the leg. The drainage bag 14 includes at least one leg attachment 15 configured to couple the patient's leg with drainage bag 14. Urinary catheter tube 12 includes proximal end 13. Proximal end 13 has a plurality of urine draining holes 19 that receive urine from the bladder and allow it to be transported to and though urinary catheter tube 12 In one embodiment, urinary catheter tube 12 is made of a flexible material, or has one or more coiled sections that provide for drainage of at least a portion of the urinary catheter relative to the drainage bag 14. Urinary catheter tube 12 has outlet port 26 at the distal end of urinary catheter tube 12 coupled to the inlet port 22 of the drainage bag 14. Inlet port 22 of drainage bag 14 and the outlet port 26 of the urinary catheter tube 12 are both locked together by a locking mechanism 32 without a loop, a pleated or a corrugated segment. Locking mechanism 32 is not integrally formed as a part of drainage bag 14 or catheter 12. Locking mechanism 32 is a separate structure from drainage bag 14 or catheter 12. Locking mechanism 32 is positioned around and in at least a partial or full surrounding, circumferential relationship at an exterior of the inlet and outlet ports 22, 26 and at an exterior of drainage bag 14. In one embodiment, locking mechanism 32 is adjacent to drainage bag 14. Locking mechanism 32 provides a non-tensile compression force to both the outlet and inlet ports 26 and 22, allowing for longitudinal drainage of the outlet port 26, the inlet port 22 and the locking mechanism 32 when a patient's leg moves more than a predetermined distance. Locking mechanism 32 is usable with different drainage bags 14 and urinary catheters 16.

As a non-limiting example, the flexible body fluid drainage system is a catheter system 10; and the body fluid apparatus is a catheter 12.

In one embodiment, a urinary catheter 12 is provided with a catheter 12 with a urinary catheter tube with a lumen 12, a proximal end 13, a distal end and a balloon 17 coupled to the proximal end, the balloon 17 configured to be positioned in an interior of a bladder, the proximal end 13 configured to provide flow of urine from the bladder through the catheter lumen 12, the balloon 17 configured to be deployed and anchor the distal end in an interior of the bladder; a drainage bag is configured to receive urine from the bladder through the catheter lumen, the drainage bag has an inlet port 22 for receiving urine from the catheter lumen 12 and an outlet port 24 for draining urine from the drainage bag, the outlet port 26 of the drainage bag configured to drain urine while moving in a direction away from the leg, Drainage bag 14 includes at least one leg attachment 15 configured to couple a patient's leg with drainage bag 14, Catheter tube 12 includes the proximal end, the proximal end 13 having a plurality of urine draining holes that receive urine from the bladder and allow it to be transported to and though the urinary catheter tube, the urinary catheter tube being made of a flexible material, or including one or more coiled sections that provide for drainage of at least a portion of the urinary catheter relative to the drainage bag, the urinary catheter tube having the outlet port 26 at the distal end of the urinary catheter tube coupled to the inlet port 22 of the drainage bag; and the inlet port 22 of the drainage bag and the outlet port 26 of the urinary catheter tube are both locked together by a locking mechanism 32 without a loop, a pleated or a corrugated segment and is not integrally formed as a part of the drainage bag or the catheter. In one embodiment, locking mechanism 32 is positioned around and in a surround relationship at an exterior of the inlet and outlet ports 22 and 26 at an exterior of the drainage bag 14 and adjacent to the draining bag 14, providing a non-tensile compression force to both the outlet and inlet ports 26 and 22 allowing for longitudinal drainage of the outlet port, the inlet port 26, 22 and locking mechanism when a patient's leg moves more than a predetermined distance, the locking mechanism 32 is usable with different drain bags and urinary catheters.

FIGS. 5B and 5C illustrate embodiments of locking mechanism 32 providing a non-tensile, compression force to both inlet port 22 of drainage bag 14 and the outlet port 26 of catheter lumen 12, FIG. 5B is an exploded view, showing that the interior of either inlet port 22 or outlet port 26 receives the other in an interior thereof. Locking mechanism 32 completely surrounds or at least partially surrounds both ports 22 or 26, in a circumferential manner. As a non-limiting example, locking mechanism 32 is positioned adjacent to either port 22 or 26, and the other port is in an interior thereof. In either configuration, locking mechanism 32 provides the compression force directly to the exterior port, and indirectly to the port positioned in an interior thereof.

In various embodiments, locking mechanism 32 is positioned externally and circumferentially around ports 22 or 26 to supply sufficient force so that the ports 22 and 26 to prevent urine or other body fluid leakage. This provides the ports 22 and 26 remain coupled together, partially when a patient moves, such as when a patient's leg moves. In one embodiment, locking mechanism can be 50% or more, 75% or more, 90% or more 95% or more, 100% in a surrounding, circumferential relationship to the exteriors of ports 22 and 26. In various embodiment, locking mechanism 32 is adjustable to provide the correct amount of compression force so ports 22 and 26 such that this leaking and coupling is provided. Locking mechanism 32 can be adjustable, in order to vary the amount of compression force applied to ports 22 and 26. This can be achieved by adjusting the length, circumference, geometry to locking device 32. This can also be achieved by including an adjustment device, including but not limited to an adjuster, a locking mechanism sizer, to locking mechanism 32, and the like. Additionally, spring inserts, horseshoe-shaped inserts. sizing beads and the lick can be included as well as plastic adjusters, silicon adjusters, Blulu adjusters, Likemar adjusters, memory materials, and the like.

In one embodiment, body fluid drainage system 10 includes a single flexible body fluid drainage apparatus tube 12, multiple flexible body fluid drainage tubes 12(a)-(c). In one embodiment, flexible body fluid drainage apparatus tubes 12, 12(a)-(c) can be made of a stretched thermoplastic material. The thermoplastic material can be extrudable. As a non-limiting example, the thermoplastic material can be (a) from 40 to 70 percent by weight of an elastic composition which comprises: from 50 to 99.5 percent by weight of a block copolymer having thermoplastic rubber characteristics with a central, rubbery polyolefin block and terminal blocks of polystyrene, and optionally including up to about 45 percent by weight of polypropylene, plus from 0.5 to 10 percent by weight of a cross-linked organic silicone elastomer; and (b) from 30 to 60 percent by weight of a hydrophobic oil-type plasticizer to provide the desired degree of softness to said elastic composition.

Figure 6:
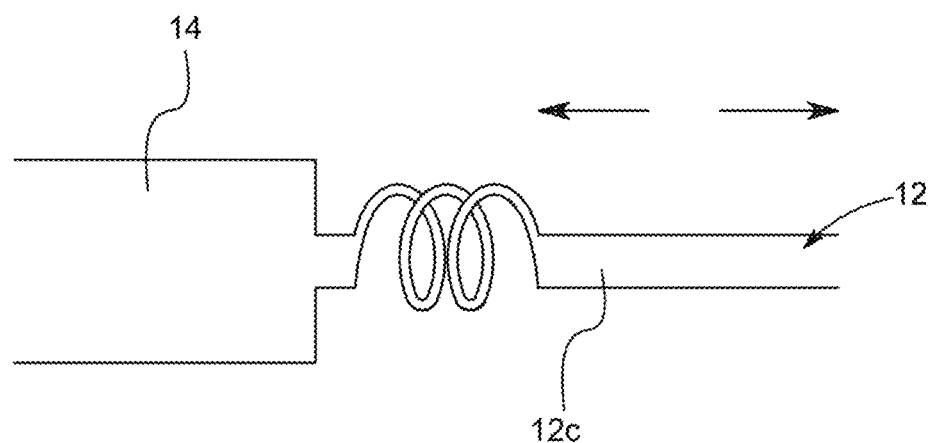
FIG. 6 illustrates one embodiment of a flexible body fluid movement system partially or wholly coiled to provided additional body fluid movement system length that is stretchable to provide movement.
Figure 7:
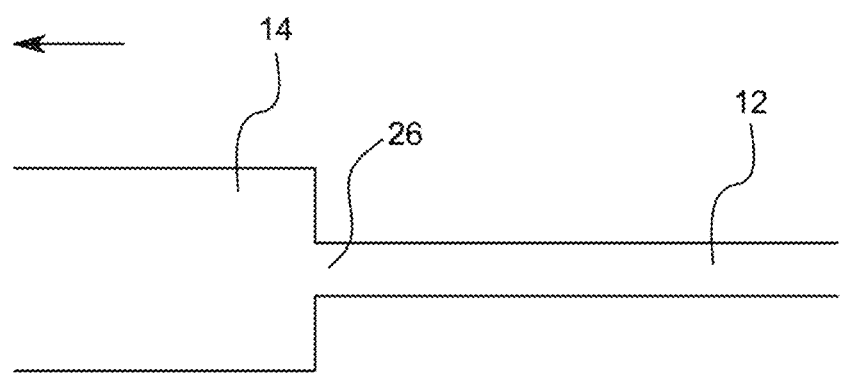
FIG. 7 illustrates one embodiment of a flexible body fluid movement system made of a suitable material that is able to stretch when drainage bag moves in directions towards or away a drainage bag.

In one embodiment, all or a portion, particularly the end section of flexible body fluid movement apparatus 12 and/or 12(c) can be partially or wholly coiled to provided additional body fluid movement length that is stretchable to provide movement, see FIG. 6. The coiled portion can readily extend and contract to relieve tension on the body fluid movement 10. In one embodiment, flexible body fluid movement apparatus tube, 12(a)-(c) is movable with respect to drain bag 14, see FIG. 6. As a non-limiting example, distal end of 12(c) can be coupled to drainage bag inlet port 22 with a flexible, expandable outlet port 26. All or all of a portion of urinary body fluid movement 10, and the like and also made of a suitable material that is able to stretch when drainage bag moves in directions towards or away from outlet port 26, see FIG. 7.

Common indications for placing a urinary flexible body fluid movement in a patient include: (i) acute or chronic urinary retention, both mechanical such as in the case of benign prostatic hypertrophy or non-mechanical such as in spastic bladder neck; (ii) the need to measure the urine output in critical care patients; (iii) incontinence; and (iv) patients post bladder or gynecological surgery.

Figures 8, 9:
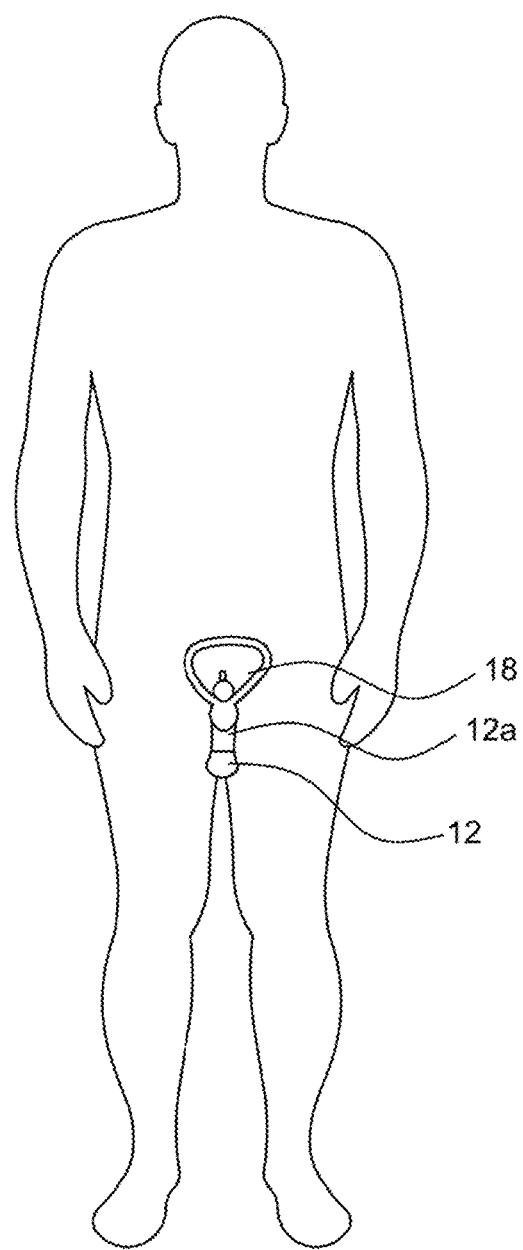
FIGS. 8 and 9 illustrate a proximal flexible body fluid movement system tube is inserted into a patient

As illustrated in FIGS. 8 and 9, in one embodiment, proximal flexible body fluid movement apparatus tube (a) is inserted into a patient, in this embodiment, the penis, which can be held at a selected angle, for example 90 degrees. Body fluid movement apparatus 12(a) or a single flexible body fluid tube is advanced into the patient's urinary meatus. There may be resistance at the urethral sphincter or the prostate. It is recommended that the advancement be paused to allow the sphincter to relax. The penis is then lower and the flexible body fluid movement apparatus tube 12(a) continues to advance.

Body fluid movement system 10 can be: an indwelling body fluid movement system 10; a condom body fluid movement system 10; intermittent self-body fluid movement system 10 and the like. Dimensions of body fluid movement system 10 can be 10 Fr (3.3 mm) to 30 Fr (10 mm), and color-coded by size and have a solid color band on the outer end of the bladder retention member for easy size identification. Size 12 Fr is large enough to relieve urinary obstruction in most adults, although practitioners typically choose size 14 to 16 Fr for initial body fluid movement system 10. As a non-limiting example, suitable dimensions of body fluid movement 10, more particularly of flexible body fluid movement tubes 12 can be as follows:

| Color | Size French | Size in Millimeter |
| --- | --- | --- |
| Light Green | 6 | 2.0 mm |
| Light Blue | 8 | 2.7 mm |
| Black | 10 | 3.3 mm |
| White | 12 | 4.0 mm |
| Green | 14 | 4.7 mm |
| Orange | 16 | 5.3 mm |
| Red | 18 | 6.0 mm |
| Yellow | 20 | 6.7 mm |
| Purple | 22 | 7.3 mm |
| Blue | 24 | 8.0 mm |
| Black | 26 | 8.7 mm |

Figure 10:
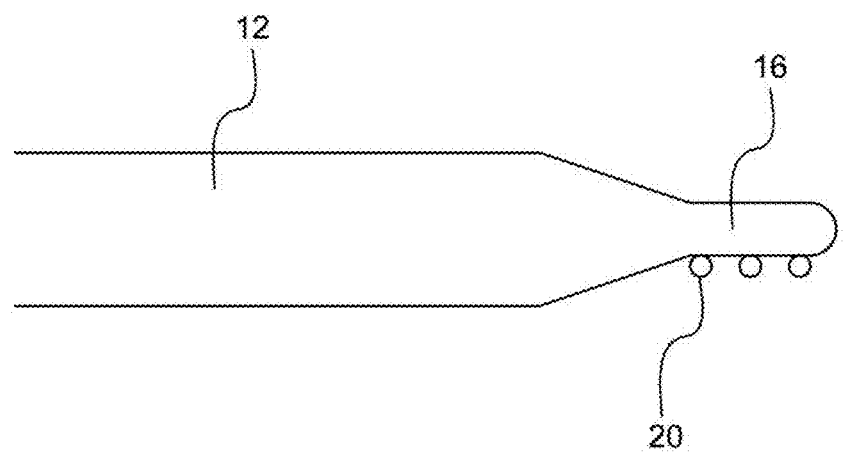
FIG. 10 illustrates one embodiment of insertion of a proximal end of a flexible body fluid movement system inserted into the urethra to reach the bladder.

In one embodiment a flexible body fluid movement system 10 is provided. Flexible body fluid movement system 10 can include an insertion tip 16, FIG. 10, that is advanced by a patient's urethra. In one embodiment, insertion tip 16 is a narrow proximal end 13 of flexible body fluid movement system 10 that inserts into the urethra to reach the bladder 18. Insertion tip 16 includes one or more draining holes/eyelets 20 in that receive fluids, including urine, from the bladder 18. Draining holes 20 are small holes in proximal flexible body fluid movement apparatus tube 12, which are positioned on or very near insertion tip 16 to make urine draining easy. Flexible body fluid movement apparatus drainage holes 20 are sometimes referred to as drainage holes or flexible body fluid movement apparatus eyes 20

Figure 11:
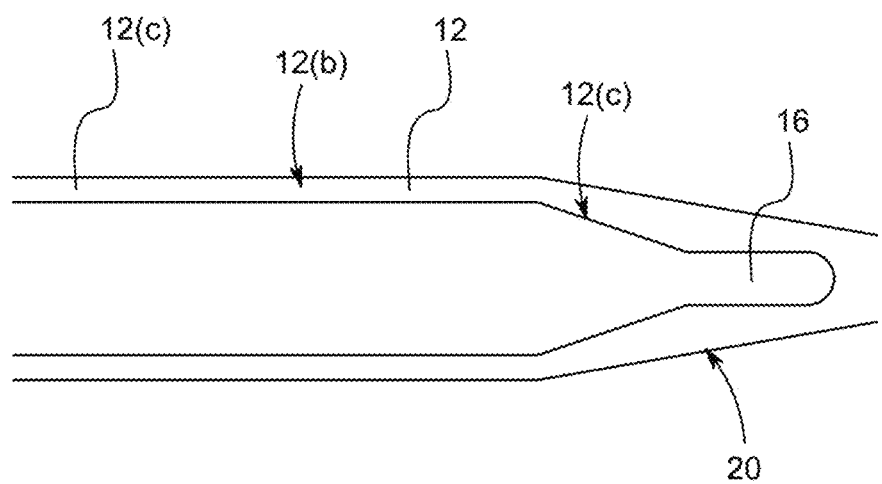
FIG. 11 illustrates a flexible body fluid movement system with only one tube extending from the bladder to the drainage bag.
Figure 12:
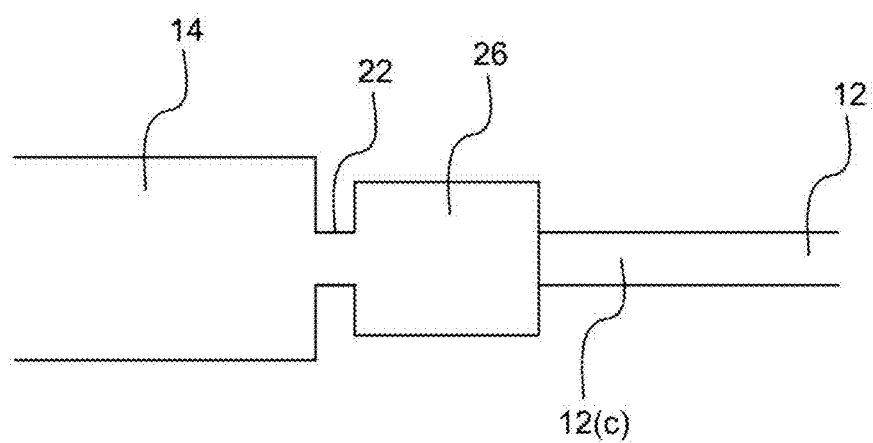
FIG. 12 illustrates an outlet port sufficiently coupled to the inlet so that the two remain coupled when body fluid movement system moves or drain bag moves.

As illustrated in FIG. 11, a first flexible body fluid movement apparatus tube 12(a), with lumen is provided. In various embodiments a plurality of flexible body fluid movement apparatus tubes 12(a)-(c), with lumens, are included and can have one or more intermediate flexible body fluid movement apparatus tubes 12(b) with lumens, a distal flexible body fluid movement apparatus tube 12(c) with lumen and the like. Flexible body fluid movement system 10 can have only one flexible body fluid movement apparatus tube 12, extend from the bladder 18 to drainage bag 14. It will be appreciated that all body fluid movement apparatus tubes can be flexible, expandable, moveable, and the like. Flexibility reduces the occurrence of a body fluid movement apparatus tube 12 from being in a kinked, non-flowing positioned, obstructed, and bent as to restrict urine flow Drain bag 14 includes an inlet port 22 for coupling/attaching to a distal end of flexible distal body fluid movement apparatus 12(c). Drain bag 14 also includes a drainage outlet port 24 for draining collected urine and the like from drainage bag 12. Distal end of flexible distal body fluid movement apparatus 12(c) includes an outlet port 26 to couples to inlet port 22. Outlet port 26 is sufficiently coupled to inlet port 22 so that the two remain coupled when body fluid movement system 10 moves or drain bag moves, FIG. 12. They do not become disconnected from a patient's body motion and/or movement. This is more fully discussed below.

In one embodiment, flexible body fluid movement system 10 can be a straight intermittent flexible body fluid movement system 10, a closed system flexible body fluid movement kit, and the like. As a non-limiting example, flexible body fluid movement system 10 can have a variety of insertion tips 16, such as a straight tip, a crude tip and the like. The decision as to the type of insertion tip 12 to use is often made by the physician, the physician and patient, the nurse, physician's assistant, caregiver and the like. Insertion tip 16 can be at one end of first flexible body fluid movement apparatus tubes with lumens 12(a)-12(c) can be flexible and/or include a spiral. As a non-limiting example, flexible body fluid movement system 10 can include only the first tubes 12 with a lumen extending from the bladder to the draining bag 14. Flexible body fluid movement apparatus tubes 12(a)-(c), with lumens, as well as lumen 12 can be made of a variety of materials, including but not limited to: assorted polymers, polymer-metal composites polyamide (nylon), polyether block amide, polyurethane, polyethylene terephthalate, and polyimides.

In one embodiment, flexible body fluid movement apparatus tubes 12, which can be 12(a)-(c) can be coated or impregnated with a variety of materials 29 for various purposes including but not limited to materials that provide: protect against infection, case the discomfort of insertion, and the like. As a non-limiting example, tubes 12(a)-(c) can include one or more lumens inside and outside lumen walls. These walls ben be coated or impregnated on the inside and outside lumen walls with biomimetic surface 29 to prevent bacterial or other microbial growth. In another embodiment, the surfaces of the tubes 12 and/or lumen walls impregnated and/or coated with antibiotics, antibacterial or coated with biocompatible materials that prevent bacterial overgrowth, such as silver or copper.

Figure 13:
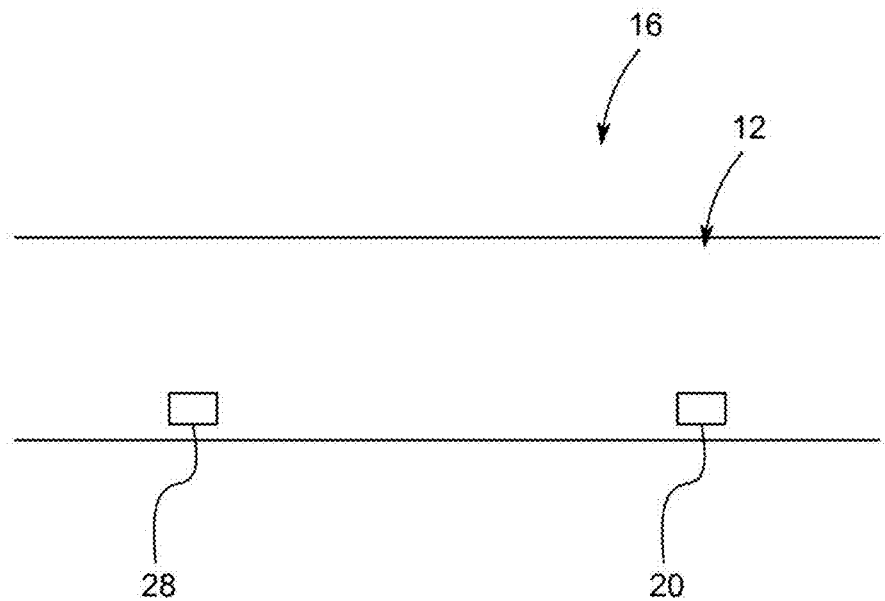
FIG. 13 illustrates a body fluid movement system with one or more sensors

In one embodiment, body fluid movement system 10 includes one or more sensors 28, FIG. 13.

In one embodiment, an introducer can be used to facilitate insertion of body fluid movement system 10 into the urinary tract.

In one embodiment, flexible body fluid movement system 10 is made more comfortable. This can be achieved by polishing and recessing drainage holes 20, which can reduce friction and irritation in the delicate urethral tissues. As a non-limiting example, flexible body fluid movement apparatus tubes 12 can be silicone-elastomer, coated after insertion, and the like.

Figure 14:
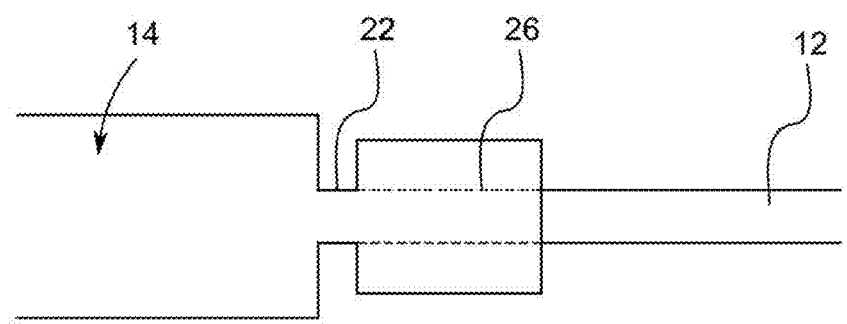
FIG. 14 illustrates inlet and outlet ports remaining coupled irrespective of body movement.

As previously stated, and as illustrated in FIG. 14, inlet and outlet ports 22 and 26 remain coupled irrespective of body movement. An infusion cleaning port 30 for cleaning distal end of flexible body fluid movement apparatus 12(c) for can included.

Figure 15:
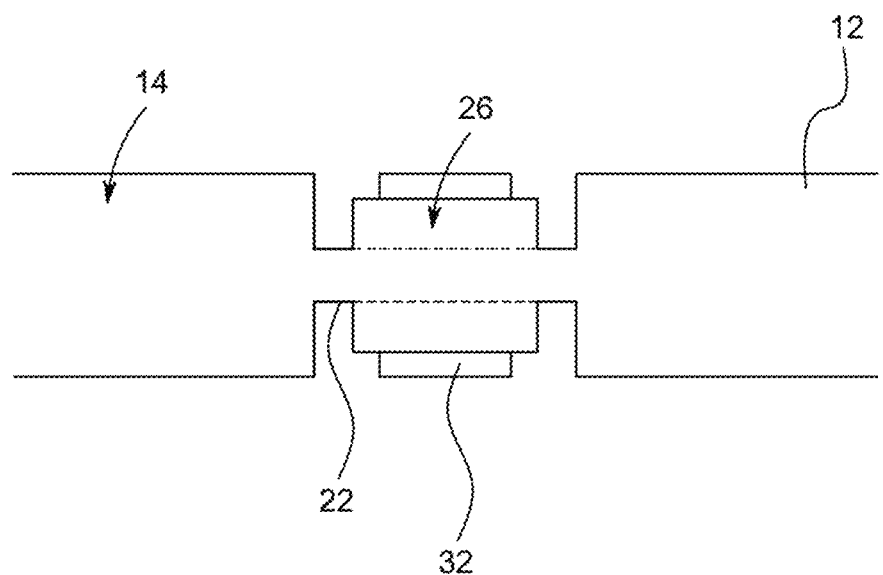
FIG. 15 illustrates an embodiment with two ports with a locking mechanism.

In one embodiment, ports 22 and 26 remain in a locked engagement and can have a locking mechanism 32, FIG. 15, positioned around exteriors or interiors of outlet ports 24 and 26. This provides a closed system with a locking/tight/secure mechanism 32 that couples a urinary body fluid movement system 10 to attach/detach with drain bag 14.

Figure 16A:
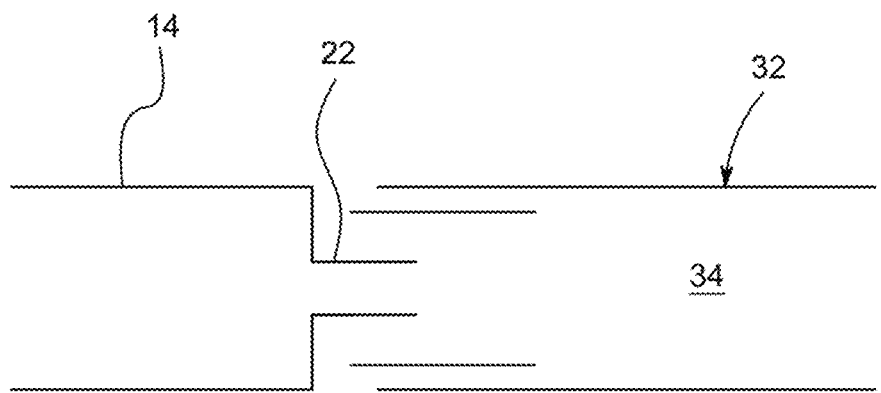
FIG. 16A illustrates inlet and outlet ports each have a plurality of ridges that engage with each other to provide a locking arrangement.

In one embodiment, locking mechanism 32 provides a compression force to outlet ports 24 and 26, but still allows passage of the fluid, urine, into drain bag 14. A variety of locking mechanisms 32 can be used including but not limited to: a bore connector, a series-to-twist coupling, (SMC), luer, SMC connector that allows rotation and movement and prevents kinking, one or more series twist-to-connect couplings, twist lock, swivel-snap connectors, locking connectors, windings, brackets, flip locks, lockout locks, pop locks, telescopic tube locks, Locking & telescoping mechanisms for composite tubes Flip lock clamps & twist lock rings Button clips & ball lock pins, push button telescoping tube locks, telescoping tube clamps around telescoping tubing locks, tubular locks, micro-tube cap locks, telescoping tube adjusters, pin clips, lock nuts, and the like. As illustrated in FIG. 16A, in one embodiment, a hollow pipe 32 and a group of telescopic sleeves 34 are used for coupled. The telescopic tube can be a fixed sleeve fixedly arranged at an end part of the closed first end of the hollow tube to communicate the inner cavity of the hollow tube with the outside, and a sliding sleeve which is sleeved with the fixed sleeve in a sliding manner.

As a non-limiting example, locking mechanism 32 can be a twist-lock 32, snap-lock 32, luer-lock 32, clamp-lock 32 and the like.

Figure 16B:
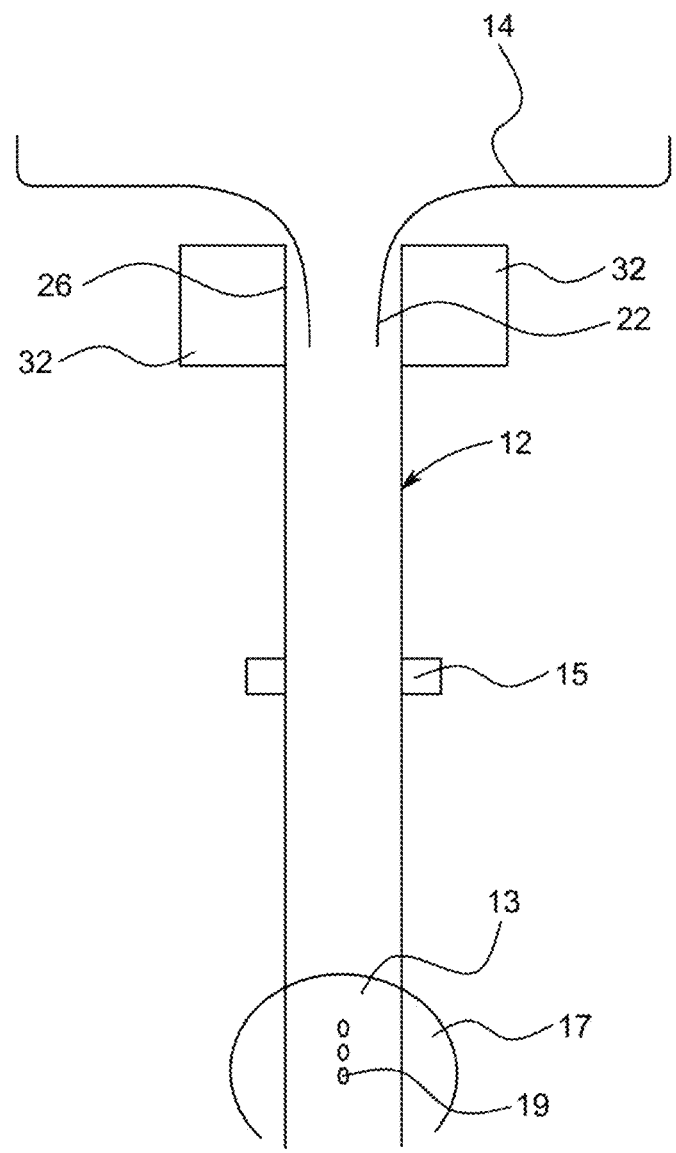
FIGS. 16B and 16C illustrates various embodiments of the locking mechanism.

As a non-limiting example, illustrated in FIG. 16B a body fluid movement system 10 is provided with a body fluid movement apparatus 12 with one or more tubes and lumens, a proximal end 13, a distal end and a balloon 17 coupled to the proximal end. The balloon 17 is configured to be positioned in an interior of the bladder, the proximal end 13 is configured to provide flow a body fluid from the bladder through the body fluid movement apparatus 12. Balloon 17 is configured to be deployed and anchor the proximal end 13 in an interior of the bladder. Drainage bag 14 is configured to receive urine from the bladder through the body fluid movement apparatus lumen(s) 12. Drainage bag 14 has an inlet port 22 for receiving urine from catheter lumen 12 and an outlet port 24 for draining urine from drainage bag 14. In one embodiment, drainage bag 14 is configured to drain urine while moving in a direction away from a patient's leg. The drainage bag 14 includes at least one leg attachment 15 configured to couple the patient's leg with drainage bag 14. Body fluid movement apparatus 12 includes proximal end 13. The proximal end 13 has a plurality of urine draining holes 19 that receive urine from the bladder and allow it to be transported to and though the body fluid movement apparatus, and tubes 12. In one embodiment, body fluid body fluid movement apparatus tube(s) 12 can be made of a flexible material, or includes one or more coiled sections that provide for drainage of at least a portion of the body fluid movement apparatus relative to drainage bag 14. Body fluid movement tube 12 has an outlet port 26 at the distal end of body fluid movement apparatus tube 12. The outlet port 26 is coupled to the inlet port 22 of the drainage bag 14. Inlet port 22 of drainage bag 14 and the outlet port 26 of body fluid movement apparatus tube 12 are both locked together by a locking mechanism 32, without a loop, a pleated or a corrugated segment. Locking mechanism 32 is not integrally formed as a part of drainage bag 14 or body fluid movement apparatus 12. Locking mechanism 32 is a separate structure from drainage bag 14 or body fluid movement apparatus 12. Locking mechanism 32 is positioned around and in a surrounding relationship at an exterior of the inlet and outlet ports 22, 26 and at an exterior of drainage bag 14. In one embodiment, locking mechanism 32 is adjacent to drainage bag 14. In one embodiment, locking mechanism 32 provides a non-tensile, compression force to both the outlet and inlet ports 26 and 22, allowing for longitudinal drainage of the outlet port 26, the inlet port 22 and the locking mechanism 32 when a patient's leg moves more than a predetermined distance. Locking mechanism 32 is usable with different drainage bags 14 and urinary catheters 16.

Figure 16C:
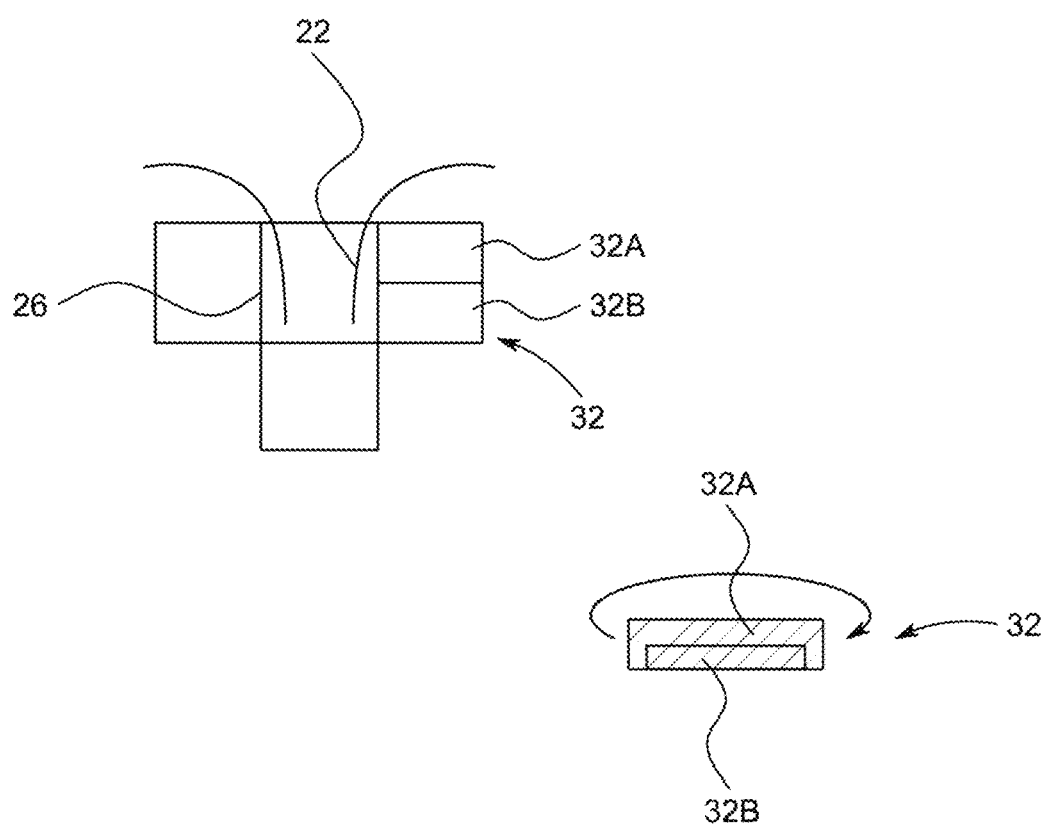

In one embodiment, FIG. 16C locking mechanism 32 includes a twist-lock mechanism, positioned around and in a surrounding relationship at an exterior of the inlet and outlet ports 22, 26, and at an exterior of drainage bag 14. In one embodiment, the inlet port 22 extends a small distance of 0.5 to 2 inches from the body of drainage bag 14. In one embodiment, inlet port 22 is in an area that does not extend from the physical body of drainage bag 14. In one embodiment, locking mechanism 32 includes inner and outer wall that engages, and/or pressed together, provides a compression around exterior of inlet and outlet ports 22 and 26. The locking mechanism 32 is a separate structure or part from and not included in inlet or outlet ports 22 and 26. In various embodiments when pressed together, locking mechanism 32 provides a compression of its the inner wall 32a against its outer walls 32b, relative to inlet and outlet ports 22, and 26. This provides a leak free connection. In one embodiment, locking mechanism 32 includes a male fitting 32a with ribs, tabs, and/or threads that couple with a female fitting 32b with ribs, tabs, and/or threads. In one embodiment the male fitting and the female fitting are rotatable with respect to each other. The two male and female fittings 32a an 32b can also be pressed together to lock, rotatable clockwise and counterclockwise to attach and detach from In various embodiments, locking mechanism 32 can be formed of any desired material, giving the locking mechanism 32 a desired amount of flexibility and/or compressibility. Locking mechanism 32 can be formed of silicone or other flexible polymeric material. Silicone provides rubber-like properties and can frictionally engage ports 22 and 26 with compression without interrupting the flow of urine. As a non-limiting example, locking mechanism 32 is coated with a material having a high coefficient of friction to enhance the frictional engagement.

In one embodiment, locking mechanism 32 can be in a first position in which the flexible body fluid movement apparatus distal tube 12(c) is free to move longitudinally via locking mechanism 32. This movement apparatus reduces the chance that body fluid movement apparatus distal tube 12(c) disengages from inlet port 22 of drain bag 14. In one embodiment, locking mechanism 32 can move to a second position in body fluid movement apparatus distal tube 12(c). allowing movement, and produces less stress on its engagement with drain bag 14.

Figure 17:
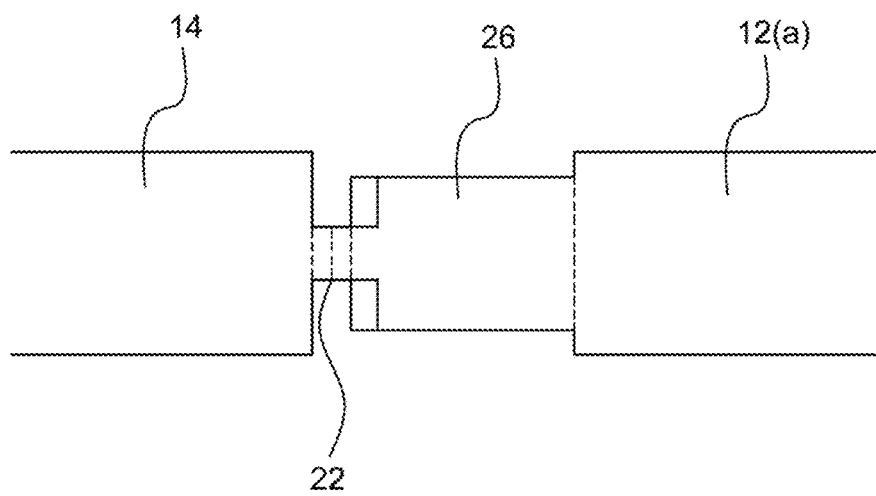
FIG. 17 illustrates the inlet and output ports each having windings similar to a screw.

In one embodiment, illustrated in FIG. 17 inlet port 22 and outlet port 26 each have a plurality of ridges that engage with each other to provide a locking arrangement. In another embodiment, illustrated in FIG. 17, inlet port 22 and outlet port 26 each have a plurality of windings, such as in a screw, and are coupled together with engagement of the windings. In other embodiments, the drain bag 14 is locked to body fluid movement apparatus distal tube 12(c) with bends notches, recesses, and the like.

As a non-limiting example, an improved locking mechanism 32 is provided that prevents leaks of urine, is easy for a patient or care giver to use, is compatible a variety of different drain bags 14 and urinary body fluid movement system 10 and the like. In one embodiment, locking mechanism 32 is positioned at a place at drain bag 14 so as not to cause any irritation to the patient's skin. Locking mechanism 32 can have a configuration that is substantially smooth, without any rough edges. Locking mechanism 32 can be made of the same material as tube 12(c).

As a non-limiting example, locking mechanism 32 can be a two-step lock 32 to provide greater engagement between urinary body fluid movement apparatus 12 and drain bag 14. This results in a reduction and/or elimination of urine leakage. In one embodiment, a connector 33 is used to couple and/or insert, urinary body fluid movement apparatus 12 into drain bag 14. In a second step, body fluid movement apparatus 12 then engagers with connector 18 to lock in place, as illustrated in FIG. 18 This is done by using locking mechanism 32 that ensures urinary body fluid movement apparatus 12 does become disconnected from drain bag 14, partially when the patient moves.

Figure 18:
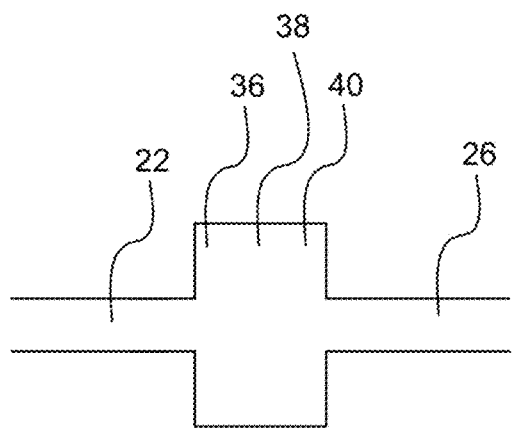
FIG. 18 illustrates a two-step locking mechanism, with a connector and lock.

In various embodiment, FIG. 18, locking mechanism can be a twist-lock 36, snap-lock 38, clamp-lock 40, luer lock 42, and the like. Twist-lock 36 is configured to prevent over-twisting, and under-twisting when locking, and no or little damage to connector 33 and tube 12(c), more particularly inlet port 22 and outlet port 26 Under-tightening results in inadequate coupling, and causes leaking.

Figure 19A:
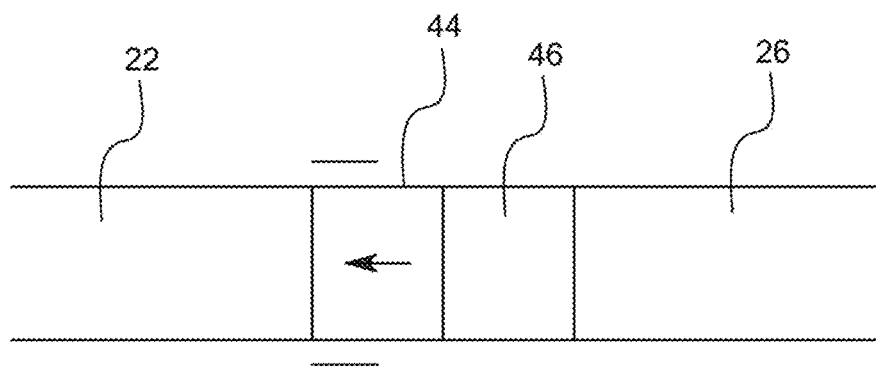
FIGS. 19A-19B illustrate one embodiment of a twist-lock, with male and female connectors.
Figure 19B:
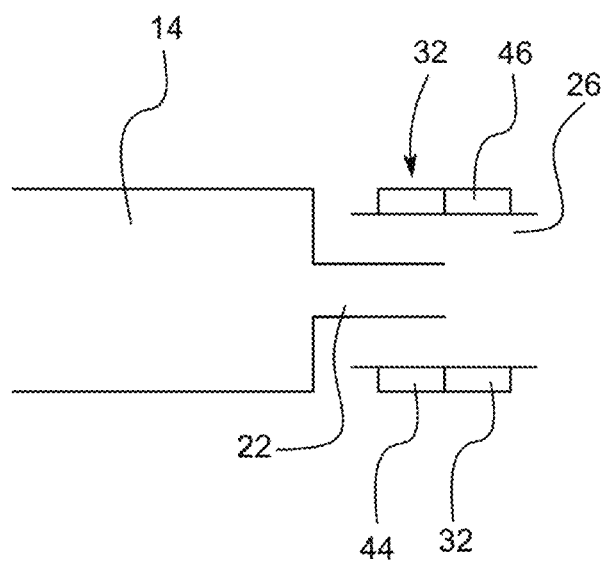

FIGS. 19A-19B illustrate one embodiment of a twist-lock 32, with male and female connectors 44 and 46. Male connector 44 has a threaded end that is inserted into female connector 46. Connectors 44 and 46 and then twisted together. This creates a seal.

Figure 20:
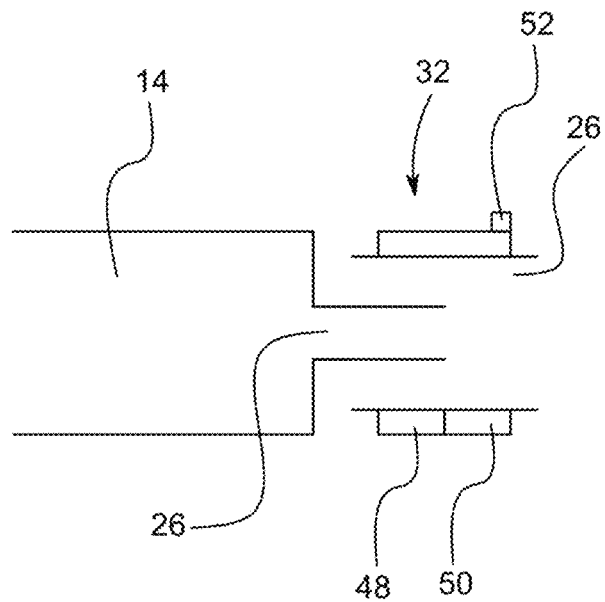
FIG. 20 illustrates one embodiment of a snap-lock includes male and female connectors.

As illustrated in FIG. 20, snap-lock 32 includes male and female connectors 48 and 50. Male connector 48 has a protruding tab or button 52 that snaps into a corresponding slot of female connector 50. Connectors 48 and 50 are pushed together until tab or button 52 snaps, creating a seal.

Figure 21:
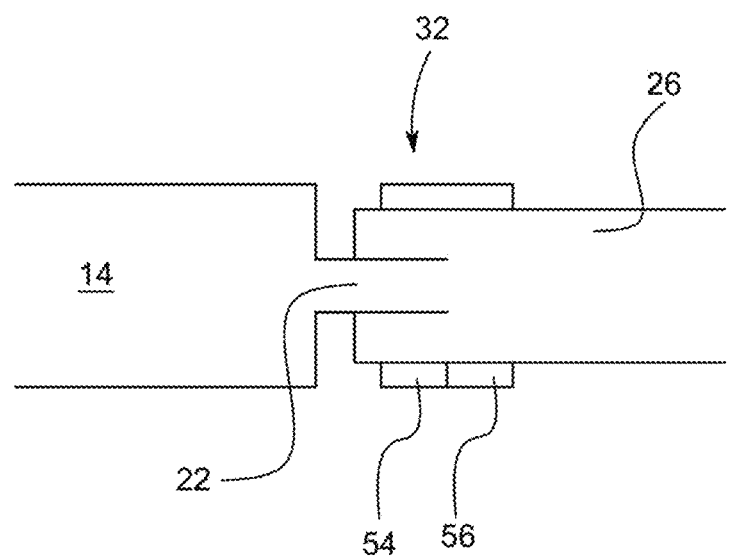
FIG. 21 illustrates one embodiment of a luer lock.

Referring to FIG. 21, luer-lock 32 includes male and female connectors 54 and 56, Female connector 56 has a tapered opening with threads that match those on male connector 54. The threads secure connectors 54 and 56, creating a seal.

Figure 22:
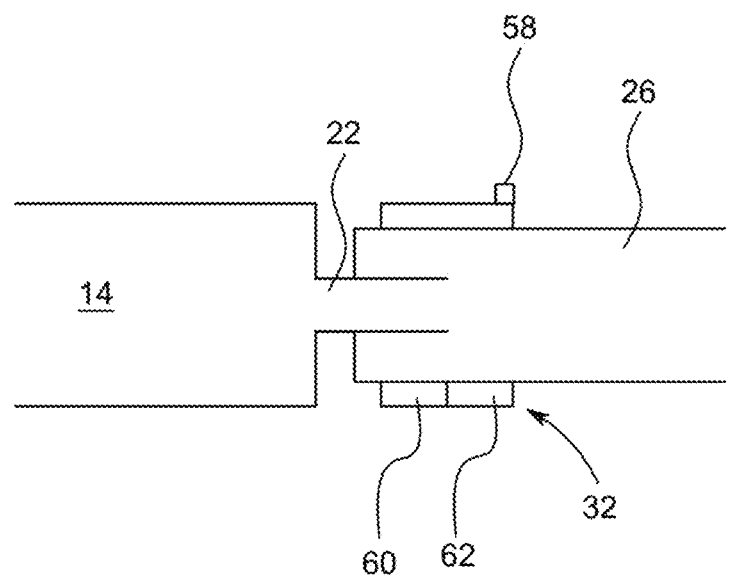
FIG. 22 illustrates one embodiment of a clamp lock.

As illustrated in FIG. 22, clamp lock 32 includes male and female connectors 58 and 60. Male connector 58 is inserted into female connector 60. Male connector 58 can include a tapered end. A sliding mechanism 62 is used for the coupling, created a seal.

Locking mechanism 32 can be added to an existing body fluid movement apparatus 12, or be a part of body fluid movement apparatus 12.

Figure 23:
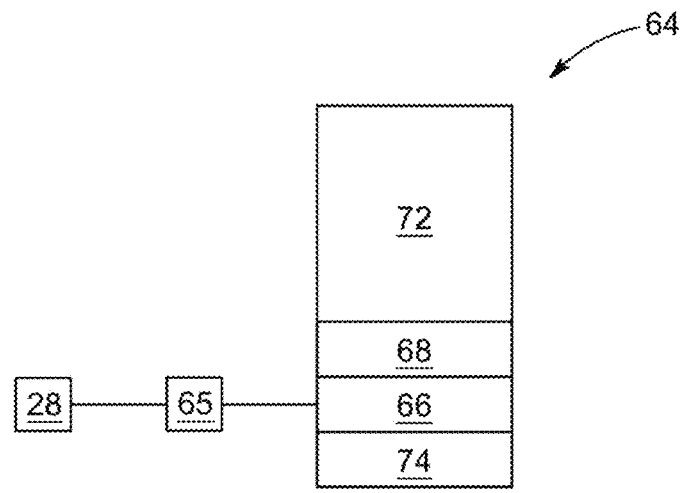
FIGS. 23 and 24 illustrate one embodiment of an AI system used with the body fluid movement system.
Figure 24:
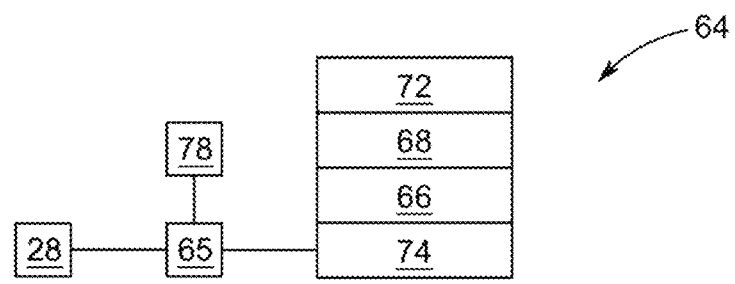

In various embodiments, systems system 10 can use AI (AI), as illustrated in FIGS. 23 and 24. Examples of AI used include but are not limited to including linear regression, logistic regression, decision tree. SVM algorithm, Naive Bayes algorithm, KNN algorithm. K-means, random forest algorithm, dimensionality reduction, and the like.

As a non-limiting example, a k-means algorithm is used.
The one or more sensors 28 can be used for urine analysis data/information received from one or more sensors 28. The one or more sensors 28 can be used to test and monitor urine to check a patient's overall health. The one or more sensors 28 can be used for urinalysis that is part of a routine medical exam, pregnancy checkup or pre-surgery preparation, and the like.

As non-limiting examples, the one or more sensors 28 can diagnose a medical condition, monitor a medical condition and the like.

It can help screen conditions related to kidneys and urinary tract. The test may be a diagnostic aid in dehydration, urinary tract infections, disorders of the urinary tract, kidney and metabolic disorders, cancers of kidneys and adjacent structures, etc. Kidney function and response to treatment may be monitored with the test. It is also used to diagnose and monitor the progression of diabetes. Urinalysis may also be advised before hospital admission and surgeries. A urine test can help assess a new pregnancy Urine monitoring with the one or more sensors 28 can be used for one or more of:

Urine pH level test: A urine pH test measures the acid-base (pH) level in your urine. A high urine pH may indicate conditions including kidney issues and a urinary tract infection (UTI). A low urine pH may indicate conditions including diabetes-related ketoacidosis and diarrhea.

Ketones urine test: Ketones build up when your body has to break down fats and fatty acids to use as fuel for energy. This is most likely to happen if your body does not get enough sugar or carbohydrates as fuel. Healthcare providers most often use ketone urine tests to check for diabetes-related ketoacidosis.

Glucose urine test: A glucose urine test measures the amount of sugar (glucose) in your urine. Under regular circumstances, there should not be glucose in your urine, so the presence of glucose could be a sign of diabetes or gestational diabetes.

Bilirubin urine test: Bilirubin is a yellowish pigment found in bile; a fluid produced by your liver. Bilirubin in urine, can indicate liver or bile duct issues.

Nitrite urine test: A positive nitrite test result can indicate a urinary tract infection (UTI). However, not all bacteria are capable of converting nitrate (a substance that is normally in your urine) to nitrite, so you can still have a UTI despite a negative nitrite test.

Leukocyte esterase urine test: Leukocyte esterase is an enzyme that is present in most white blood cells. When this test is positive, it may indicate that there's inflammation in your urinary tract or kidneys. The most common cause for white blood cells in urine is a bacterial urinary tract infection (UTI).

Urine specific gravity test: A specific gravity test shows the concentration of all chemical particles in your urine. Abnormal results may indicate several different health conditions.

Microscopic tests that providers may include in a urinalysis include:

Red blood cell (RBC) urine test: An elevated number of RBCs indicates that there's blood in your urine. However, this test cannot identify where the blood is coming from. For example, contamination with blood from hemorrhoids or vaginal bleeding cannot be distinguished from a bleed somewhere in your urinary system. In some cases, higher-than-normal levels of red blood cells in your urine may indicate bladder, kidney or urinary tract issues.

White blood cell (WBC) urine test: An increased number of WBCs and/or a positive test for leukocyte esterase may indicate an infection or inflammation somewhere in your urinary tract.

Epithelial cells: Epithelial cells are cells that form the covering on all internal and external surfaces of your body and line body cavities and hollow organs. Your urinary tract is lined with epithelial cells. It is normal to have some epithelial cells in your urine, but elevated numbers of epithelial cells may indicate infection, inflammation and/or cancer in your urinary tract.

Bacteria, yeast and parasites: Sometimes, bacteria can enter your urethra and urinary tract, causing a urinary tract infection (UTI). The urine sample can also become contaminated with bacteria, yeast and parasites, especially for people with a vagina. Yeast can contaminate the sample for people who have a vaginal yeast infection. *Trichomonas vaginalis* is a parasite that may also be found in the urine of people who have a vagina. It is the cause of an STI called trichomoniasis.

Urinary casts: Casts are tiny tube-like particles that can sometimes be in your urine. They are formed from protein released by your kidney cells. Certain types of casts may indicate kidney issues, while others are completely normal.

In addition, an inside wall of an inner lumen can be coated with a material that has low friction to enhance urine flow. This material can include but is not limited to: plastic, PET, a naturally occurring latex, or synthetic latex material. As a non-limiting example, outer surface of tubes 12 can be coated with a material designed to reduce friction so that body fluid movement system 10 can be inserted easily without undue force or trauma to the urethra or the bladder or any other body part. In one embodiment, the tube lumens can be coated on the outer surface with a material that enhances mucosal growth.

In various embodiments AI is used with information derived from the one or more sensors 28. The one or more sensors 28 convert biomedical parameters into easily measurable signals such as electricity and light, and can be divided into off-body detection and near-body monitoring. Off-body detection is mainly performed by medical liquid one or more sensors 28, gas sensors 28, and imaging devices to detect body fluids (blood, saliva, urine, etc.), exhaled breath, and medical images for the efficiency and accuracy improvements of disease diagnosis. Near-body monitoring creates new opportunities for telemedicine and continuous monitoring mainly through wearable devices worn directly on the skin of different body parts to collect key information about the wearer's health in a timely manner.

Due to the characteristics of continuity, minimally invasive, and multi-indicator, there are various application scenarios, including disease, motion, and mental status monitoring. To improve the efficiency and accuracy of medical sensor 28 diagnosis and treatment, AI algorithms have made extensive progress. Common algorithms currently include support vector machine (SVM), principal component analysis (PCA), decision tree (DT), long short-term memory (LSTM), artificial neural network (ANN), recurrent neural network (RNN), and convolutional neural network (CNN). The large amount of data obtained from sensing devices analyzed by AI algorithms can lead to more opportunities for proactive, modernized, and personalized medicine. Therefore, the combination of accurate sensor 28 and enhanced AI algorithms allows comprehensive information on disease characteristics through a sufficient number and variety of training samples. Systematic clinical assessment of health conditions can then be performed from multiple perspectives to improve the accuracy and efficiency of diagnosis.

Machine learning (ML) techniques can combine medical datasets from millions of patients, such as diagnostic profiles, imaging records, and wearable information, to analyze the internal structure of the ocean of medical big data, identify patterns of disease conditions, and overcome the general limitations on access to local datasets. Furthermore, the next-generation healthcare system supported by big data shifts from a centralized hospital-based mode to a parallel mode of monitoring at home, screening and detection at point-of-care testing (POCT), and monitoring during hospitalization, meanwhile, achieves doctor-patient interaction and data transferring via the cloud to ease healthcare resource crowding and facilitate personalized healthcare (FIG. 1). Ultimately, systematic health status assessment from comprehensive individual information is used for clinical applications to achieve improved data processing capabilities and resource optimization in healthcare. In this perspective, we present the latest advances in AI in clinical diagnosis from three perspectives on off-body detection, near-body monitoring, disease prediction and CDSS The challenges and opportunities of AI in personalized medicine in the future are deeply considered and discussed.

Referring to FIGS. 23 and 24, in one embodiment, a user can seek from system an artificial intelligence from the server and/or an artificial intelligence engine (AI) engine 65. In one embodiment, the artificial intelligence engine 65 make one or more of the following recommendations: offer access to medical specialists; improve communication and coordination of care among health care team members and a person getting care; offer advice for self-management of health care; uploading data to a wearer's health care team, including recommendations regarding exercise, types of food, when to eat when to exercise, blood sugar levels, how to modify blood glucose levels, and the like. These artificial intelligence can be displayed at display 78, FIG. 24

In one embodiment, artificial intelligence engine 65 contains identifications and profiles of users who have posted recommendations/ratings, as well as profiles for users and usage feedback for videos and streamed media. In one embodiment, AI engine 65 receives sensors information from one or more sensors 28. A user seeking to use the artificial intelligence engine 65 is presented (at some time) with a set of questions or the system otherwise obtains data inputs defining the characteristics of the user. In this case, the user characteristics generally define the context which is used to interpret or modify the basic goal of the user, and therefore the reference-user(s) for the user, though the user may also define or modify the context at the time of use. Various considerations are used in a cluster analysis, in which recommendations relevant to the contexts may be presented, with a ranking according to the distance function from the "cluster definition." As discussed above, once the clustering is determined, advertisements may be selected as appropriate for the cluster, to provide a subsidy for operation of the system, and also to provide relevant information for the user about available products.

Clustering algorithms partition data into a certain number of clusters (groups, subsets, or categories). Important considerations include feature selection or extraction (choosing distinguishing or important features, and only such features); Clustering algorithm design or selection (accuracy and precision with respect to the intended use of the classification result; feasibility and computational cost; etc.); and to the extent different from the clustering criterion, optimization algorithm design or selection.

Finding nearest neighbors can require computing the pairwise distance between all points. However, clusters and their cluster prototypes might be found more efficiently. Assuming that the clustering distance metric reasonably includes close points, and excludes far points, then the neighbor analysis may be limited to members of nearby clusters, thus reducing the complexity of the computation.

There are many situations in which a point could reasonably be placed in more than one cluster, and these situations are better addressed by non-exclusive clustering. In the most general sense, an overlapping or non-exclusive clustering is used to reflect the fact that an object can simultaneously belong to more than one group (class). A non-exclusive clustering is also often used when, for example, an object is "between" two or more clusters and could reasonably be assigned to any of these clusters. In a fuzzy clustering, every object belongs to every cluster with a membership weight. In other words, clusters are treated as fuzzy sets. Similarly, probabilistic clustering techniques compute the probability with which each point belongs to each cluster.

In many cases, a fuzzy or probabilistic clustering is converted to an exclusive clustering by assigning each object to the cluster in which its membership weight or probability is highest. Thus, the inter-cluster and intra-cluster distance function is symmetric. However, it is also possible to apply a different function to uniquely assign objects to a particular cluster.

A well-separated cluster is a set of objects in which each object is closer (or more similar) to every other object in the cluster than to any object not in the cluster. Sometimes a threshold is used to specify that all the objects in a cluster must be sufficiently close (or similar) to one another. The distance between any two points in different groups is larger than the distance between any two points within a group. Well-separated clusters do not need to be spherical, but can have any shape.

If the data is represented as a graph, where the nodes are objects and the links represent connections among objects, then a cluster can be defined as a connected component; i.e., a group of objects that are significantly connected to one another, but that have less connected to objects outside the group. This implies that each object in a contiguity-based cluster is closer to some other object in the cluster than to any point in a different cluster.

A density-based cluster is a dense region of objects that is surrounded by a region of low density. A density-based definition of a cluster is often employed when the clusters are irregular or intertwined, and when noise and outliers are present. DBSCAN is a density-based clustering algorithm that produces a partitional clustering, in which the number of clusters is automatically determined by the algorithm. Points in low-density regions are classified as noise and omitted; thus, DBSCAN does not produce a complete clustering.

A prototype-based cluster is a set of objects in which each object is closer (more similar) to the prototype that defines the cluster than to the prototype of any other cluster. For data with continuous attributes, the prototype of a cluster is often a centroid, i.e., the average (mean) of all the points in the cluster. When a centroid is not meaningful, such as when the data has categorical attributes, the prototype is often a medoid, i.e., the most representative point of a cluster. For many types of data, the prototype can be regarded as the most central point. These clusters tend to be globular. K-means is a prototype-based, partitional clustering technique that attempts to find a user-specified number of clusters (K), which are represented by their centroids. Prototype-based clustering techniques create a one-level partitioning of the data objects. There are a number of such techniques, but two of the most prominent are K-means and K-medoid. K-means defines a prototype in terms of a centroid, which is usually the mean of a group of points, and is typically applied to objects in a continuous n-dimensional space. K-medoid defines a prototype in terms of a medoid, which is the most representative point for a group of points, and can be applied to a wide range of data since it requires only a proximity measure for a pair of objects. While a centroid almost never corresponds to an actual data point, a medoid, by its definition, must be an actual data point.

In the k-means clustering technique K initial centroids are selected, the number of clusters desired. Each point in the data set is then assigned to the closest centroid, and each collection of points assigned to a centroid is a cluster. The centroid of each cluster is then updated based on the points assigned to the cluster. We iteratively assign points and update until convergence (no point changes clusters), or equivalently, until the centroids remain the same. For some combinations of proximity functions and types of centroids, K-means always converges to a solution; i.e., K-means reaches a state in which no points are shifting from one cluster to another, and hence, the centroids do not change. Because convergence tends to b asymptotic, the end condition may be set as a maximum change between iterations. Because of the possibility that the optimization results in a local minimum instead of a global minimum, errors may be maintained unless and until corrected. Therefore, a human assignment or reassignment of data points into classes, either as a constraint on the optimization, or as an initial condition, is possible.

To assign a point to the closest centroid, a proximity measure is required. Euclidean (L2) distance is often used for data points in Euclidean space, while cosine similarity may be more appropriate for documents. However, there may be several types of proximity measures that are appropriate for a given type of data. For example, Manhattan (L1) distance can be used for Euclidean data, while the Jaccard measure is often employed for documents. Usually, the similarity measures used for K-means are relatively simple since the algorithm repeatedly calculates the similarity of each point to each centroid, and thus complex distance functions incur computational complexity. The clustering may be computed as a statistical function, e.g., mean square error of the distance of each data point according to the distance function from the centroid. Note that the K-means may only find a local minimum, since the algorithm does not test each point for each possible centroid, and the starting presumptions may influence the outcome. The typical distance functions for documents include the Manhattan (L1) distance, Bregman divergence, Mahalanobis distance, squared Euclidean distance and cosine similarity.

An optimal clustering can be obtained as long as two initial centroids fall anywhere in a pair of clusters, since the centroids will redistribute themselves, one to each cluster. As the number of clusters increases, it is increasingly likely that at least one pair of clusters will have only one initial centroid, and because the pairs of clusters are further apart than clusters within a pair, the K-means algorithm will not redistribute the centroids between pairs of clusters, leading to a suboptimal local minimum. One effective approach is to take a sample of points and cluster them using a hierarchical clustering technique. K clusters are extracted from the hierarchical clustering, and the centroids of those clusters are used as the initial centroids. This approach often works well, but is practical only if the sample is relatively small, e.g., a few hundred to a few thousand (hierarchical clustering is expensive), and K is relatively small compared to the sample size. Other selection schemes are also available.

In the one embodiment, space requirements for K-means are modest because only the data points and centroids are stored. Specifically, the storage required is $O((m+K)n)$, where m is the number of points and n is the number of attributes. The time requirements for K-means are also modest-basically linear in the number of data points. In particular, the time required is $O(I \times K \times m \times n)$, where I is the number of iterations required for convergence. As mentioned, I is often small and can usually be safely bounded, as most changes typically occur in the first few iterations. Therefore, K-means is linear in m, the number of points, and is efficient as well as simple provided that K, the number of clusters, is significantly less than m.

In the one embodiment, outliers can unduly influence the clusters, especially when a squared error criterion is used. However, in some clustering applications, the outliers should not be eliminated or discounted, as their appropriate inclusion may lead to important insights. In some cases, such as financial analysis, apparent outliers, e.g., unusually profitable investments, can be the most interesting points.

Hierarchical clustering techniques are a second important category of clustering methods. There are two basic approaches for generating a hierarchical clustering: Agglomerative and divisive. Agglomerative clustering merges close clusters in an initially high dimensionality space, while divisive splits large clusters. Agglomerative clustering relies upon a cluster distance, as opposed to an object distance. For example, the distance between centroids or medoids of the clusters, the closest points in two clusters, the further points in two clusters, or some average distance metric. Ward's method measures the proximity between two clusters in terms of the increase in the sum of the squares of the errors that results from merging the two clusters.

Agglomerative Hierarchical Clustering refers to clustering techniques that produce a hierarchical clustering by starting with each point as a singleton cluster and then repeatedly merging the two closest clusters until a single, all-encompassing cluster remains. Agglomerative hierarchical clustering cannot be viewed as globally optimizing an objective function. Instead, agglomerative hierarchical clustering techniques use various criteria to decide locally, at each step, which clusters should be merged (or split for divisive approaches). This approach yields clustering algorithms that avoid the difficulty of attempting to solve a hard combinatorial optimization problem. Furthermore, such approaches do not have problems with local minima or difficulties in choosing initial points. Of course, the time complexity of $O(m2 \log m)$ and the space complexity of $O(m2)$ are prohibitive in many cases. Agglomerative hierarchical clustering algorithms tend to make good local decisions about combining two clusters since they can use information about the pair-wise similarity of all points. However, once a decision is made to merge two clusters, it cannot be undone at a later time. This approach prevents a local optimization criterion from becoming a global optimization criterion.

In supervised classification, the evaluation of the resulting classification model is an integral part of the process of developing a classification model. Being able to distinguish whether there is non-random structure in the data is an important aspect of cluster validation.

In one embodiment, a k-means algorithm is used as follows:

The K Means Clustering algorithm finds observations in a dataset that are like each other and places them in a set. The process starts by randomly assigning each data point to an initial group and calculating the centroid for each one. A centroid is the center of the group. Note that some forms of the procedure allow you to specify the initial sets.

Then the algorithm continues as follows: it evaluates each observation, assigning it to the closest cluster. The definition of "closest" is that the Euclidean distance between a data point and a group's centroid is shorter than the distances to the other centroids.

When a cluster gains or loses a data point, the K means clustering algorithm recalculates its centroid. The algorithm repeats until it can no longer assign data points to a closer set.

When the K means clustering algorithm finishes, all groups have the minimum within-cluster variance, which keeps them as small as possible. Sets with minimum variance and size have data points that are as similar as possible. There is variability amongst the characteristics in each cluster, but the algorithm minimizes it.

In the one embodiment, the observations within a set should share characteristics. In some cases, the analysts might need to specify different numbers of groups to determine which value of K produces the most useful results.

In one embodiment, an artificial intelligence engine 65 is used to predict what will happen; or prescriptive, meaning sensor data, from the one or more sensors, uses the data to make suggestions about what action to take, As a nonlimiting example, AI provides predictive information about a user's health, including but not limiting to reminders what to eat, when to ear, when blue sugar is how and low, and the like. Artificial intelligence can also provide predictive information about a user's other health parameters, including but not limited to, oximetry, cardiac health, and like. In one embodiment, the predictive information can be sent by telemetry to a user's physicians, nurses, monitoring station, and the like.

As a non-limiting example, AI engine 65 is used for systems with a deep learning networks with many layers. The layered network can process extensive amounts of data and determine the "weight" of each link in the network for example, in an image recognition system, some layers of the neural network might detect individual features of a face, like eyes, nose, or mouth, while another layer would be able to tell whether those features appear in a way that indicates a face.

In the one embodiment, there are many different AI engines 65 that can be trained to generate suitable output values for a range of input values; the neuro-fuzzy logic engine 65 is merely one embodiment.

In the one embodiment, measurement data, the information feeds, and the output parameters may be used to train an AI engine 65 to control the one or more devices in response to the measurement data and information feeds In one embodiment, AI engines 65 can be trained to recognize temporal patterns.

In one embodiment, sensor 68 measurement data, the information feeds, and the output parameters may be used to train an AI engine 65 to control the one or more devices in response to the measurement data and information feeds.

In the one embodiment, illustrated in FIGS. 23 and 24, a computing system 64 includes a logic subsystem 66 and a storage subsystem 68. Computing system 64 may further include an input subsystem 70, an output subsystem 72, a communication subsystem 74, and/or other components not shown in FIGS. 23 and 24.

In the one embodiment, logic subsystem 66 may include one or more physical logic devices configured to execute instructions. For example, the logic subsystem may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

In the one embodiment, logic subsystem 66 includes one or more processors (as an example of physical logic devices) configured to execute software instructions. Additionally, or alternatively, the logic subsystem may include one or more hardware and/or firmware logic machines (as an example of physical logic devices) configured to execute hardware or firmware instructions.

Processors of the logic subsystem may be single-core or multi-core, and the instructions executed thereon may be configured for sequential, parallel, and/or distributed processing. Individual components of the logic subsystem may be distributed among two or more separate devices, which may be remotely located and/or configured for coordinated processing. Aspects of the logic subsystem may be virtualized and executed by remotely accessible, networked computing devices configured in a cloud-computing configuration.

In the one embodiment, storage subsystem 68 includes one or more physical, non-transitory memory devices configured to hold instructions executable by the logic subsystem in non-transitory form, to implement the methods and processes described herein. When such methods and processes are implemented, the state of storage subsystem 68 may be transformed. e.g., to hold different data. Storage subsystem 68 may include removable and/or built-in devices. Storage subsystem 68 may include optical memory devices, semiconductor memory devices, and/or magnetic memory devices, among other suitable forms. Storage subsystem 68 may include volatile, nonvolatile, dynamic, static, read/write, read-only, random-access, sequential-access, location-addressable, file-addressable, and/or content-addressable devices. Aspects of logic subsystem 66 and storage subsystem 68 may be integrated together into one or more hardware-logic components. While storage subsystem 68 includes one or more physical devices, aspects of the instructions described herein alternatively may be propagated by a communication medium (e.g., an electromagnetic signal, an optical signal, etc.) that is not necessarily held by a physical device for a finite duration.

In the one embodiment, an AI database hosted on cloud platform 76 is configured to cooperate with AI engine 65. In an embodiment, the AI database stores and indexes trained AI objects and its class of AI objects have searchable criteria. The AI database cooperates with search engine 115 to utilize search criteria supplied from a user, from either or both 1) via scripted software code and 2) via data put into defined fields of a user interface. S115 can search engine utilizes the search criteria in order for search engine 115 to retrieve one or more AI data objects that have already been trained as query results. The AI database is coupled to an AI engine to allow any of reuse, reconfigure ability, and recomposition of the one or more trained AI data objects from the AI database into a new trained AI model. These and other features of the design provided herein can be better understood with reference to the drawings, description, and claims, all of which form the disclosure of this patent application.

In general, AI database 114 stores and indexes trained AI objects and its class of AI objects have searchable criteria. AI database 114 cooperates with search 115 engine to utilize search criteria supplied from a user to retrieve one or more AI data objects that have already been trained as query results. The AI database1 14 is coupled to AI engine 65 to allow any of reuse, reconfigure ability, and recomposition of the one or more trained AI data objects from the AI database into a new trained AI model 106.

FIG. 23 provides a schematic illustrating an AI system 65 in accordance with some embodiments of the present invention. In one embodiment, in response to received data from sensors 28 and/or users, the AI database 141 stores and indexes trained AI objects and the class of AI objects have searchable criteria. The AI database 141 of searchable AI objects indexes parameters and characteristics known about the AI objects that allows searching of user supplied criteria from either or both 1) scripted code and 2) defined fields in a user interface.

In the one embodiment, engine 65 utilizes this search criteria supplied from the user or sensors 28, from either or both 1) via scripted software code and 2) via data put into defined fields of a user interface, in order for AI engine 65 to find and retrieve relevant AI data objects that have already been trained as query results. In an embodiment, the AI database also stores a specification for a model and not the fully trained AI model itself, because the untrained model has not yet been trained. In the one embodiment, engine is 65 use of the user supplied search criteria from the user interfaces to find relevant trained AI objects stored in the AI data will be described in more detail later.

AI database can index AI objects corresponding to the main concept and the set of sub concepts making up a given trained AI model so that reuse, recomposition, and reconfiguration of all or part of a trained AI model is possible.

AI database 141 can be also coupled to engine 65 to allow any of reuse, reconfigure ability, and recomposition of the one or more trained AI data objects into a new trained AI model. As a non-limiting example, AI engine 65 can generates AI models, such as a first AI model.

The AI database 141 may be part of and cooperate with various other modules of AI engine 65. In one embodiment, AI engine 65 has a set of user interfaces 112 to import from either or both 1) scripted software code written in a pedagogical software programming language, such as Inkling, and/or 2) from the user interface 112 with defined fields that map user supply criteria to searchable criteria of the AI objects indexed in the AI database 141

The AI database 141 can be part of cloud-based AI service. The AI database 141 can be hosted on cloud platform with the search engine 115 and AI engine 65.

As a non-limiting example, The AI database 141 cooperates with AI engine 65. AI engine 65 can further include an architect module 126, an instructor module 124, and a learner module 128. In the one embodiment, architect module 126 creates and optimizes learning topologies of an AI object, such as the topology of a graph of processing nodes, for the AI objects. The instructor module 124 carries out a training plan codified in a pedagogical software programming language. The learner module 128 carries out an actual execution of the underlying AI learning algorithms during a training session. The architect module 126, when reconfiguring or recomposing the AI objects, composes one or more trained AI data objects into a new AI model and then the instructor module 124 and learner module 128 cooperate with one or more data sources to train the new AI model.

User interface, to the AI database 141 and search engine 115, can be configured to present a population of known trained AI objects. In the one embodiment, search engine 115 cooperates with the AI database 141 is configured to search the population of known trained AI objects to return a set of one or more already trained AI objects similar to a problem trying to be solved by the user supplying the search criteria.

The database management system tracking and indexing trained AI objects corresponding to concepts is configured to make it easy to search past experiments, view results, share with others, and start new variants of a new trained AI model.

In the one embodiment, AI database 141 may be an object orientated database, a relational database, or other similar database, that stores a collection of AI objects (i.e., the trained main concept and sub concepts forming each trained AI model). The AI database 141 can be composed of a set of one or more databases in which each database has a different profile and indexing, where the set of databases are configured to operate in a parallel to then send back accurate, fast, and efficient returns of trained AI objects that satisfy the search query.

In the one embodiment, AI engine 65 generates a trained AI model 106 and can include one or more AI-generator modules selected from at least an instructor module 124, an architect module 126, and a learner module 128 as shown. The instructor module 324 can optionally include a hyperlearner module 125, and which can be configured to select one or more hyperparameters for any one or more of a neural network configuration, a learning algorithm, a learning optimizer, and the like.

The hyperlearner module 125 can optionally be contained in a different AI-generator module such as the architect module 126 or the learner module 128, or the hyperlearner module 125 can be an AI-generator module itself. The learner module 1328 can optionally include a predictor module 129, which can provide one or more predictions for a trained AI model. The predictor module 129 can optionally be contained in a different AI-generator module such as the instructor module 124 or the architect module 126, or the predictor module 129 can be an AI-generator module itself. AI engine 65 can generate the trained AI model 106, such as trained AI model 106, from compiled scripted software code written in a pedagogical software programming language via one or more training cycles with AI engine 65.

One or more clients 110 can make a submission to create a trained AI model. Once a Mental Model and Curricula have been coded in the pedagogical software programming language, then the code can be compiled and sent to the three main modules, the learner module 128, the instructor module 124, and the architect module 126 of AI engine 65 for training. One or more user interfaces 112, such a web interface, a graphical user interface, and/or command line interface, will handle assembling the scripted code written in the pedagogical software programming language, as well as other ancillary steps like registering the line segments with AI engine 65, together with a single command. However, each module—the AI compiler module 122, the web enabled interface to AI engine 65, the learner module 128 be used in a standalone manner, so if the author prefers to manually invoke the AI compiler module, manually perform the API call to upload the compiled pedagogical software programming language to the modules of AI engine 65, and the like As a non-limiting example, one or more clients 110 can send scripted code from a coder 112 or another user interface to AI compiler 122. AI compiler 122 compiles the scripted software code written in a pedagogical software programming language. AI compiler 122 can send the compiled scripted code, similar to an assembly code, to the instructor module 124, which, in turn, can send the code to the architect module 126. In one embodiment, AI compiler 222 can send the compiled scripted code in parallel to all of the modules needing to perform an action on the compiled scripted code. The architect module 126 can propose a vast array of machine learning algorithms, such as various neural network layouts, as well as optimize the topology of a network of intelligent processing nodes making up an AI object. The architect module 126 can map between concepts and layers of the network of nodes and send one or more instantiated AI objects to the learner module 128. Once the architect module 126 creates the topological graph of concept nodes, hierarchy of sub concepts feeding parameters into that main concept (if a hierarchy exists in this layout), and learning algorithm for each of the main concept and sub concepts, then training by the learner module 128 and instructor module 124, which can be couped to a hyper learner 125, can begin.

The instructor module 124 can request training data from the training data source 219. Training can be initiated with an explicit start command in the pedagogical software programming language from the user to begin training. In order for training to proceed, the user needs to have already submitted compiled pedagogical software programming language code and registered all of their external data sources such as simulators (if any are to be used) via the user interfaces with the learner and instructor modules 124, 126 of AI engine 65.

The training data source 119 can send the training data to the instructor module 124 upon the request. The instructor module 124 can subsequently instruct the learner module 128 on training the AI object with pedagogical software programming language based curricula for training the concepts into the AI objects. Training an AI model 106 can take place in one or more training cycles to yield a trained state of the AI model 106. The instructor module 124 can decide what pedagogical software programming language based concepts and streams should be actively trained in a mental model. The instructor module 124 can know what are the terminating conditions for training the concepts based on user criteria and/or known best practices. The learner module 128 or the predictor 129 can elicit a prediction from the trained AI model 106 and send the prediction to the instructor module 124. The instructor module 124, in turn, can send the prediction to the training data source 119 for updated training data based upon the prediction and, optionally, instruct the learner module 328 in additional training cycles. When the one or more training cycles are complete, the learner module 328 can save the trained state of the network of processing nodes in the trained AI model 106. (Note a more detailed discussion of different embodiments of the components making up AI engine 65 occurs later.)

The AI database may consist of a storage layer which is configured to know how to efficiently store database objects, in this case AI objects, an indexing mechanism to speed retrieval of the stored AI objects, engine 115 to translate a query request into a retrieval strategy to retrieve AI objects that satisfy a query, and a query language which describes to the AI database what AI objects are desired to be retrieved.

As a non-limiting example, search engine 115 is configured to 1) parse scripted software code written in a pedagogical software programming language and then map that to one or more searchable criteria as well as 2) import the data put into defined fields of the user interface to use as searchable criteria to find relevant trained AI objects indexed in the AI database 341. In an embodiment, the search engine 115 is configured to also be able to do a natural language search of a submitted description from a user to determine what a similar trained object would be by referencing the 1) indexed criteria and/or 2) signatures and/or 3) example models in the database.

In one embodiment, AI database 141 is indexed with keywords and problems solved about each stored AI object In one embodiment, search engine 115 in query results will return relevant AI objects. The relevant AI objects can be evaluated and return based on a number of different weighting factors including number of resources consumed to train that concept learned by the AI object In one embodiment, search engine 115 utilizes sensor 28 data for relevant trained AI objects. In an embodiment, search engine 343 refers to 1) the signatures of the stored AI objects as well as 2) any indexed parameters for the AI objects indexed by the AI database 141.

In an embodiment, the AI database 141 and search engine 115 build an index of algorithms and parameters that have been tried in past.

FIGS. 24 (a) and (b) provide schematics illustrating mental models 200A and 200B.

In one embodiment, AI engine 65 takes in a description of a problem and how one would go about teaching concepts covering aspects of the problem to be solved, and AI engine 65 compiles the coded description into lower-level structured data objects that a machine can more readily understand, builds a network topology of the main problem concept and sub-concepts covering aspects of the problem to be solved, trains codified instantiations of the sub-concepts and main concept, and executes a trained AI model 106 containing one, two, or more neural networks.

In one embodiment, AI engine 65 can abstract away and automate the low-level mechanics of AI. AI engine 65 can manage and automate much of the lower level complexities of working with AI. Each program developed in the pedagogical programming language can be fed into AI engine 65 in order to generate and train appropriate intelligence models.

AI engine 65 can abstract generation of a neural network topology for an optimal solution and faster training time with a curriculum and lessons to teach the neural network via recursive simulations and training sessions on each node making up the neural network.

In one embodiment, AI engine 65 can contain a vast array of machine learning algorithms, has logic for picking learning algorithms and guiding training, manages data streaming and data storage, and provides the efficient allocation of hardware resources. AI engine 65 can be built with an infrastructure that supports streaming data efficiently through the system. AI engine 65 can use a set of heuristics to make choices about which learning algorithms to use to train each BRAIN. The set of heuristics also make it possible for AI engine 65 to choose from any number of possible algorithms, topologies, and the like. be able to train a number of BRAINs in parallel, and then pick the best result from all of the train BRAINs as the best trained AI model for that task.

Figure 25:
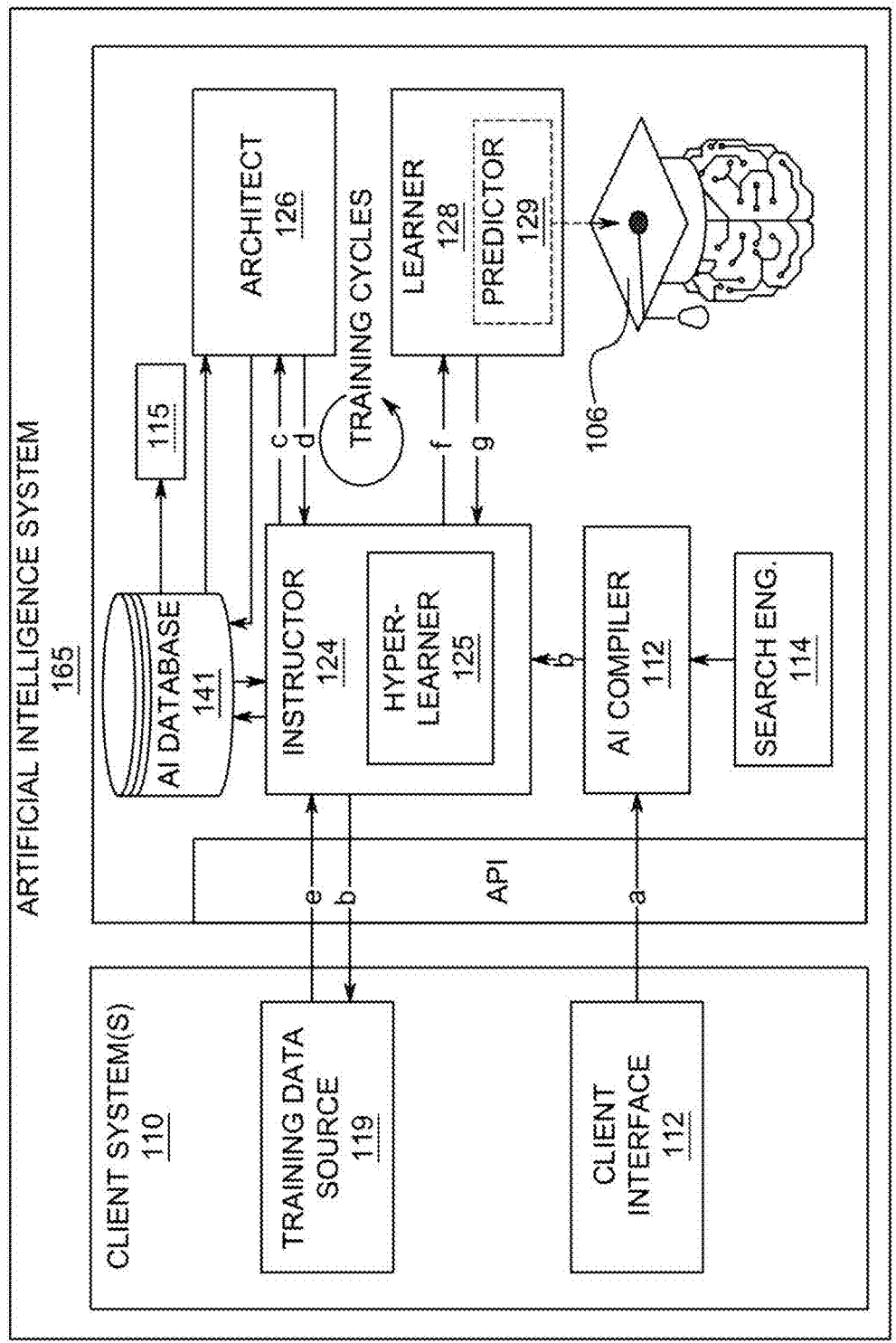
FIG. 25 provides a schematic illustrating an AI system in accordance with some embodiments.

FIG. 25 provides a schematic illustrating an AI system including an AI engine 65 in accordance with some embodiments.

The details for any given implementation of an AI engine 65 may vary substantially, but many have common architectural components such as the following six components: 1) an architect module 126, 2) an instructor module 124, 3) a learner module 128, 4) a compiler module 122, 5) a hyperlearner module 125, and 6) one or more interfaces 112 exchanging communications into and out of AI engine 65.

The AI database 141 and search engine 115 may cooperate with the modules of AI engine 65 as discussed above.

In one embodiment, AI engine 65 is a cloud-hosted platform-as-a-service configured to manage complexities inherent to training AI networks. AI engine 65 can be accessible with one or more client-side interfaces 112, GUI, CLI, and Web interfaces, to allow third parties to submit a description of a problem in a pedagogical programming language with possible sub concepts that factor in that problem and let the online AI 65 engine build and generate a trained intelligence model for one or more of the third parties.

In one embodiment, AI system includes the coder 112 on the one or more client systems and the following on the one or more server systems: the AI compiler module 122; the AI-generator modules including the instructor module 124, the architect module 126, and the learner module 128, the hyperlearner 125, and the predictor 129 module. In addition to the foregoing, the AI system can include a training data loader 221 configured to load training data from a training data database 214 a, a simulator 614 b, and a streaming data server. The training data can be batched training data, streamed training data, or a combination thereof, and AI engine 65 can be configured to push or pull the training data from one or more training data sources selected from the simulator 214 b, a training data generator, the training data database 214 a, or a combination thereof. In some embodiments, a data stream manager can be configured to manage streaming of the streamed training data. FIG. 25 shows the architect module 126 configured to propose a neural network layout and the learner module 128 configured to save a trained state of a neural network such as the trained AI model 106.

In one embodiment, AI compiler module 122 automates conversion and compiling of the pedagogical programming language describing the problem (main concept) and sub-concepts factoring into the problem. Each statement recited in the code of the pedagogical programming language program submitted to AI engine 65 can be complied into a structured data object's defined fields, which can later be generated and instantiated into its own sub-concept node by the architect module 326. Each node can have one or more inputs one or more neural networks to process the input data and a resulting output decision/action. The compiled statements, commands, and other codifications fed into the AI compiler can be transformed into a lower level AI specification.

In one embodiment, architect module 126 is the component of the system responsible for proposing and optimizing learning topologies (e.g., neural networks) based on mental models.

Neural networks can be based on a large collection of neural units loosely modeling the way a biological brain solves problems with large clusters of biological neurons connected by axons. Each neural unit is connected with many others, and links can be enforcing or inhibitory in their effect on the activation state of connected neural units. Each individual neural unit can have, for example, a summation function, which combines the values of all its inputs together. There may be a threshold function or limiting function on each connection and on the unit itself such that it must surpass it before it can propagate to other neurons. These systems are self-learning and trained rather than explicitly programmed and excel in areas where the solution or feature detection is difficult to express in a traditional computer program.

Neural networks can consist of multiple layers or a cube design, and the signal path can traverse from front to back. The goal of the neural network is to solve problems in the same way that the human brain would, although several neural networks are much more abstract. Modern neural network projects typically work with a few thousand and up to a few million neural units and millions of connections.

In one embodiment, architect module 126 can take the codified mental model and pedagogy and then propose a set of candidate low-level learning algorithms, topologies of a main concepts and sub-concepts, and configurations thereof the architect module 126 believes will best be able to learn the concepts in the model. This is akin to the work that a data scientist does in the toolkit approach, or that the search system automates in the approach with statistical data analysis tools. In one embodiment, it is guided by the pedagogical program instead of being a broad search. The architect module 126 can employ a variety of techniques to identify such models. The architect module 126 can generate a directed graph of nodes. The architect module 126 can break down the problem to be solved into smaller tasks/concepts all factoring into the more complex main problem trying to be solved based on the software code and/or data in the defined fields of the user interface supplied from the user/client device. The architect module 126 can instantiate a main concept and layers of sub-concepts feeding into the main concept. Architect module 126 can generate each concept including the sub-concepts with a tap that stores the output action/decision and the reason why that node reached that resultant output (e.g., what parameters dominated the decision and/or other factors that caused the node to reach that resultant output). This stored output of resultant output and the reasons why the node reached that resultant output can be stored in the trained intelligence model. The tap created in each instantiated node allows explainability for each step on how a trained intelligence model produces its resultant output for a set of data input. The architect module 326 can reference a database of algorithms to use as well as a database of network topologies to utilize. The architect module 326 can reference a table or database of best suggested topology arrangements including how many layers of levels in a topology graph for a given problem, if available. Architect module 126 also has logic to reference similar problems solved by comparing signatures. If the signatures are close enough, the architect module 326 can try the topology used to optimally solve a problem stored in an archive database with a similar signature. Architect module 126 can also instantiate multiple topology arrangements all to be tested and simulated in parallel to see which topology comes away with optimal results. The optimal results can be based on factors such as performance time, accuracy, computing resources needed to complete the training simulations, and the like.

In some embodiments, architect module 126 can be configured to propose a number of neural networks and heuristically pick an appropriate learning algorithm from a number of machine learning algorithms in one or more databases for each of the number of neural networks. Instances of the learner module 128 and the instructor module 124 can be configured to train the number of neural networks in parallel. The number of neural networks can be trained in one or more training cycles with the training data from one or more training data sources. AI engine 65 can subsequently instantiate a number of trained AI models 106 based on the concepts learned by the number of neural networks in the one or more training cycles, and then identify a best trained AI model (e.g., by means of optimal results based on factors such as performance time, accuracy, etc.) among the number of trained AI models 106.

In one embodiment, the user can assist in building the topology of the nodes by setting dependencies for particular nodes. Architect module 126 can generate and instantiate neural network topologies for all of the concepts needed to solve the problem in a distinct two-step process. The architect module 326 can generate a description of the network concepts. The architect module 326 can also take the description and instantiate one or more topological shapes, layers, or other graphical arrangements to solve the problem description. The architect module 326 can select topology algorithms to use based on factors such as whether the type of output the current problem has either 1) an estimation output or 2) a discrete output and then factors in other parameters such as performance time to complete the algorithm, accuracy, computing resources needed to complete the training simulations, originality, number of attributes, and the like.

In one embodiment, instructor module 124 is a component of the system responsible for carrying out a training plan codified in the pedagogical programming language. Training can include teaching a network of intelligent processing nodes to get one or more outcomes, for example, on a simulator. To do so, instructor module 124 can form internal representations about the system's mastery level of each concept, and adapt the execution plan based on actual performance during training. The directed graph of lessons can be utilized by instructor module 124 to determine an execution plan for training (e.g., which lessons should be taught in which order). The training can involve using a specific set of concepts, a curriculum, and lessons, which can be described in the pedagogical programming language file.

In one embodiment, instructor module 124 can train easier-to-understand tasks earlier than more complex tasks. Thus, the instructor module 324 can train sub-concept AI objects and then higher-level AI objects. The instructor module 124 can train sub-concept AI objects that are dependent on other nodes after those other AI objects are trained. However, multiple nodes in a graph may be trained in parallel. Instructor module 124 can run simulations on the AI objects with input data including statistics and feedback on results from the AI object being trained from learner module 128. Learner module 128 and instructor module 124 can work with a simulator or other data source to iteratively train an AI object with different data inputs. The instructor module 124 can reference a knowledge base of how to train an AI object efficiently by different ways of flowing data to one or more AI objects in the topology graph in parallel, or, if dependencies exist, the instructor module 124 can train serially with some portions of lessons taking place only after earlier dependencies have been satisfied. The instructor module 324 can reference the dependencies in the topology graph, which the dependencies can come from a user specifying the dependencies and/or how the arrangement of AI objects in the topology was instantiated. Instructor module 124 can supply data flows from the data source such as a simulator in parallel to multiple AI objects at the same time where computing resources and a dependency check allows the parallel training.

In one embodiment, the instructor module 124 may flow data to train AI objects from many data sources including, but not limited to a simulator, a batch data source, a random-data generator, and historical/guided performance form from past performance. A simulator can give data and get feedback from the instructor module 124 during the simulation that can create an iterative reactive loop from data inputs and data outputs from the AI objects. A batch data source can supply batched data from a database in at least one example. A random-data generator can generate random data based on user-input parameters.

When starting a training operation, instructor module 124 first generates an execution plan. This is the ordering it intends to use when teaching the concepts, and for each concept which lessons it intends to teach in what order. While the execution plan is executing, instructor module 124 may jump back and forth between concepts and lessons to optimize the learning rate.

In one embodiment, instructor module 124 looks to reuse similar training flows that have solved similar problems with similar signatures in the past.

In one embodiment, learner module 128 is a component of the system configured to carry out the actual execution of the low-level, underlying AI algorithms. In training mode, the learner module 328 can instantiate a system conforming to what was proposed by the architect module 326, interface with instructor module 124 to carry out the computation and assess performance, and then execute the learning algorithm itself. Learner module 128 can instantiate and execute an instance of the already trained system. Eventually, learner module 128 writes out network states for each trained sub-AI object and then a combination of the topological graph of the main node with all of the sub-nodes into a trained AI model 106. Learner module 128 can also write the stored output of each node and why that node arrived at that output into the trained AI model, which gives explainability as to how and why the AI proposes a solution or arrives at an outcome.

In one embodiment, hyperlearner module 125 performs a comparison of a current problem to a previous problem in one or more databases. Hyperlearner module 125 can reference archived, previously built and trained intelligence models to help guide instructor module 124 to train the current model of nodes. Hyperlearner module 125 can parse an archive database of trained intelligence models, known past similar problems and proposed solutions, and other sources. Hyperlearner module 125 can compare previous solutions similar to the solutions needed in a current problem as well as compare previous problems similar to the current problem to suggest potential optimal neural network topologies and training lessons and training methodologies. As a non-limiting example, when, the curriculum trains using a simulation or procedural generation, then the data for a lesson is not data to be passed to the learning system, but the data is to be passed to the simulator. The simulator can use this data to configure itself, and the simulator can subsequently produce a piece of data for the learning system to use for training. This separation permits a proper separation of concerns. The simulator is the method of instruction, and the lesson provides a way to tune that method of instruction, which makes it more or less difficult depending on the current level of mastery exhibited by the learning system. A simulation can run on a client machine and stream data to AI engine 65 for training. In such an embodiment, the client machine needs to remain connected to AI engine 65 while the BRAIN is training. However, if the client machine is disconnected from the server of AI engine 65, it can automatically pick up where it left off when it is reconnected.

As a non-limiting example, a machine learning algorithm may have of a target/outcome variable (or dependent variable) which is to be predicted from a given set of predictors (independent variables). Using this set of variables, AI engine 65 generates a function that map inputs to desired outputs. The coefficients and weights plugged into the equations in the various learning algorithms are then updated after each epoch/pass of training session until a best set of coefficients and weights are determined for this particular concept. The training process continues until the model achieves a desired level of accuracy on the training data.

When in training mode architect module 126 of AI engine 65 is configured to i) instantiate the network of processing nodes in any layers of hierarchy conforming to concepts of the problem being solved proposed by the user and ii) then the learner module 128 and instructor module 124 train the network of processing nodes in that AI model. To affect the foregoing, AI engine 65 can take compiled pedagogical programming language code and generate a BRAIN learning topology, and proceed to follow the curricula to teach the concepts as specified. Depending on the model, training can potentially take substantial amounts of time. AI engine can provide interactive context on the status of training including, for example, showing which nodes are actively being trained, the current belief about each node's mastery of its associated concept, overall and fine-grained accuracy and performance, the current training execution plan, and/or an estimate of completion time. As such, in some embodiments, AI engine 65 can be configured to provide one or more training status updates on training a neural network selected from i) an estimation of a proportion of a training plan completed for the neural network, ii) an estimation of a completion time for completing the training plan, iii) the one or more concepts upon which the neural network is actively training, iv) mastery of the neural network on learning the one or more concepts, v) fine-grained accuracy and performance of the neural network on learning the one or more concepts, and vi) overall accuracy and performance of the neural network on learning one or more mental models.

Because the process of building pedagogical programs is iterative, AI engine 65 in training mode can also provide incremental training. That is to say, if the pedagogical programming language code is altered with respect to a concept that comes after other concepts that have already been trained, those antecedent concepts do not need to be retrained.

Additionally, in training mode, the user is able to specify what constitutes satisfactory training should the program itself permit indefinite training.

As a non-limiting example, a first step AI engine 65 can take is to pick an appropriate learning algorithm to train a mental model. AI engine 65 can have knowledge of many of the available learning algorithms, as well as a set of heuristics for picking an appropriate algorithm including an initial configuration to train from.

As a non-limiting example, the process of picking an appropriate algorithm, and the like, can be performed by a BRAIN that has been trained (and will continue to be trained) by AI engine, meaning the BRAIN will get better at building BRAINs each time a new one is built. A trained AI-engine neural network, such as a BRAIN, thereby provides enabling AI for proposing neural networks from assembly code and picking appropriate learning algorithms from a number of machine learning algorithms in one or more databases for training the neural networks. AI engine can be configured to continuously train trained AI-engine neural network in providing the enabling AI for proposing the neural networks and picking the appropriate learning algorithms thereby getting better at building BRAINs.

Architect module 126 can also use heuristics, mental model signatures, statistical distribution inference, and Meta-learning in topology and algorithm selection.

AI engine 100 and architect module 126 can be configured to heuristically pick an appropriate learning algorithm from a number of machine learning algorithms in one or more databases for training the neural network proposed by architect module 126. Many heuristics regarding the mental model can be used to inform what types of AI and machine learning algorithms can be used. For example, the data types used have a large influence. For this reason, the pedagogical programming language contains rich native data types in addition to the basic data types. If architect module 126 sees, for example, that an image is being used, a convolutional deep learning neural network architecture might be appropriate. If architect module 126 sees data that is temporal in nature (e.g., audio data, sequence data, etc.), then a recursive deep-learning neural network architecture like a long short-term memory ("LSTM") network might be more appropriate. The collection of heuristics can be generated by data science and machine learning/AI experts who work on architect module 126 codebase, and who attempt to capture the heuristics that they themselves use in practice. As a non-limiting example, in addition to looking at the mental model, architect module 126 can also consider the pedagogy provided in the pedagogical programming language code. It can, for example, look at the statistical distribution of any data sets being used; and, in the case of simulators, it can ask the simulator to generate substantial amounts of data so as to determine the statistics of data that will be used during training. These distribution properties can further inform the heuristics used.

In one embodiment, Meta-learning is an advanced technique used by architect module 126. It is, as the name implies, learning about learning. What this means is that as architect module 126 can generate candidate algorithm choices and topologies for training, it can record this data along with the signature for the model and the resultant system performance. This data set can then be used in its own learning system. Thus, architect module 126, by virtue of proposing, exploring, and optimizing learning models, can observe what works and what does not, and use that to learn what models it should try in the future when it sees similar signatures.

In one embodiment, AI engine can include a meta-learning module configured to keep a record such as a meta-learning record in one or more databases. The record can include i) the source code processed by AI engine, ii) mental models of the source code and/or signatures thereof, iii) the training data used for training the neural networks, iv) the trained AI models, v) how quickly the trained AI models were trained to a sufficient level of accuracy, and vi) how accurate the trained AI models became in making predictions on the training data.

In one embodiment, AI engine 65 will take is to pick an appropriate learning algorithm to train the Mental Model. This is a critical step in training AI. AI engine has knowledge of many of available learning algorithms and has a set of heuristics for picking an appropriate algorithm as well as an initial configuration to train from.

Once an algorithm is chosen, AI engine 65 can proceed with training BRAIN's Mental Model via Curricula. AI engine manages all of data streaming, data storage, efficient allocation of hardware resources, choosing when to train each concept, how much (or little) to train a concept given its relevance within Mental Model (i.e., dealing with common problems of overfitting and underfitting), and generally is responsible for producing a trained AI model based on given Mental Model and Curricula. As is case with picking an appropriate learning algorithm, guiding training—notably avoiding overfitting and underfitting—to produce an accurate AI solution is a task that requires knowledge and experience in training AIs. AI engine has an encoded set of heuristics manage this without user involvement. Similarly, process of guiding training is also a trained AI model that will only get smarter with each trained AI model it trains. AI engine is thus configured to make determinations regarding i) when to train AI model on each of one or more concepts and ii) how extensively to train AI model on each of one or more concepts. Such determinations can be based on relevance of each of one or more concepts in one or more predictions of a trained AI model based upon training data.

In one embodiment, AI engine can also determine when to train each concept, how much (or little) to train each concept based on its relevance, and, ultimately, produce a trained BRAIN. AI engine can utilize meta-learning. In meta-learning, AI engine keeps a record of each program it is seen, data it used for training, and generated AIs that it made. It also records how fast those AIs trained and how accurate y became. AI engine learns over that dataset.

In one embodiment, when training of an AI object occurs, hyper learner module 328 can be configured to save into AI database 141 two versions of an AI object. A first version of an AI object is a collapsed tensile flow representation of AI object. A second version of an AI object is representation left in its nominal non-collapsed state. When search engine 343 retrieves AI object in its nominal non-collapsed state, a programmer desiring to reuse AI object will be able to obtain outputs from non-collapsed graph of nodes with all of its rich meta-data and a collapsed concept with a single discrete output. state of AI data objects can be in a non-collapsed state so trained AI object has its full rich data set, which n may be used by user for reuse, reconfigured, or recomposed into a subsequent trained AI model.

In one embodiment, database management system also indexes and tracks different AI objects with an indication of what version is this AI object. Later versions of an AI object may be better trained for particular task but earlier versions of AI object maybe more generally trained; and thus, reusable for wider range of related tasks, and further trained for that specific task.

In one embodiment, AI database 141 and or components in AI engine cooperate to allow migrations of learned state to reconfigure a trained AI object. When a system has undergone substantial training achieving a learned state, and a subsequent change to underlying mental models might necessitate retraining, it could be desirable to migrate learned state rather than starting training from scratch. AI engine can be configured to afford transitioning capabilities such that previously learned high dimensional representations can be migrated to appropriate, new, high dimensional representations. This can be achieved in a neural network by, for example, expanding width of an input layer to account for alterations with zero-weight connections to downstream layers. system can n artificially diminish weights on connections from input that are to be pruned until y hit zero and can n be fully pruned.

In one embodiment, Once a trained AI model has been sufficiently trained, it can be deployed such that it can be used in a production application. interface for using a deployed trained AI model is simple: user submits data (of same type as trained AI model was trained with) to a trained AI model-server API and receives trained AI model's evaluation of that data.

In one embodiment, Though a linear approach to building a trained AI model is presented in some embodiments, an author-train-deploy workflow does not have to be treated as a waterfall process. If user decides first refinement of a trained AI model 106 is needed, be it through additional training with existing data, additional training with new, supplemental data, or additional training with a modified version of mental model or curricula used for training, AI engine is configured to support versioning of BRAINs so that user can preserve (and possibly revert to) current state of a BRAIN while refining trained state of BRAIN until a new, more satisfactory state is reached.

In one embodiment, two or more AI objects can be merged for recomposition and into a new AI object that n in one more sessions learn to work with each or to form a new trained AI model. simulation time to fully train each of those two or more AI objects merged for recomposition is a much shorter time than starting from scratch and having to train two or more concepts and n having those two concepts having to figure out how to work with each or to achieve an optimal result.

In one embodiment, AI database 141, AI engine 65, and search engine 143 cooperate for storage and retrieval of a database of AI concepts, which can create a new subsequent AI trained object by essentially merging one or more stored trained AI objects with more AI objects in order to recompose to get a new trained AI model.

AI object may be reconfigured and trained with new coefficients for learning algorithm. Additionally, AI object may also be reused with same set of coefficients for its learning algorithm. Again, as an example, later different versions of an AI object may be better trained for particular task but earlier versions of AI object maybe more generally trained; and thus, reusable for wider range of related tasks, to n be first trained for that specific task.

Figure 26A:
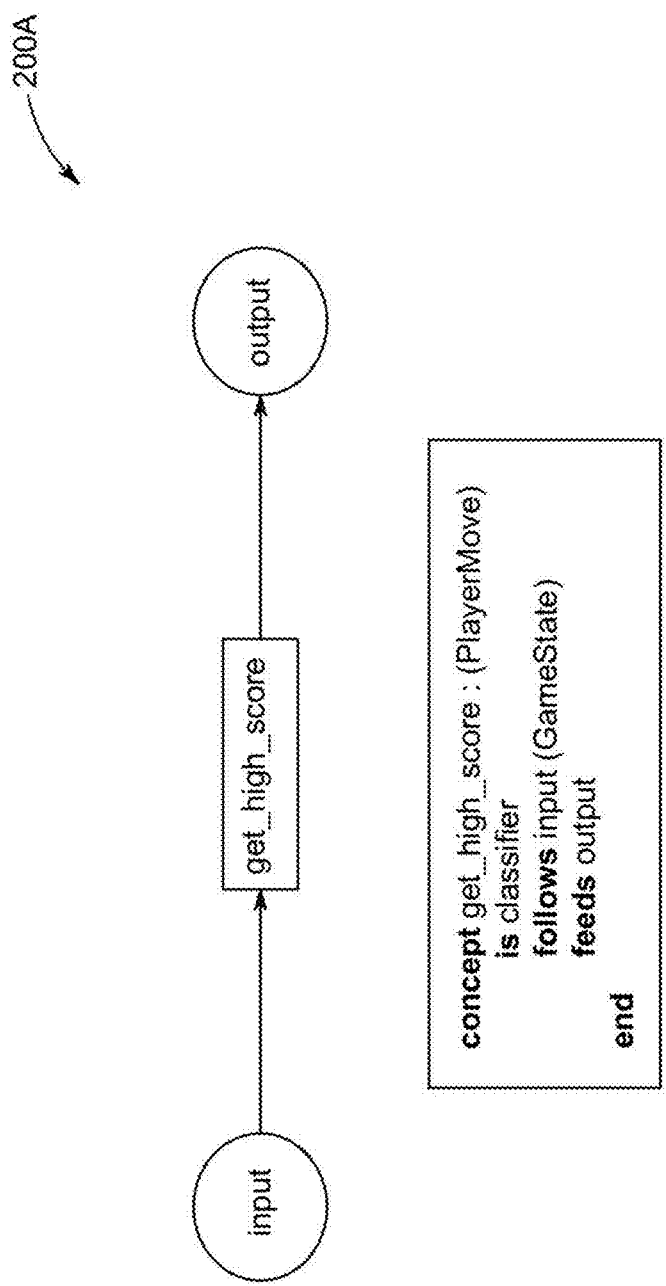
FIG. 26A provides a schematic illustrating a mental model in accordance with some embodiments.

FIG. 26A provides a schematic illustrating an AI system 300A in accordance with some embodiments.

Figure 32:
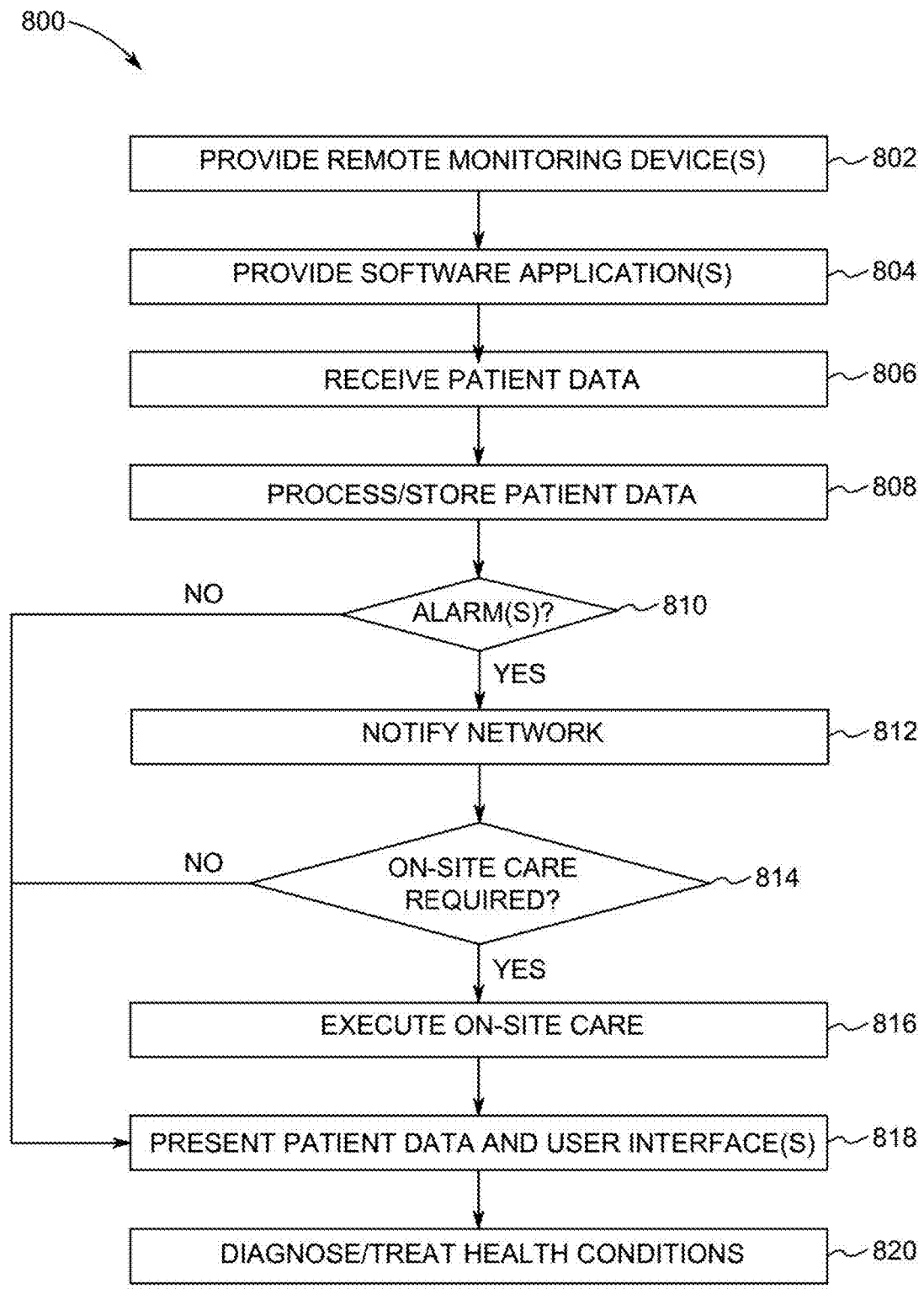
FIG. 32 is another flowchart of a method for patient monitoring, according to some embodiments of the present disclosure.

In FIG. 26A a user such as a software developer can interface with AI system 300(*a*) through an online interface; however, user is not limited to online interface, and online interface is not limited to that shown in FIG. 26A With this in mind, AI system 700A of FIG. 32 can enable a user to make API and web requests through a domain name system ("DNS"), which requests can be optionally filtered through a proxy to route API requests to an API load balancer and web requests to a web load balancer. API load balancer can be configured to distribute API requests among multiple BRAIN service containers running in a Docker network or containerization platform configured to wrap one or more pieces of software in a complete filesystem containing everything for execution including code, runtime, system tools, system libraries, etc. web load balancer can be configured to distribute web requests among multiple web service containers running in Docker network. Docker network or Docker BRAIN network can include central processing unit ("CPU") nodes and graphics processing unit ("GPU") nodes, nodes of which Docker network can be auto scaled as needed. CPU nodes can be utilized for most BRAIN-service containers running on Docker network, and GPU nodes can be utilized for more computationally intensive components such as TensorFlow and learner. A BRAIN-service engineer can interface with AI system 300(*a*) through virtual private cloud ("VPC") gateway and a hardened bastion host configured to secure Docker network. An Elastisearch-Logstash-Kibana ("ELK") stack cluster can be shared among all production clusters for dedicated monitoring and logging.

Figure 26B:
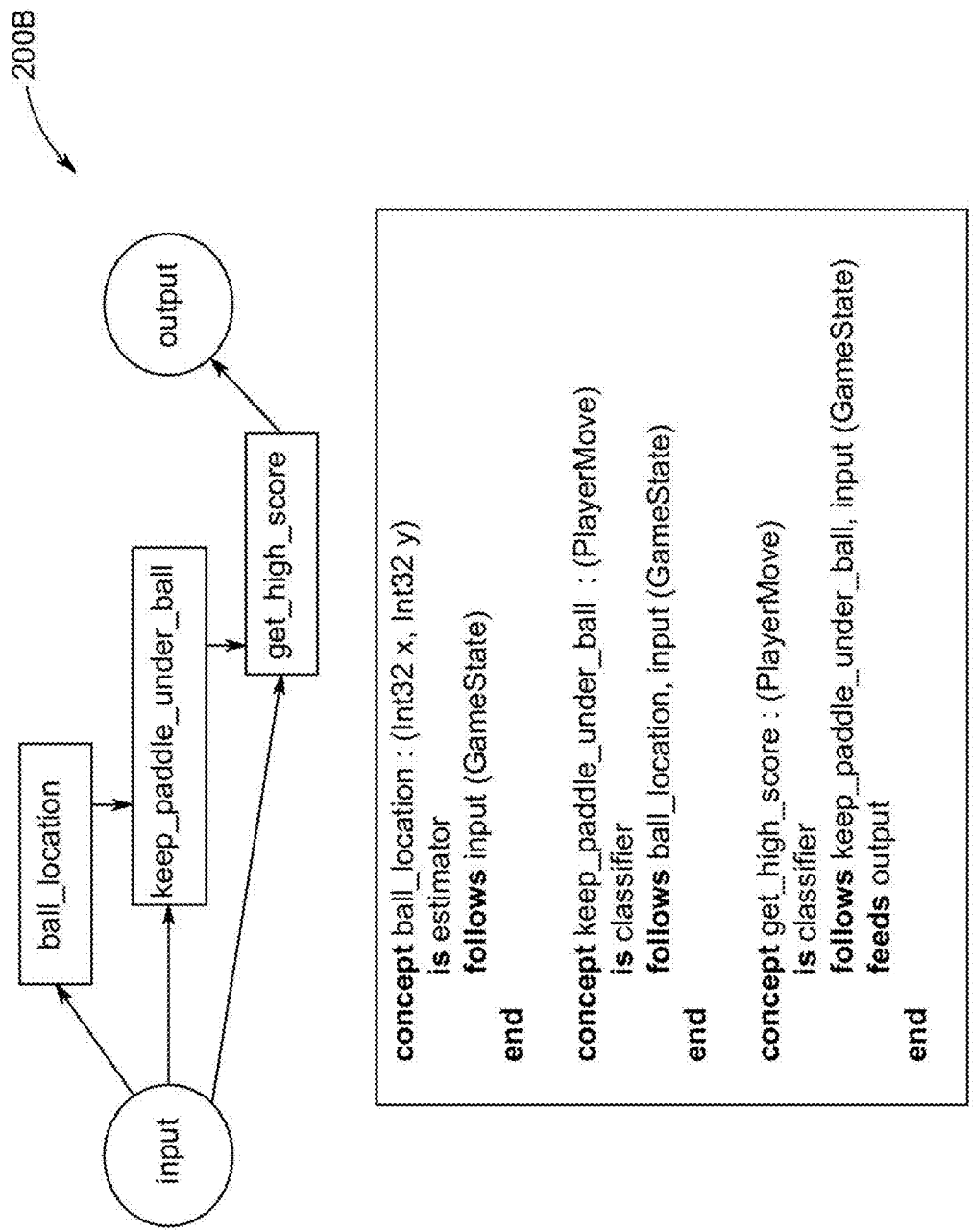
FIG. 26B provides a schematic illustrating a mental model in accordance with some embodiments.

FIG. 26B provides a schematic illustrating an AI system 300B in accordance with some embodiments.

Figure 33:
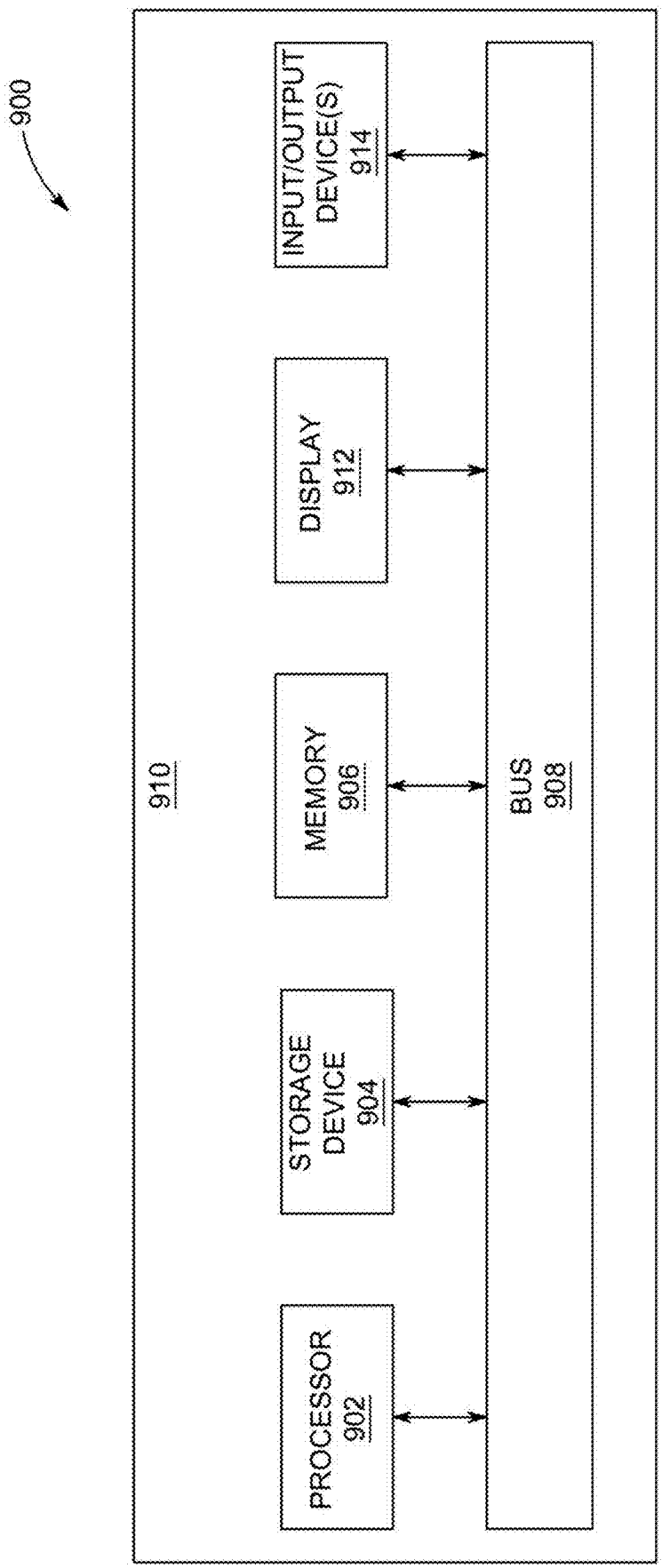
FIG. 33 illustrates a block diagram of an example computing device that may implement one or more aspects of the present disclosure, according to various embodiments of the present disclosure.

Following on AI system 300(a), bastion host and one or more CPU nodes can be on a public subnet for bidirectional communication through an Internet gateway. One or more or CPU nodes, as well as GPU nodes, can be on a private subnet communicatively coupled with public subnet by means of a subnet re between. one or more CPU nodes on public subnet can be utilized by compiler 222, and architect module 126 of FIGS. 20 and 31. O) ne or more or CPU nodes on private subnet can be utilized by instructor module 124, and GPU nodes can be utilized by learner module 128 and predictor module 129. As illustrated in FIG. 33(a) private subnet can be configured to send outgoing communications to Internet through a network address translation ("NAT") gateway.

As a non-limiting example, one or more methods of AI engine 65 can include, in some embodiments, compiling an assembly code, proposing a neural network, training neural network, and instantiating a trained AI model. assembly code can be compiled from a source code, wherein a compiler is configured to generate assembly code from source code written in a pedagogical programming language. source code can include a hierarchical mental model of one or more concepts to be learned by neural network using training data. source code can also include curricula of one or more lessons for training neural network on one or more concepts. neural network can be proposed by one or more AI-engine modules including an architect module 126 for proposing neural network from an assembly code. neural network can be trained by AI engine 65 in one or more training cycles with training data from one or more training data sources. Trained AI model can be instantiated by AI engine based on one or more concepts learned by neural network in one or more training cycles.

In one embodiment, AI engine 65 can include pushing or pulling training data. AI engine 65 can be configured for pushing or pulling training data from one or more training sources, each of which is selected from a simulator, a training data generator, a training data database, or a combination thereof. training data can be batched training data, streamed training data, or a combination thereof.

In one embodiment, AI engine 65 can include operating AI engine 65 in a training mode or a predicting mode during one or more training cycles. In the training mode, AI engine 65 can i) instantiate neural network conforming to neural network proposed by architect and ii) train neural network. In predicting mode, AI engine 65 can instantiate and execute trained AI model on training data through one or more API endpoints for one or more predictions in predicting mode.

In one embodiment, AI engine 65 can include heuristically picking an appropriate learning algorithm. AI engine can be configured for picking appropriate learning algorithm from a number of machine learning algorithms in one or more databases for training neural network proposed by architect.

In one embodiment, AI engine 65 can include proposing one or more additional neural networks to foregoing, initial neural network; heuristically picking an appropriate learning algorithm for each of one or more additional neural networks; training neural networks in parallel; instantiating one or more additional trained AI models 106; and identifying a best trained AI model among trained AI models. Architect module 126 can be configured for proposing one or more additional neural networks. AI engine 65 can be configured for heuristically picking appropriate learning algorithm from number of machine learning algorithms in one or more databases for each of one or more additional neural networks. AI engine 65 can be configured for training neural networks in parallel, wherein one or more additional neural networks can also be trained in one or more training cycles with training data from one or more training data sources. AI engine 65 can be configured to instantiate one or more additional trained AI models 106 based on concepts learned by one or more neural networks in one or more training cycles, and AI engine 65 can be configured to identify a best trained AI model among trained AI models 106.

In one embodiment, AI engine 65 can first include providing enabling AI for proposing neural networks from assembly code and picking appropriate learning algorithms from number of machine learning algorithms in one or more databases for training neural networks. AI engine 65 can continuously train a trained AI-engine neural network to provide enabling AI for proposing neural networks and picking appropriate learning algorithms.

In such embodiments, AI engine 65 can include keeping a record in one or more databases with a meta-learning module. record can include i) source code processed by AI engine 65, ii) mental models of source code, iii) training data used for training neural networks, iv) trained AI models 106, v) how quickly trained AI models 106 were trained to a sufficient level of accuracy, and vi) how accurate trained AI models 106 became in making predictions on training data.

In such embodiments, AI engine 65 can include making certain determinations. Such determinations can include when to train neural network on each of one or more concepts. Such determinations can alternatively or additionally include how extensively to train neural network on each of one or more concepts. Determinations can be based on relevance of each of one or more concepts in one or more predictions of trained AI model 106 based upon training data.

In such embodiments, AI engine 65 can include providing one or more training status updates on training neural network.

Figure 27:
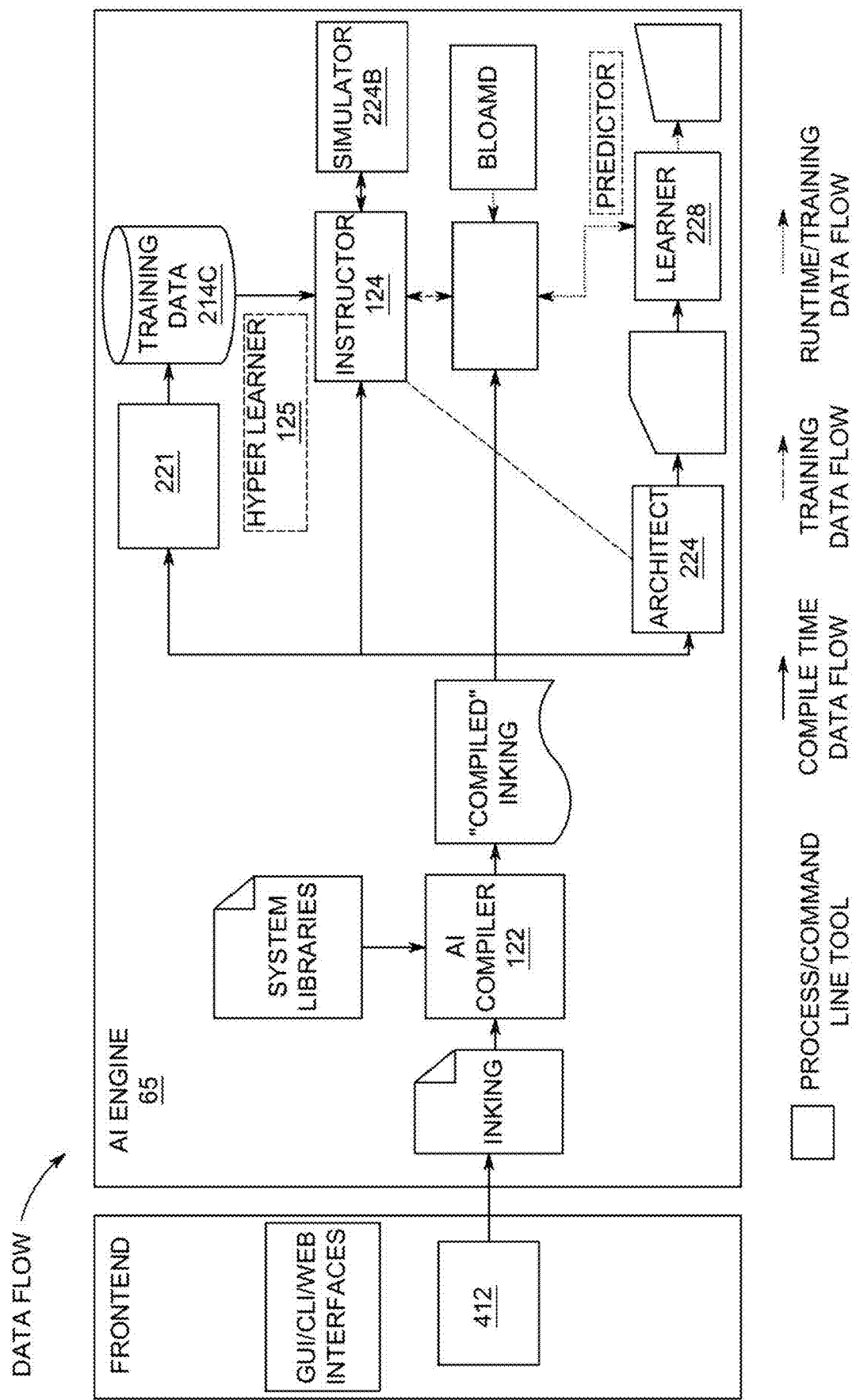
FIG. 27 provides a schematic illustrating an AI system in accordance with some embodiments.

FIGS. 27(a) and (b) illustrate a flow diagram of an embodiment of an AI database cooperating with a search engine and AI engine 65. In various embodiments, the example steps below need not be performed in sequential order and some of steps may be optional. In step 402, an AI database cooperates with a search engine and AI engine 65.

In step 404, AI database stores and indexes trained AI objects and its class of AI objects to have searchable criteria.

In step 405, parts of a trained AI model are stored and indexed as a collection of trained AI objects corresponding to a main concept and a set of sub concepts feeding parameters into main concept so that reuse, recomposition, and reconfiguration of all or part of a trained AI model is possible.

In step 408, a signature module calculates or concatenates a signature for a mental model of concepts in a trained AI model. For example, signature may in a form of hashing such that mental models of different trained AI models that have similar machine learning algorithmic characteristics have similar signatures.

In step 410, search engine can have one or both 4) parse scripted software code written in a pedagogical software programming language with search engine and n mapping that to one or more searchable criteria as well as 2) import data put into defined fields of user interface to use as searchable criteria to find relevant trained AI objects indexed in AI database.

In step 412, search engine 115 utilizes search criteria supplied from a user, from one or both 1) via scripted software code and 2) via data put into defined fields of a user interface, in order for search engine to retrieve one or more AI data objects that have already been trained as query results.

In step 414, search engine utilizes user supplied criteria to query for relevant trained AI objects by referring to 1) signatures of stored AI objects as well as 2) any indexed parameters for AI objects indexed by AI database.

In step 416, a user interface presents a population of known trained AI objects; and searching population of known trained AI objects to return a set of one or more already trained AI objects similar to a problem trying to be solved by user supplying search criteria.

In step 418, AI database is configured to be a set of one or more databases so that each database has a different profile and indexing. set of databases are configured to operate in a parallel to n send back accurate, fast, and efficient returns of trained AI objects that satisfy search query.

In step 420, AI database cooperate with AI engine to supply one or more AI objects. AI engine includes an architect module configured to create and optimize learning topologies of neural networks for AI objects; an instructor module configured to carrying out a training plan codified in a pedagogical software programming language; and a learner module configured to carrying out an actual execution of underlying AI learning algorithms during a training session, where architect module, when reconfiguring or recomposing AI objects, composes one or more trained AI data objects into a new AI model and instructor module and learner module cooperate with one or more data sources to train new AI model.

In step 422, AI database cooperates with an AI engine to cause any of reuse, reconfigure ability, and recomposition of one or more trained AI data objects into a new trained AI model.

Figure 28A:
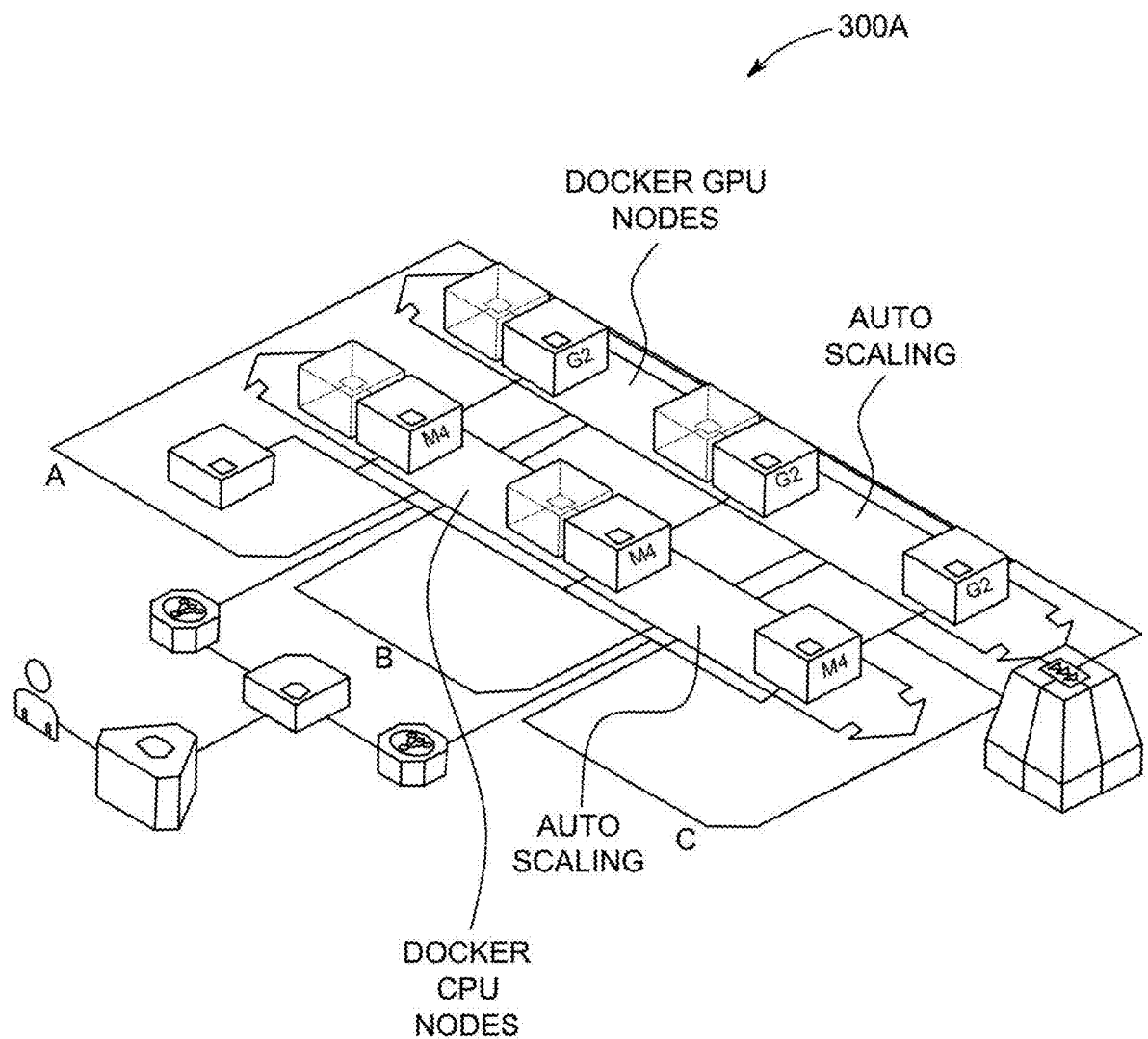
FIG. 28A provides a schematic illustrating an AI system in accordance with some embodiments.
Figure 28B:
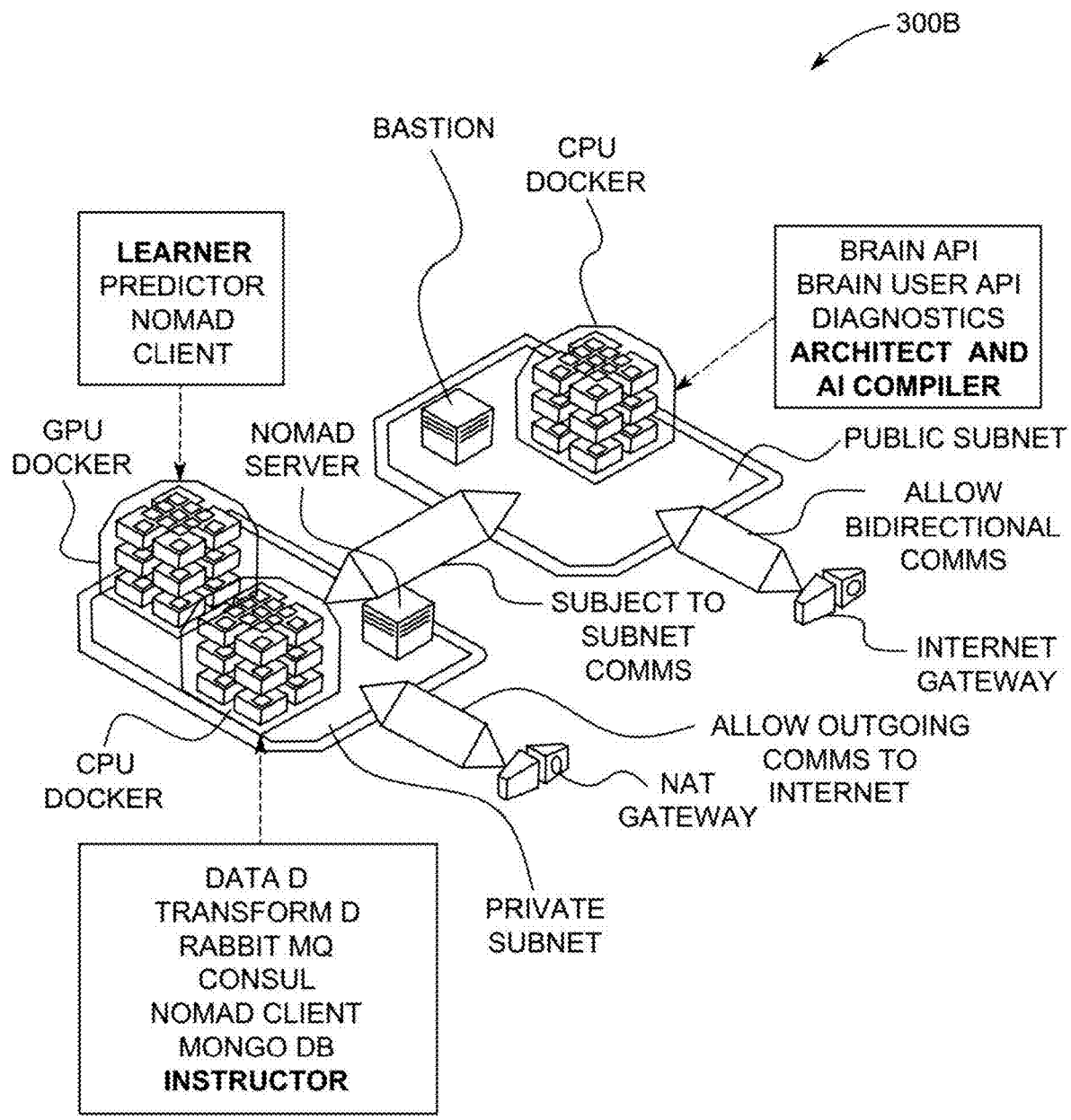
FIG. 28B provides a schematic illustrating an AI system in accordance with some embodiments.
Figure 30:
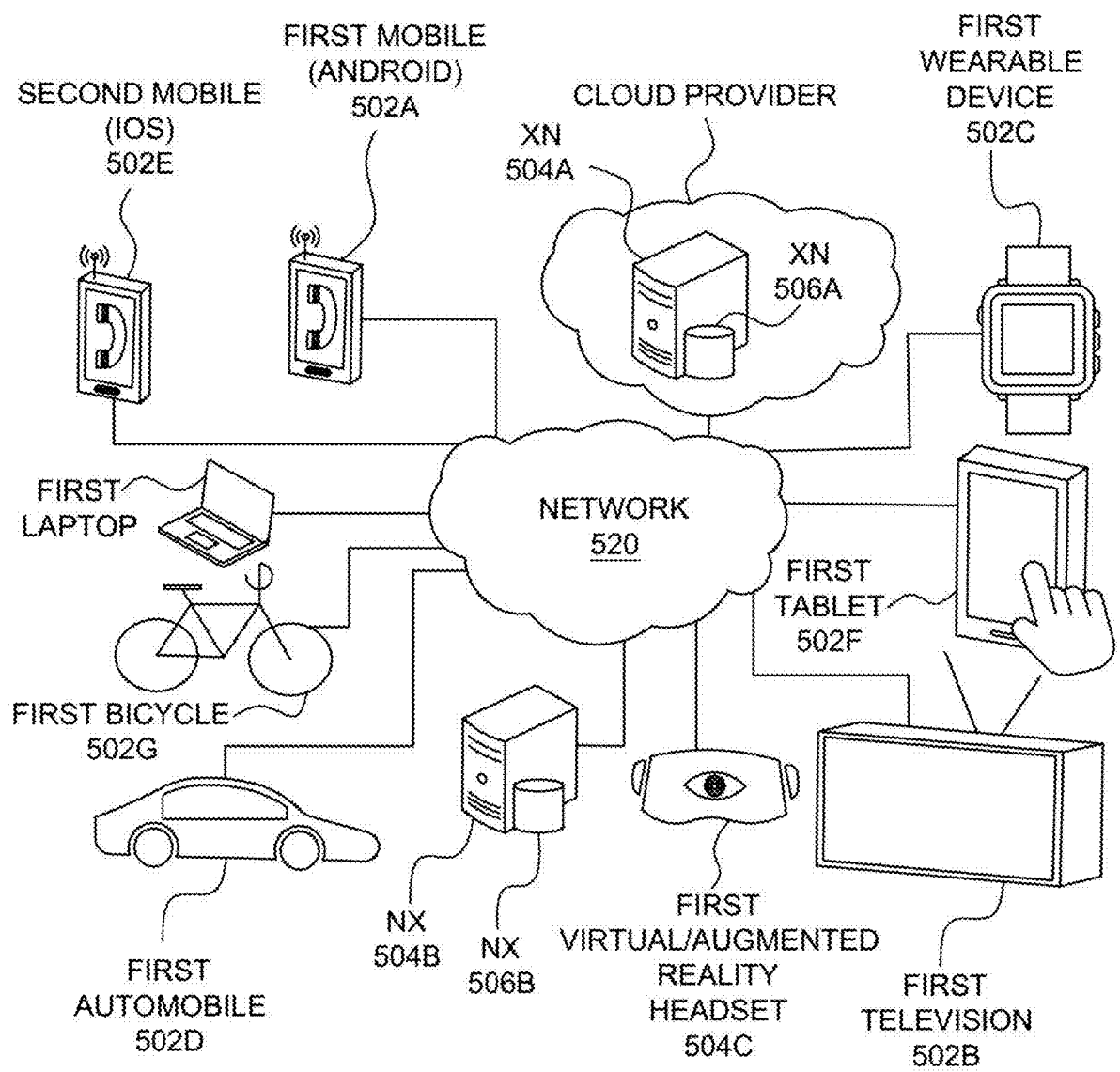
FIG. 30 provides one or more networks in accordance with some embodiments.

FIG. 28 illustrates one embodiment of present invention with a number of electronic systems and devices communicating with each or in a network environment in accordance with some embodiments. As a non-limiting example, network environment 500 has a communications network 520. network 520 can include one or more networks selected from an optical network, a cellular network, Internet, a Local Area Network ("LAN"), a Wide Area Network ("WAN"), a satellite network, a fiber network, a cable network, and various combinations. In some embodiments, communications network 520. As shown, re may be many server computing systems and many client computing systems connected to each or via communications network 520. However, it should be appreciated that, for example, a single client computing system can also be connected to a single server computing system. As such, FIG. 30 illustrates any combination of server computing systems and client computing systems connected to each or via communications network 520.

In one embodiment, communications network 520 can connect one or more server computing systems selected from at least a first server computing system 504A and a second server computing system 504B to each or and to at least one or more client computing systems as well. server computing system 504A can be, for example, one or more server systems. Server computing systems 504A and 504B can respectively optionally include organized data structures such as databases 506A and 506B. Each of one or more server computing systems can have one or more virtual server computing systems, and multiple virtual server computing systems can be implemented by design. Each of one or more server computing systems can have one or more firewalls to protect data integrity.

In one embodiment, at least one or more client computing systems can be selected from a first mobile computing device 502A (e.g., smartphone with an Android-based operating system), a second mobile computing device 502E (e.g., smartphone with an iOS-based operating system), a first wearable electronic device 502C (e.g., a smartwatch), a first portable computer 502B (e.g., laptop computer), a third mobile computing device or second portable computer 502F (e.g., tablet with an Android- or iOS-based operating system), a smart device or system incorporated into a first smart automobile 502D, a smart device or system incorporated into a first smart bicycle 502G, a first smart television 502H, a first virtual reality or augmented reality headset 504C, and like. client computing system 502B can be, for example, one of one or more client systems 210, and any one or more of or client computing system, (e.g., 502A, 502C, 502D, 502E, 502F, 502G, 502H, and/or 504C) can include, for example, software application or hardware-based system in which trained AI model can be deployed. Each of one or more client computing systems can have one or more firewalls to protect data integrity.

In one embodiment, server computing systems can be a cloud provider. A cloud provider can install and operate application software in a cloud (e.g., network 520 such as Internet) and cloud users can access application software from one or more of client computing systems. Generally, cloud users that have a cloud-based site in cloud cannot solely manage a cloud infrastructure or platform where application software runs. Thus, server computing systems and organized data structures with shared resources, where each cloud user is given a certain amount of dedicated use of shared resources. Each cloud user's cloud-based site can be given a virtual amount of dedicated space and bandwidth in cloud. Cloud applications can be different from or applications in its scalability, which can be achieved by cloning tasks onto multiple virtual machines at run-time to meet changing work demand. Load balancers distribute work over set of virtual machines. This process is transparent to cloud user, who sees only a single access point.

Cloud-based remote access can be coded to utilize a protocol, such as Hypertext Transfer Protocol ("HTTP"), to engage in a request and response cycle with an application on a client computing system such as a web-browser application resident on client computing system. cloud-based remote access can be accessed by a smartphone, a desktop computer, a tablet, or any or client computing systems, anytime and/or anywhere. cloud-based remote access is coded to engage in 1) request and response cycle from all web browser based applications, 3) request and response cycle from a dedicated on-line server, 4) request and response cycle directly between a native application resident on a client device and cloud-based remote access to one or more client computing system.

In an embodiment, server computing system 504A can include a server engine, a web page management component, a content management component, and a database management component. server engine can perform basic processing and operating-system level tasks. web page management component can handle creation and display or routing of web pages or screens associated with receiving and providing digital content and digital advertisements. Users (e.g., cloud users) can access one or more of server computing systems by means of a Uniform Resource Locator ("URL") associated therewith. Content management component can handle most of functions in embodiments described herein. database management component can include storage and retrieval tasks with respect to database, queries to database, and storage of data.

In some embodiments, a server computing system can be configured to display information in a window, a web page, or like. An application including any program modules, applications, services, processes, and or similar software executable when executed on, for example, server computing system 504A, can cause server computing system 504A to display windows and user interface screens in a portion of a display screen space. With respect to a web page, for example, a user via a browser on client computing system 502B can interact with web page, and n supply input to query/fields and/or service presented by user interface screens. web page can be served by a web server, for example, server computing system 504A, on any Hypertext Markup Language ("HTML") or Wireless Access Protocol ("WAP") enabled client computing system (e.g., client computing system 502B) or any equivalent. Client computing system 502B can host a browser and/or a specific application to interact with server computing system 504A. Each application has a code scripted to perform functions that software component is coded to carry out such as presenting fields to take details of desired information. Algorithms, routines, and engines within, for example, server computing system 504A can take information from presenting fields and put that information into an appropriate storage medium such as a database (e.g., database 506A). A comparison wizard can be scripted to refer to a database and make use of such data. applications may be hosted on, for example, server computing system 504A and served to specific application or browser of, for example, client computing system 502B. applications n serve windows or pages that allow entry of details.

Figure 29A:
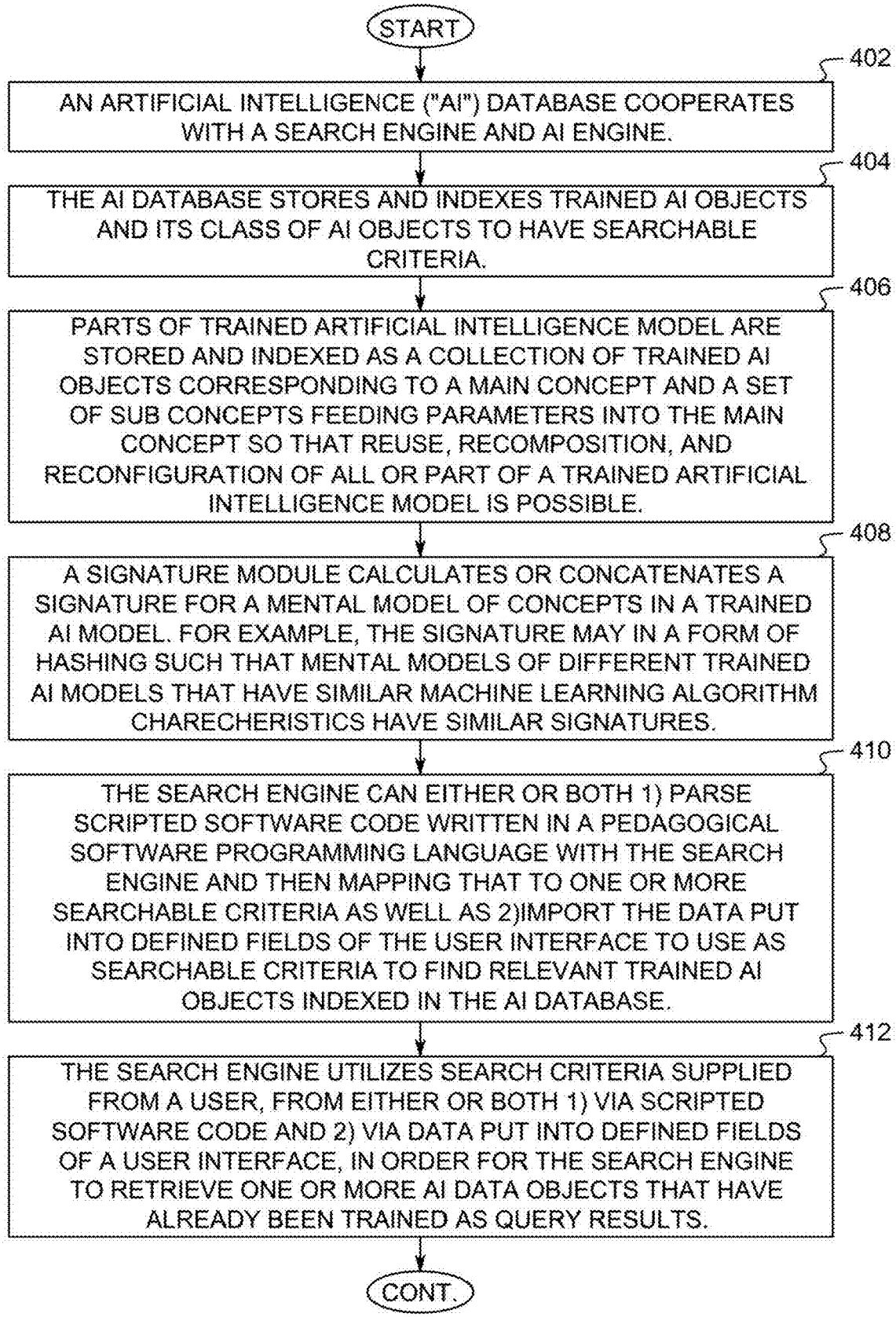

FIG. 29 illustrates a computing system 600 that can be, wholly or partially, part of one or more of server or client computing devices in accordance with some embodiments. Components of computing system 600 can include, but are not limited to, a processing unit 620 having one or more processing cores, a 6630, and a system bus 621 that couples various system components including system memory 630 to processing unit 620. system bus 621 may be any of several types of bus structures selected from a memory bus or memory controller, a peripheral bus, and a local bus using any of a variety of bus architectures.

Figure 31:
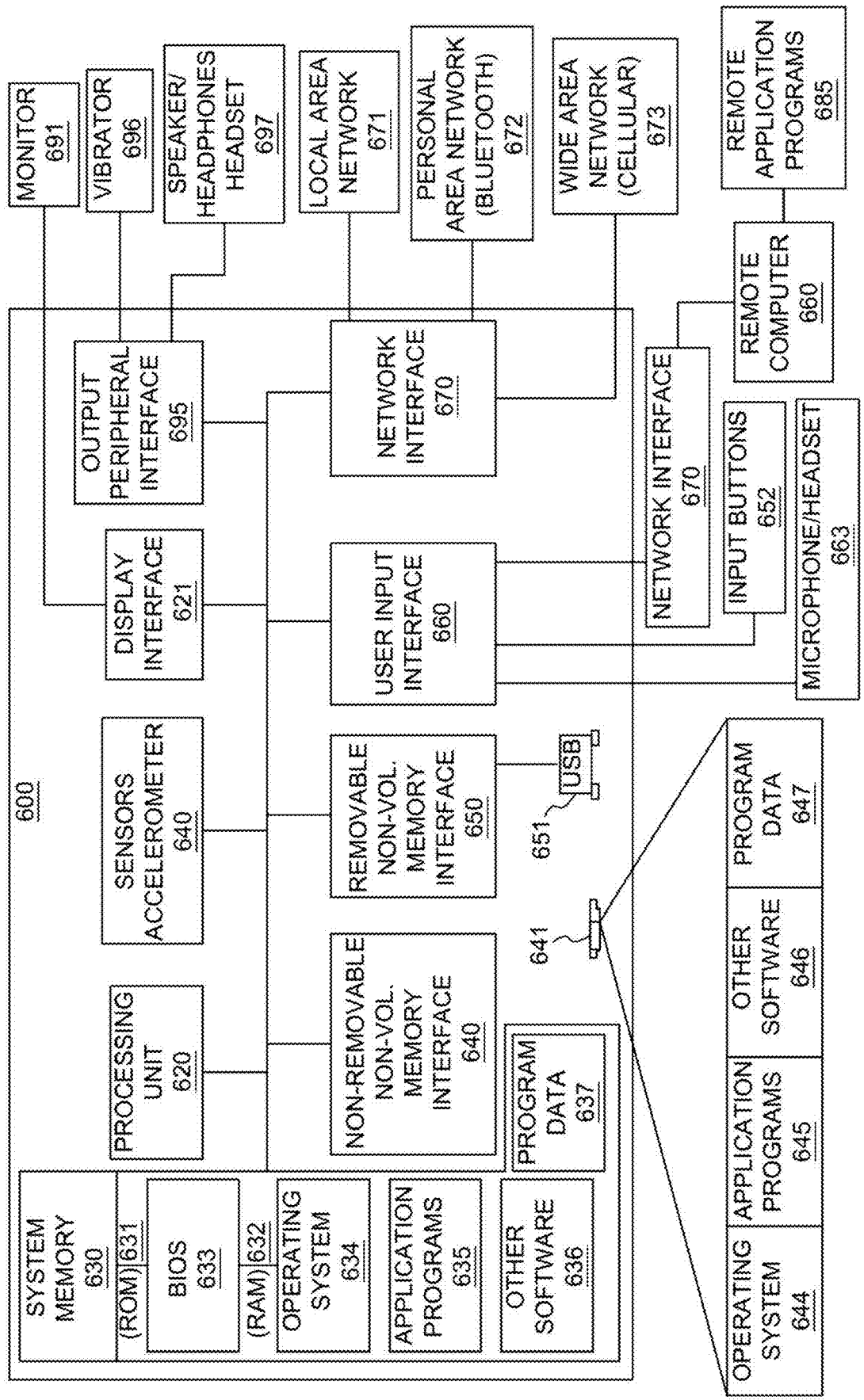
FIG. 31 provides one or more computing systems in accordance with some embodiments.

Computing system 600 typically includes a variety of computing machine-readable media. Computing machine-readable media can be any available media that can be accessed by computing system 600 and includes both volatile and nonvolatile media, and removable and non-removable media. By way of example, and not limitation, computing machine-readable media use includes storage of information, such as computer-readable instructions, data structures, or executable software or roof data. Computer-storage media includes, but is not limited to, RAM, ROM, EEPROM, flash memory or roof memory technology, CD-ROM, digital versatile disks (DVD) or roof optical disk storage, magnetic cassettes, magnetic tape, magnetic disk storage or roof magnetic storage devices, or any or tangible medium which can be used to store desired information and which can be accessed by computing device 600. Transitory media such as wireless channels are not included in machine-readable media. Communication media typically embody computer readable instructions, data structures, or executable software, or roof transport mechanism and includes any information delivery media. As an example, some client computing systems on network 620 need not have optical or magnetic storage.

system memory 630 includes computer storage media in form of volatile and/or nonvolatile memory such as read only memory (ROM) 631 and random access memory (RAM) 632. A basic input/output system 633 (BIOS) containing basic routines that help to transfer information between elements within computing system 600, such as during start-up, is typically stored in ROM 631. RAM 632 typically contains data and/or software that are immediately accessible to and/or presently being operated on by processing unit 620. By way of example, and not limitation, FIG. 31 illustrates that RAM 632 can include a portion of operating system 634, application programs 635, or executable software 636, and program data 637.

computing system 600 can also include or removable/non-removable volatile/nonvolatile computer storage media. By way of example only, FIG. 31 illustrates a solid-state memory 641. Or removable/non-removable, volatile/nonvolatile computer storage media that can be used in example operating environment include, but are not limited to, USB drives and devices, flash memory cards, solid state RAM, solid state ROM, and like. solid-state memory 641 is typically connected to system bus 621 through a non-removable memory interface such as interface 640, and USB drive 651 is typically connected to system bus 621 by a removable memory interface, such as interface 650.

Drives and/or associated computer storage media discussed above, provide storage of computer readable instructions, data structures, or executable software and or data for computing system 600. In FIG. 31, for example, solid state memory 641 is illustrated for storing operating system 644, application programs 645, or executable software 646, and program data 647. Operating system 644, application programs 645, or executable software 646, and program data 647 are given different numbers here to illustrate that, at a minimum, y are different copies.

A user may enter commands and information into computing system 600 through input devices such as a keyboard, touchscreen, or software or hardware input buttons 662, a microphone 663, a pointing device and/or scrolling input component, such as a mouse, trackball or touch pad. microphone 663 can cooperate with speech recognition software. se and or input devices are often connected to processing unit 620 through a user input interface 660 that is coupled to system bus 621, but can be connected by or interface and bus structures, such as a parallel port, game port, or a universal serial bus (USB). A display monitor 691 or ear type of display screen device is also connected to system bus 621 via an interface, such as a display interface 690. In addition to monitor 691, computing devices may also include or peripheral output devices such as speakers 697, a vibrator 699, and or output devices, which may be connected through an output peripheral interface 695.

computing system 6/00 can operate in a networked environment using logical connections to one or more remote computers/client devices, such as a remote computing system 680. remote computing system 680 can a personal computer, a hand-held device, a server, a router, a network PC, a peer device or ear common network node, and typically includes many or all of elements described above relative to computing system 600. logical connections can include a personal area network ("PAN") 672 (e.g., Bluetooth®), a local area network ("LAN") 671 (e.g., Wi-Fi), and a wide area network ("WAN") 673 (e.g., cellular network), but may also include or networks. Such networking environments are commonplace in offices, enterprise-wide computer networks, intranets and Internet. A browser application may be resident on computing device and stored in memory.

When used in a LAN networking environment, computing system 600 is connected to LAN 671 through a network interface or adapter 670, which can be, for example, a Bluetooth® or Wi-Fi adapter. When used in a WAN networking environment (e.g., Internet), computing system 600 typically includes some means for establishing communications over WAN 673. With respect to mobile telecommunication technologies, for example, a radio interface, which can be internal or external, can be connected to system bus 621 via network interface 670, or ear appropriate mechanism. In a networked environment, or software depicted relative to computing system 600, or portions thereof, may be stored in remote memory storage device. By way of example, and not limitation, illustrates remote application programs 685 as residing on remote computing device 680. It will be appreciated that network connections shown are examples and or means of establishing a communications link between computing devices may be used.

As discussed, computing system 600 can include a processor 620, a memory (e.g., ROM 631, RAM 632, etc.), a built in battery to power computing device, an AC power input to charge battery, a display screen, a built-in Wi-Fi circuitry to wirelessly communicate with a remote computing device connected to network.

It should be noted that present design can be carried out on a computing system such as that described with respect to. However, present design can be carried out on a server, a computing device devoted to message handling, or on a distributed system in which different portions of present design are carried out on different parts of distributed computing system.

Anor device that may be coupled to bus 621 is a power supply such as a DC power supply (e.g., battery) or an AC adapter circuit. As discussed above, DC power supply may be a battery, a fuel cell, or similar DC power source that needs to be recharged on a periodic basis. A wireless communication module can employ a Wireless Application Protocol to establish a wireless communication channel. wireless communication module can implement a wireless networking standard.

In some embodiments, software used to facilitate algorithms discussed herein can be embodied onto a non-transitory machine-readable medium. A machine-readable medium includes any mechanism that stores information in a form readable by a machine (e.g., a computer). For example, a non-transitory machine-readable medium can include read only memory (ROM); random access memory (RAM); magnetic disk storage media; optical storage media; flash memory devices; Digital Versatile Disc (DVD's), EPROMS, EEPROMs, FLASH memory, magnetic or optical cards, or any type of media suitable for storing electronic instructions.

Note, an application described herein includes but is not limited to software applications, mobile apps, and programs that are part of an operating system application. Some portions of this description are presented in terms of algorithms and symbolic representations of operations on data bits within a computer memory. se algorithmic descriptions and representations are means used by those skilled in data processing arts to convey substance of work most effectively to one skilled in art. An algorithm is here, and generally, conceived to be a self-consistent sequence of steps leading to a desired result. steps are those requiring physical manipulations of physical quantities. Usually, though not necessarily, se quantities take form of electrical or magnetic signals capable of being stored, transferred, combined, compared, and manipulated. It has proven convenient at times, principally for reasons of common usage, to refer to signals as bits, values, elements, symbols, characters, terms, numbers, or like. se algorithms can be written in a number of different software programming languages such as C, C+, or similar languages. Also, an algorithm can be implemented with lines of code in software, configured logic gates in software, or a combination of both. In an embodiment, logic consists of electronic circuits that follow rules of Boolean Logic, software that contain patterns of instructions, or any combination of both.

Many functions performed by electronic hardware components can be duplicated by software emulation. Thus, a software program written to accomplish those same functions can emulate functionality of hardware components in input-output circuitry.

Each of following references is expressly incorporated herein by reference in its entirety:

Abraham, Ittai, et al. "Low-distortion inference of latent similarities from a multiplex social network." SIAM Journal on Computing 44.3 (2015): 617-668.

Aldenderfer, M. S., and R. K. Blashfield. Cluster Analysis. Sage Publications, Los Angeles, 1985.

Anderberg, M. R. (1973). Cluster Analysis for Applications. Academic Press, New York.

Anderson, E. (1957). A semi-graphical method for analysis of complex problems. Proc. Nat. Acad. Sci. USA 43923-927.

Anderson, T. W. (1958). An Introduction to Multivariate Statistical Analysis. Wiley, New York.

Anderson, T. W., and Bahadur, R. R. (1962). classification into two multivariate normal distributions with different covariance matrices. Ann. Math. Statist. 33420-431.

Andrews, D. F. (1972). Plots of high-dimensional data. Biometrics 28 125-136.

Ankerst, M., M. M. Breunig, H.-P. Kriegel, and J. Sander. OPTICS: Ordering Points To Identify Clustering Structure. In Proc. of 1999 ACM-SIGMOD Intl. Conf. on Management of Data, pages 49-60, Philadelphia, Pa., June 1999. ACM Press.

Arabic, P. (1977). clustering representations of group overlap. J. Math. Soc. 5 112-128.

Arabic, P. and Carroll, J. D. (1980). MAPCLUS: A mamatical programming approach to fitting to ADCLUS model. Psychometrika 45211-235.

Arabic, P., L. Hubert, and G. D. Socte. An overview of combinatorial data analysis. In P. Arabic, L. Hubert, and G. D. Soete, editors, Clustering and Classification, pages 188-217. World Scientific, Singapore, January 1996.

Art, D., Gnanadesikan, R., and Kettenring, J. R. (1982). Data-based metrics for cluster analysis. Utilitas Mamatica 31A 75-99.

Asimov, D. (1985). Grand tour. SLAM J. Sci. Statist. Corn-put. 6 128-143.

Auffarth, Benjamin, Yasumasa Muto, and Yasuharu Kunii. "An artificial system for visual perception in autonomous Robots." Proceedings of IEEE International Conference on Intelligent Engineering Systems. 2005.

Babu, B. Hari, N. Subash Chandra, and T. Venu Gopal. "Clustering Algorithms For High Dimensional Data—A Survey Of Issues And Existing Approaches."

Baker, F. B. (1974). Stability of two hierarchical grouping techniques, Case I: Sensitivity to data errors. J. Amer. Statist. Assoc. 69440-445.

Ball, G., and D. Hall. A Clustering Technique for Summarizing Multivariate Data. Behavior Science, 12:153-155, March 1967.

Banerjee, A., S. Merugu, I. S. Dhillon, and J. Ghosh. Clustering with Bregman Divergences. In Proc. of 2004 SIAM Intl. Conf. on Data Mining, pages 234-245, Lake Buena Vista, Fla., April 2004.

Baraglia, R., Dazzi, P., Mordacchini, M., & Ricci, L. (2013). A peer-to-peer recommender system for self-emerging user communities based on gossip overlays. Journal of Computer and System Sciences, 79 (2), 291-308.

Baragliaa, R., Dazzia, P., Mordacchinib, M., & Riccic, L. A Peer-to-Peer Recommender System for self-emerging user communities based on Gossip Overlays. (2012)

Beck, Carolyn, et al. "Dynamic Coverage and Clustering: A Maximum Entropy Approach." Distributed Decision Making and Control. Springer London, 2012. 215-243.

Becker, P. (1968). Recognitions of Patterns. Polyteknisk, Copenhagen.

Bell, P. A. and Korey, J. L. (1975). QUICLSTR: A FORTRAN program for hierarchical cluster analysis with a large number of subjects. Behavioral Research Methods and Instrumentation 7575.

Berg, Mikko. "Human abilities to perceive, understand, and manage multi-dimensional information with visualizations." (2012).

Birkin, P. Survey Of Clustering Data Mining Techniques. Technical report, Accrue Software, San Jose, Calif., 2002.

Bhat, Sajid Yousuf, and Muhammad Abolish. "A density-based approach for mining overlapping communities from social network interactions." Proceedings of 2nd International Conference on Web Intelligence, Mining and Semantics. ACM, 2012.

Binder, D. A. (1978). Comment on 'Estimating mixtures of normal distributions and switching regressions. j Amer. Statist. Assoc. 73746-747.

Blashfield, R. K., Aldenderfer, M. S. and Morey, L. C. (1982). cluster analysis literature on validation. In Classifying Social Data. (H. Hudson, ed.) 167-176. Jossey-Bass, San Francisco.

Bock, H. H. (1985). On significance tests in cluster analysis. J. Classification 277-108

Boley, D. Principal Direction Divisive Partitioning. Data Mining and Knowledge Discovery, 2 (4): 325-344, 1998.

Bosley, Daniel, and Vivian Borst. "A General Unsupervised Clustering Tool for Unstructured Data." matrix 100:2.

Boratto, Ludovico. "Group artificial intelligence with automatic detection and classification of groups." (2012).

Bradley, P. S. and U. M. Fayyad. Refining Initial Points for K-Means Clustering. In Proc. of 15th Intl. Conf. on Machine Learning, pages 91-99, Madison, Wis., July 1998. Morgan Kaufmann Publishers Inc.

Breiman, L. Meisel, W. S., and Purcell, E. (1977). Variable kernel estimates of multivariate densities and ir calibration. Technometrics 19 135-144.

Brineman, L., Friedman, J. H., Olshen, R. A., and Stone, C. J. (1984). Classification and Regression Trees. Wadsworth, Belmont, Calif.

Broadbent, S. R. and Hammersley, J. M. (1957). Percolation Processes, I: Crystals and Mazes. Proc. Cambridge Philos. Soc. 53629-641.

Bu, Yingyi, et al. "HaLoop approach to large-scale iterative data analysis." VLDB Journal-International Journal on Very Large Data Bases 21.2 (2012): 169-190.

Buja, A., Hurify, C. and Mcdonald, J. A. (1986). A data viewer for multivariate data. Computer Science and Statistics: Proceedings of 18th Symposium on Interface 171-174.

Cacoullos, T. (1966). Estimation of a multivariate density. Ann. Math. Statist. 18 179-189.

Cal, Rui, et al. "Scalable music artificial intelligence by search." Proceedings of 15th international conference on Multimedia. ACM, 2007.

Carrizosa, Emilio, and Dolores Romero Morales. "Supervised classification and mamatical optimization." Computers & Operations Research 40.1 (2013): 150-165.

Chang, Chin-Chun, and Hsin-Yi Chen. "Semi-supervised clustering with discriminative random fields." Pattern Recognition 45.12 (2012): 4402-4413.

Chen, H., Gnanadesikan, R., and Kettenring, J. R. (1974). Statistical methods for grouping corporations. Sankhya B 36 1-28.

Chen, Yen Hung. "k Partition-Distance Problem." Journal of Computational Biology 19.4 (2012): 404-417.

Cheng, Hong, et al. "Clustering large attributed information networks: an efficient incremental computing approach." Data Mining and Knowledge Discovery 25.3 (2012): 450-477.

Chernoff, H. (1972). selection of effective attributes for deciding between hyposes using linear discriminant functions. In Frontiers of Pattern Recognition. (S. Watanabe, cd.) 55-60. Academic Press, New York.

Chernoff, H. (1973a). Some measures for discriminating between normal multivariate distributions with unequal covariance matrices. In Multivariate Analysis Ill. (P. R. Krishnaiah, ed.) 337-344. Academic Press, New York.

Chernoff, H. (1973b). use of faces to represent points in k-dimensional space graphically. J Amer. Statist. Assoc. 68 361-368.

Cherubini, Umberto, and Agnese Sironi. Bond Trading, Market Anomalies and Neural Networks: An Application with Kohonen Nets. No. _012. Society for Computational Economics.

Christou, Ioannis T., George Gekas, and Anna Kyrikou. "A classifier ensemble approach to TV-viewer profile adaptation problem." International Journal of Machine Learning and Cybernetics 3.4 (2012): 313-326.

Clunics-Ross, C. W. and Riffenburgh, R. H. (1960). Geometry and linear discrimination. Biometrika 47185-189.

Cormack, R. M. (1971). A review of classification (with discussion). J Roy. Statist. Soc. A 134321-367.

Cover, T. M. (1968). Estimation by nearest neighbor rule. IEEE Transactions Information ory IT-14 50-55.

Cover, T. M. and Hart, P. E. (1967). Nearest neighbor pattern classification. IEEE Transactions, Information ory IT-13 21-27.

Dallal, G. E. (1975) A user's guide to J. A. Hartigan's clustering algorithms. (unpublished manuscript) Yale University.

Day, N. E. (1969). Estimating components of a mixture of normal distributions. Biometrika 56463-474.

Day, N. E., and Kerridge, D. F., (1967). A general maximum likelihood discriminant. Biometrics 23313-323. 94 de Master, Trabajo Fin. "Novelty and Diversity Enhancement and Evaluation in Recommender Systems." (2012).

Defays, D. (1977). An efficient algorithm for a complete link method. Computer Journal 20364-366.

Derrac, Joaquín, Isaac Triguero, Salvador García, and Francisco Herrera. "Integrating instance selection, instance weighting, and feature weighting for nearest neighbor classifiers by coevolutionary algorithms."

As illustrated in FIG. 32, at block 814, it can be determined whether on-site care is required. At block 816, on-site care can be executed. At block 818, patient data and/or user interface(s) can be presented. In one embodiment, the software application provided to a care provider can enable the care provider to view the patient's physiological parameters (such as, but not limited to, blood oxygen saturation and/or temperature measurements) over the monitoring period.

At block 820, a patient can be diagnosed and/or treated for a health condition. For example, a clinician can review and/or a system can process the patient data and decide whether a health condition is present. For example, a preliminary indication of whether a patient has the coronavirus can be determined based on physiological parameters such as blood oxygen saturation and/or temperature measurements. A clinician can treat the patient based on the patient's physiological parameters (such as blood oxygen saturation and/or the temperature measurements) over the monitoring period. In some embodiments, a system can make a treatment recommendation based on the physiological parameters for review by a clinician. Treating the patient can include those disorders listed above regarding analysis of urine.

In some embodiments, the method and system 800 can be used to establish a monitoring environment for a user suspected of having a contagious respiratory infection. As described herein, the user can be monitored remotely from a care provider. The monitoring environment can include one or more sensors worn by the user, a wearable device worn by the user configured to communicate with the one or more sensors and to process information responsive to output from the one or more sensors. The monitoring environment can further include a user computing device configured to wirelessly communicate with the wearable device and to communicate with a remote care provider system over a network. The care provider system can be configured to be monitored by the care provider.

As non-limiting examples, any of the systems or methods described herein can also be applied to and/or used in conjunction with a health monitoring system that can assist organizations to manage infectious diseases. As described herein, additional health monitoring systems and use cases are described in the health monitoring application. For example, any of the systems or methods described herein can also be applied to and/or used in conjunction with risk states and/or proximity data.

FIG. 31 illustrates one embodiment of block diagram that illustrates components of a computing device 900. The computing device 900 can implement aspects of the present disclosure, and, in particular, aspects of the patient management and 111, including but not limited to a frontend server, a patient data service, the patient care management service, and/or the patient monitoring service. The computing device 900 can communicate with other computing devices.

The computing device 900 can include a hardware processor 902, a data storage device 904, a memory device 906, a bus 908, a display 912, and one or more input/output devices 914. A processor 902 can also be implemented as a combination of computing devices, e.g., a combination of a digital signal processor and a microprocessor, a plurality of microprocessors, one or more microprocessors in conjunction with a digital signal processor, or any other such configuration. The processor 902 can be configured, among other things, to process data, execute instructions to perform one or more functions, such as process one or more physiological signals to obtain one or measurements, as described herein. The data storage device 904 can include a magnetic disk, optical disk, or flash drive, etc., and is provided and coupled to the bus 908 for storing information and instructions. The memory 906 can include one or more memory devices that store data, including without limitation, random access memory (RAM) and read-only memory (ROM). The computing device 900 may be coupled via the bus 908 to a display 912, such as an LCD display or touch screen, for displaying information to a user, such as a clinician. The computing device 900 may be coupled via the bus 908 to one or more input/output devices 914. The input device 914 can include, but is not limited to, a keyboard, mouse, digital pen, microphone, touch screen, gesture recognition system, voice recognition system, imaging device (which may capture eye, hand, head, or body tracking data and/or placement), gamepad, accelerometer, or gyroscope.

In various embodiments, patient remote monitoring system 800 can be designed to help clinicians care for patients remotely over a period of time. The patient management system can include non-clinical spaces into advanced care environments with the one or more sensors 28, and vital signs monitors.

In one embodiment, illustrated in 34A, a network architecture 1000 for enabling remote management of patients. The network architecture 1000 can include a wireless sensor system 1010 that is capable of transmitting data to a mobile computing device 1012 enabled smartphones or another mobile computing device via a wireless link 1014. In some examples, the wireless link 1014 is a Bluetooth link. Other wireless links, such as NFC or WiFi can also be used for connection between the wireless sensor system 1010 and the mobile computing device 1012. The mobile computing device 1012 may communicate with a remote patient management system (RPMS) 1050 (see FIG. 34(c) that can display the collected data from wireless sensor system 1010 in a format that is readable by a patient or a user of the mobile computing device 1012. The RPMS 1050 can generate customized user interfaces as shown in more detail below. The mobile computing device 1012 in combination with the RPMS 1050 may enable transmission of the collected data to a server 1016 via a network connection link 1018. In some examples, the network connection link 1018 can include WiFi or other wireless broadband communication systems.

As non-limiting examples, the mobile computing device 1012 can be replaced with a connectivity hub that enables data collection from the wireless sensor system 1010 and transmits the collected data to the server 1016 via the communication link 1018. Not all users have access to a smart phone or mobile computing devices In one embodiment, patient remote monitoring system 1020 can access the collected data from the server 1016. The care provider monitoring system 1020 can include a computing system associated with a hospital, a caregiver (such as a primary provider), or a user (friends or family) that have permission to access the patient's data.

Figure 34A:
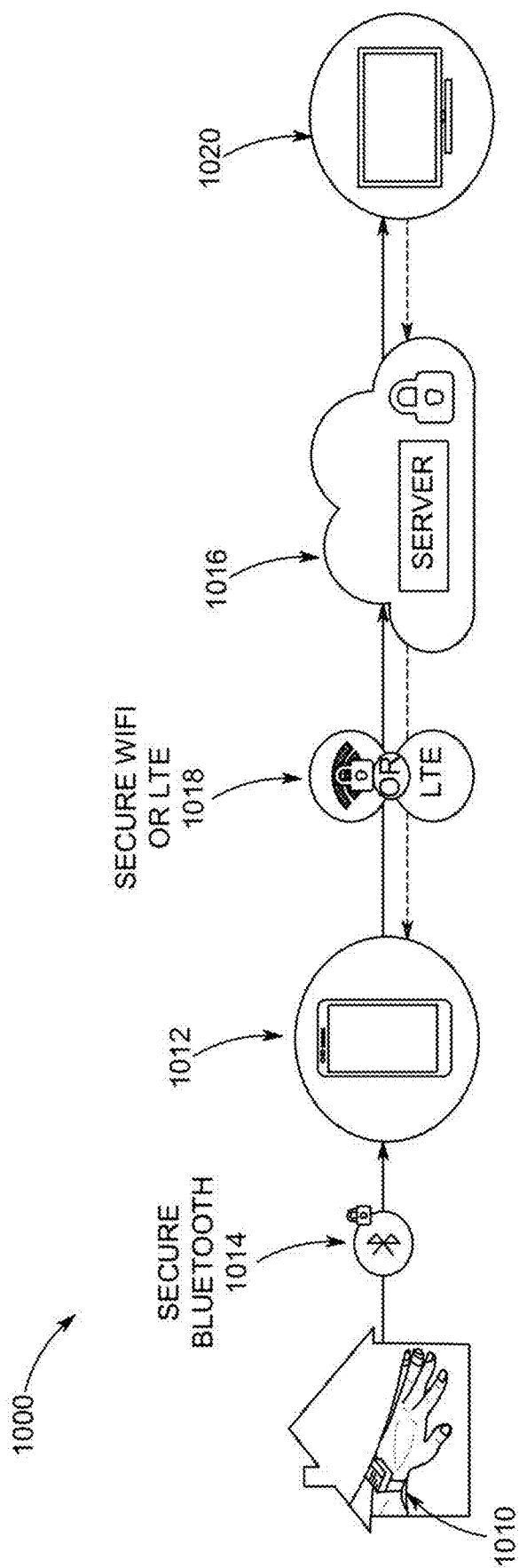
FIG. 34A illustrates a network architecture for enabling remote management of patients, according to some embodiments of the present disclosure.

As illustrated in FIG. 34A the wireless sensor system 1010 can collect physiological data. In some instances, the wireless sensor system 1010 can store 96 hours of data. This data can be streamed directly to the mobile computing device 1012. In some instances, when the mobile computing device 1012 is offline or not in the vicinity, data can be transferred when the mobile computing device 1012 is connected back with the wireless sensor system 1010. Accordingly, the wireless sensor system 1010 can keep monitoring and transmit when the mobile computing device 1012 is available.

As a non-limiting example, mobile computing device 1012 can associate the collected physiological data with patient identification information and transmit the data to the server 1016 as discussed above with respect to FIG. 34A. In one embodiment, a connectivity hub can also transmit the collected data to the server 1016. In some instances, the database is part of the server 1016, that it is located within same networking environment. The clinicians can access the collected patient data with a web browser. The clinicians can monitor one patient or multiple patients in a dashboard. The clinicians can access trend chart of the patients. Moreover, clinicians can obtain patient alerts via email. In some instances, patient data may be replicated on clinician's mobile computing device.

In various embodiments FIGS. 32(*a*) and (*b*) show a cloud based system, in some instances, connectivity between the wireless sensor system 1010 may be enabled inside the hospital using a network system. During a contagion management situation, it may be ideal for caregivers to not come in close contact with patients on frequent basis. In one embodiment, remote monitoring system can be created at the hospital. The wireless sensor system shown in FIG. 35) can be paired with a receiver. In some examples, the receiver can enable transmission of data to a patient monitor which in turn transmits the data to a hospital server. In other examples, the receiver is a communication hub that can directly transmit the data to the hospital server. Accordingly, caregivers can monitor multiple patients from a central location or even outside of a particular patient's hospital room, thereby limiting the interactions. This can also be useful in field hospitals that are set up on demand. A central monitoring station can be set up to monitor many patients through a local ad-hoc network.

In one embodiment, illustrated in FIG. 35C illustrates a block diagram of the RPMS 1050. The RPMS 1050 can be a software application including multiple engines that can be implemented across multiple devices, such as the mobile computing device 1012, the server 1016, and patient remote monitoring system 1020. The RPMS 1050 can collect data from multiple wireless sensor systems associated with a patient. The RPMS 1050 can further collect data from multiple patients that are monitored in different locations. The RPMS 1050 can collect data periodically for transmission to the server 1016. The RPMS 1050 can generate user interfaces for presenting the collected data and reports associated with the collected data.

Figure 34B:
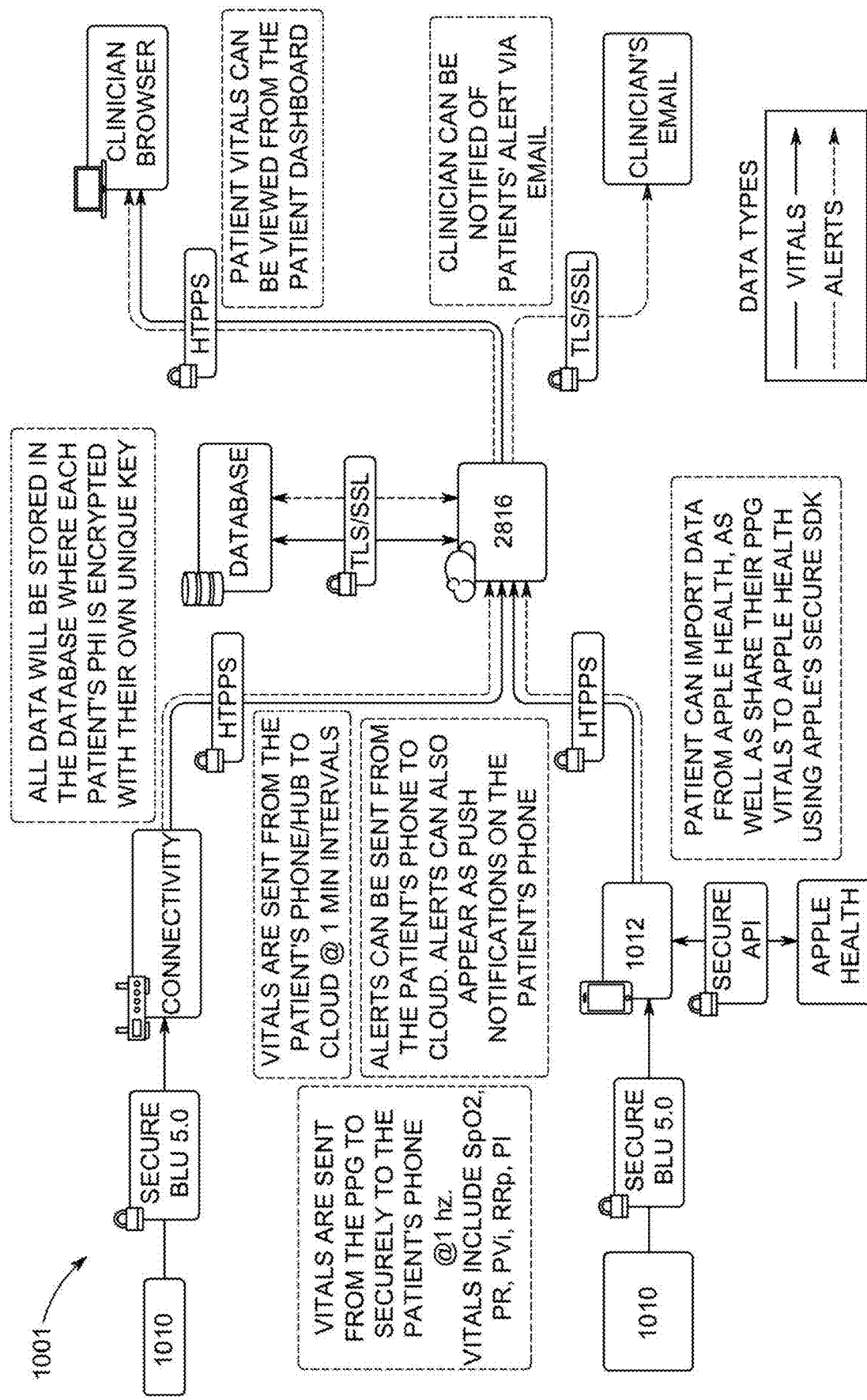
FIG. 34B illustrates an extended architecture, supplementing the architecture of FIG. 28A, according to some embodiments of the present disclosure.
Figure 34C:
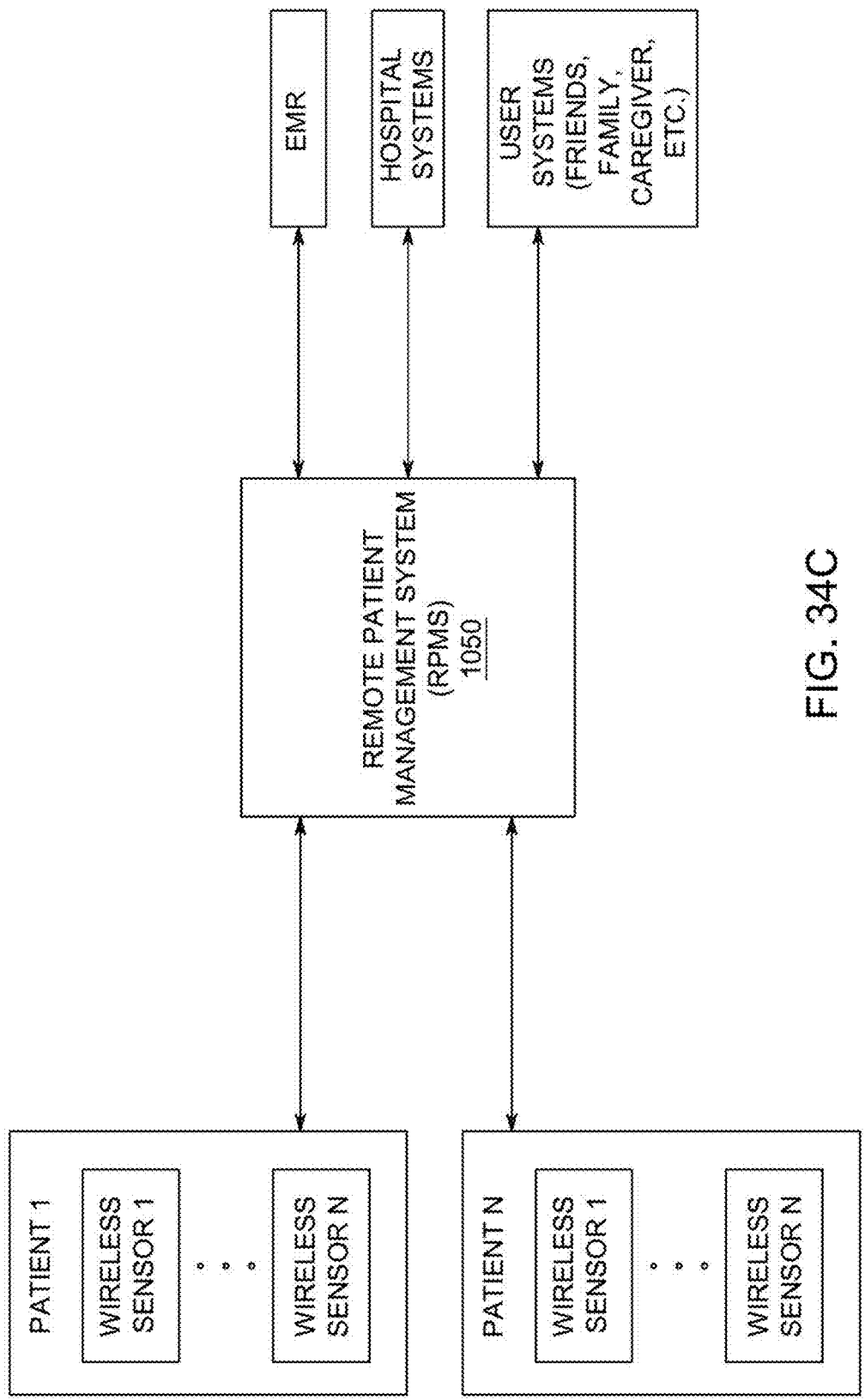
FIG. 34C illustrates a block diagram of the remote patient management system, according to some embodiments of the present disclosure.

FIGS. 34A-34C illustrates an example wireless sensor system 1010.

Figure 35:
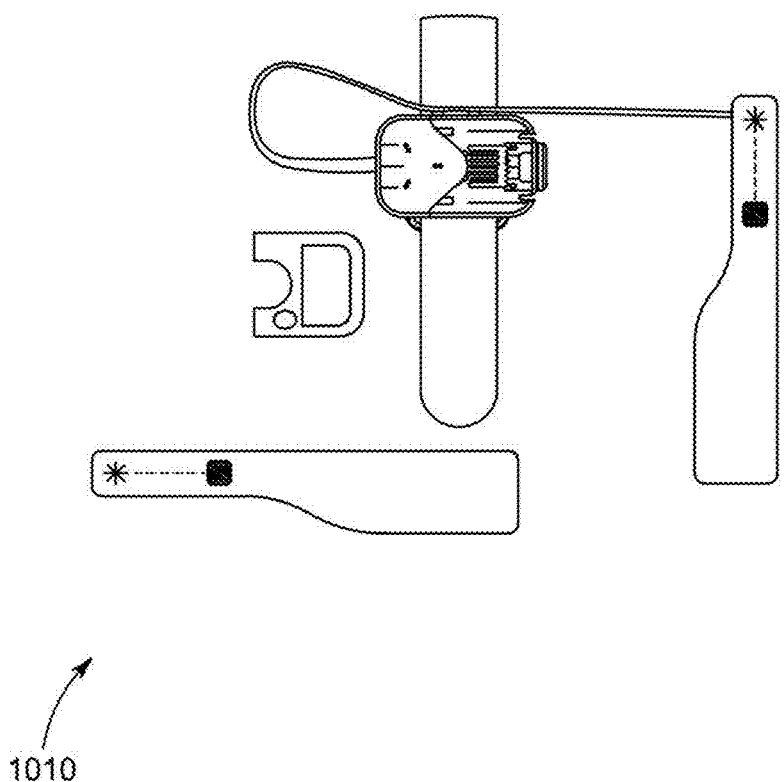
FIG. 35 illustrates an example wireless sensor system, according to some embodiments of the present disclosure.

RPMS 1050 can additionally or alternatively include a different wireless sensor system from the system shown in FIG. 35. In some instances, multiple wireless sensors systems 1010 can be part of a network architecture. For example, additional wireless sensors systems 1010 can include a temperature system, an ECG monitoring system, a blood pressure monitoring system, an acoustic sensor monitoring system, and any other physiological monitoring system capable of communication using the wireless link 1014.

In one embodiment, wireless sensor system(s) 1010 may include a pulse oximetry sensor with respiration rate monitoring. The pulse oximetry sensor can provide continuous respiration rate and oxygen saturation monitoring. The pulse oximetry sensor can also monitor the patient's pulse rate, variability index, perfusion, index, among other physiological parameters. Alternatively, or additionally, the wireless sensor system(s) 1010 may include a temperature monitoring system worn on the patient's body for measuring temperature.

In one embodiment, the remote monitoring system may include a digital discussion platform that may incorporate questions and possible answers to direct a patient consultation.

In some implementations, the patient remote monitoring management system may incorporate a secured data sharing to allow the remote patient surveillance system to share patient physiological data with others, for example, care providers, without the surveillance system gaining access to data. The secured data sharing may incorporate multiple layers of encryption with multiple entry points to some of the layers.

In one embodiment, RPMS 1050 may offer care providers a single-platform solution that couples a secure, cloud-based monitoring platform with patient sensors that can monitor blood oxygen saturation (SpCh), pulse rate, perfusion index, variability index, and respiration rate, and the like. Sensor 28 monitoring can be continuous or periodic.

Patients can be sent home with body fluid movement system 10 and one or more sensors 28 along with access to a secure, home-based, remote patient surveillance system. In some examples, patients may receive a multi-day supply of sensors. The RPMS 1050 can provide a dashboard user interface for a care provider to monitor multiple patient simultaneously. In some instances, the patients can be monitored for respiratory distress. Further, in some instances, the patients can be monitored during vims outbreaks. The RPMS 1050 may generate alerts when the patient may need urgent attention, including admission in the hospital based on monitoring a trend in physiological parameters.

In some implementations, the RPMS 1050 may offer programs or regimes that are digital replacement for traditional home-care plans and may be delivered to patients' smartphones. Programs can include for example, contagious disease monitoring, glucose monitoring, blood pressure monitoring, and other health condition monitoring and compliance. The programs can be predefined and selectable by the clinicians. The programs can be dynamically modified by changing government guidelines. The RPMS 1050 can actively remind patients to follow their regimen, automatically capture monitoring data from the wireless sensor system, and securely push (or transmit) the data to clinicians at the hospital for evaluation. In some implementations, the digital home-care plan may follow CDC and WHO guidance for monitoring suspected COVID-19 or other communicable disease subjects, which can be easily updated at any time to accommodate evolving guidance or hospital protocol. The patient management system can provide support during a surge in demand for medical care. The system can expand the ability of healthcare professionals to monitor conditions of patients that need non-urgent medical care (for example, patients with mild or moderate symptoms) and care for those patient remotely, while saving the limited hospital beds and urgent care facilities (for example, the intensive care units)

for patients who are in more critical conditions, such as needing intubation and/or assisted breathing. Conditions of the patients who are experiencing mild or moderate symptoms, or suspected of having been infected by virus or bacteria can be more accurately and/or more timely monitored using the patient management system, for example, as compared to asking the patient to self-report breathlessness, fever, or other medical conditions. In times of an epidemic or pandemic, patients who otherwise need their vital signs monitored by a healthcare professional can also receive medical care using the patient management system. The reduction in need for patients to visit the hospital or other clinical setting unless in urgent situations can also facilitate in reducing cross contamination (among patients, healthcare professionals, and other care takers) during epidemics or pandemics.

In one embodiment, RPMS 1050 may collect other physiological data, for example, temperature, heart rate, and the like from user inputs via interactive user interfaces.

In one embodiment, the RPMS 1050 may include a secured online portal that may allow care providers to easily track patient compliance, helping the care providers to identify when intervention may be needed, as well as providing insight to prioritize patients. With advanced automation features, institutions can more easily deploy home care monitoring at scale while ensuring clinicians stay informed of important developments in a patient's condition. In some implementations, the RPMS 1050 can be fully customizable to accommodate each institution's protocols, each patient's needs, and any changes in guidance. Additionally, and/or optionally, the remote patient surveillance system can be updated through the cloud by providers even after being deployed, for maximum flexibility as situations evolve.

It is to be understood that present disclosure is not to be limited to specific examples illustrated and that modifications and or examples are intended to be included within scope of appended claims. Moreover, although foregoing description and associated drawings describe examples of present disclosure in context of certain illustrative combinations of elements and/or functions, it should be appreciated that different combinations of elements and/or functions may be provided by alternative implementations without departing from scope of appended claims. Accordingly, parenetical reference numerals in appended claims are presented for illustrative purposes only and are not intended to limit scope of claimed subject matter to specific examples provided in present disclosure.

The invention claimed is:

1. A body fluid movement system, comprising:
a tube with a lumen, the tube having a proximal end with a plurality of drainage holes configured to drain a body fluid from a bladder, the tube having a distal end, a balloon coupled to the tube between its proximal and distal ends, the balloon configured to be positioned in an interior of a bladder, the proximal end configured to provide flow of a body fluid from the bladder through the tube lumen, the tube having an outlet port at the distal end of the tube coupled to an inlet port of a drainage bag for receiving body fluid from the lumen;
the drainage bag coupled to the tube, the drainage bag including at least one leg attachment configured to couple a patient's leg with the drainage bag; and
a locking mechanism without an integrated-check-valve, a pleated segment and not being a swivel snap connector, and positioned in a surrounding relationship around an entirety of an exterior of the output and inlet ports, providing a compression force applied by the locking mechanism to all of the exteriors of the outlet and inlet ports, the locking mechanism locking the outlet port and inlet port along with the locking mechanism when the patient's leg moves more than a predetermined distance, the locking mechanism configured to provide leak free flow of urine from the bladder to the drainage bag, and can continue to lock the outlet and inlet ports when the body fluid is drained from the drainage bag.

2. The body fluid movement apparatus of claim 1, wherein the tube includes a single tube or a plurality of tubes.

3. The body fluid movement apparatus of claim 1, wherein the inlet port of the drainage bag includes a plurality of ridges that engage with a plurality of ridges of the outlet port of the tube, providing a locking arrangement.

4. The body fluid movement apparatus of claim 1, wherein the inlet port of the draining bag includes a plurality of windings at the outlet port of the tube, providing a locking arrangement.

5. The body fluid movement apparatus of claim 1, wherein the inlet port of the drainage bag is engageably coupled to the outlet port of the tube with one or more of bends, notches, and recesses.

6. The body fluid movement apparatus of claim 1, wherein the tube is one or more of a hollow, partially or fully flexible tube(s) that can be a single tube, or multiple tubes with lumens that collects that body fluid from the bladder and are coupled to the drainage bag.

7. The body fluid movement apparatus of claim 1, wherein the drainage bag is expandable or flexible.

8. The body fluid movement apparatus bag of claim 1, wherein the drainage bag is a urinary leg bag with top and bottom leg attachments that can be flexible and adjustable.

9. The body fluid movement apparatus of claim 1, wherein the drainage bag is configured to reduce fluid back pressure.

10. The body fluid movement apparatus of claim 1, further comprising:
the balloon is configured to be inflated through an inflation port when the balloon is positioned in the bladder.

11. A body fluid movement apparatus including, a tube with a lumen, a proximal end, a distal end, and a balloon that anchors the proximal end in an interior of a bladder, the proximal end providing flow of a body fluid from the bladder, the apparatus further comprising:
a drainage bag for collecting the body fluid from the bladder, the drainage bag having an inlet port for receiving the body fluid, the drainage bag including at least a first leg attachment configured to couple a patient's leg with the drainage bag;
the proximal end having a plurality of body fluid draining holes that receive the body fluid from the bladder and allow it to be transported to and though the tube, the tube including an outlet port at the distal end of the tube coupled to the inlet port of the drainage bag; and
wherein the inlet port of the drainage bag and the outlet port of the tube are locked together by a locking mechanism without an integrated-check-valve, a pleated segment and not being swivel snap connector, and positioned in a surrounding relationship around an entirety of an exterior of the outlet and inlet ports, providing a compression force applied by the locking mechanism to all of the exteriors of the outlet and inlet ports, the locking mechanism locking the outlet port and inlet port when the patient's leg moves more than a predetermined distance.

12. The body fluid movement apparatus of claim 11, wherein at least a portion of the tube is made of a thermoplastic material.

13. The body fluid movement apparatus of claim 12, wherein at least a portion of the thermoplastic material includes a block copolymer.

14. The body fluid movement apparatus of claim 11, wherein a flexible material or one or more coiled sections of the tube extend and contract to relieve tension on the body fluid movement apparatus.

15. The body fluid movement apparatus of claim 11, wherein at least a portion of the tube is movable or extendable with respect to the drainage bag.

16. The body fluid movement apparatus of claim 11, further comprising: at least a second leg attachment.

17. The body fluid movement apparatus of claim 11, wherein the inlet port of the drainage bag includes a plurality of windings coupled to the outlet port of the tube, providing a locking arrangement.

18. The body fluid movement apparatus of claim 11, wherein the drainage bag is expandable or flexible.

19. The body fluid movement apparatus of claim 11, wherein the drainage bag is a urinary leg bag with top and bottom leg attachments that can be flexible and adjustable.

\* \* \* \* \*